(12) United States Patent
Zhang et al.

(10) Patent No.: US 12,741,280 B2
(45) Date of Patent: Sep. 22, 2026

(54) MICROFLUIDIC APPARATUS, DRIVING METHOD AND FORMATION METHOD THEREOF

(71) Applicant: Shanghai Tianma Micro-Electronics Co., Ltd., Shanghai (CN)

(72) Inventors: Kaidi Zhang, Shanghai (CN); Wei Li, Shanghai (CN); Baiquan Lin, Shanghai (CN); Yunfei Bai, Shanghai (CN); Kerui Xi, Shanghai (CN); Feng Qin, Shanghai (CN)

(73) Assignee: Shanghai Tianma Micro-Electronics Co., Ltd., Shanghai (CN)

( * ) Notice: Subject to any disclaimer, the term of this patent is extended or adjusted under 35 U.S.C. 154(b) by 1131 days.

(21) Appl. No.: 17/730,035

(22) Filed: Apr. 26, 2022

(65) Prior Publication Data

US 2023/0249181 A1 Aug. 10, 2023

(30) Foreign Application Priority Data

Feb. 9, 2022 (CN) ........................ 202210122213.6

(51) Int. Cl.
*B01L 3/00* (2006.01)
*C12Q 1/6806* (2018.01)

(52) U.S. Cl.
CPC ..... *B01L 3/50273* (2013.01); *B01L 3/502792* (2013.01); *B01L 2300/0816* (2013.01); *C12Q 1/6806* (2013.01)

(58) Field of Classification Search
CPC ........... B01L 3/5027; B01L 2300/0816; B01L 2400/0427; B01L 2200/10;
(Continued)

(56) References Cited

U.S. PATENT DOCUMENTS 767,964 A * 8/1904 Schweitzer ........... C02F 1/4674 99/451
2011/0095201 A1* 4/2011 Stolowitz .......... B01L 3/502792 250/428

(Continued)

FOREIGN PATENT DOCUMENTS

AU 2014218436 A1 * 8/2014 ................ B41J 2/06
CN 202393970 U 8/2012

(Continued)

OTHER PUBLICATIONS

Choi, K., Ng, A. H., Fobel, R., & Wheeler, A. R. (2012). Digital microfluidics. Annual review of analytical chemistry (Palo Alto, Calif.), 5, 413-440. https://doi.org/10.1146/annurev-anchem-062011-143028.*

*Primary Examiner* — Jennifer Dieterle
(74) *Attorney, Agent, or Firm* — Anova Law Group, PLLC

(57) ABSTRACT

A microfluidic apparatus, a driving method, and a formation method are provided. An example microfluidic apparatus includes a first substrate and a second substrate. The first substrate and the second substrate are both smooth substrates. An electrode array layer is on a side of the first substrate; and a second electrode layer is on a side of the second substrate. The electrode array layer at least includes a plurality of first electrodes and a plurality of second electrodes. The first substrate includes a first region and a second region, the plurality of first electrodes is in the first region, and the plurality of second electrode is in the second region. A distance D1 between the first substrate and the second substrate in the first region is greater than a distance D2 between the first substrate and the second substrate in the second region.

18 Claims, 49 Drawing Sheets

(58) Field of Classification Search
CPC ..... B01L 2300/0887; B01L 2400/0415; B01L 3/50273; B01L 3/502792; C12Q 1/6806
See application file for complete search history.

(56) References Cited

U.S. PATENT DOCUMENTS

| | | | | |
|---|---|---|---|---|
| 2015/0014171 | A1* | 1/2015 | Lin | B03C 5/028 204/643 |
| 2016/0184823 | A1* | 6/2016 | Fischer | B01L 3/502707 422/502 |
| 2016/0327515 | A1* | 11/2016 | Wang | B01L 3/502715 204/451 |
| 2019/0015832 | A1* | 1/2019 | Parry-Jones et al. | B01L 3/502792 422/502 |
| 2020/0347840 | A1* | 11/2020 | Paolini, Jr. | F04B 17/03 |
| 2020/0391212 | A1* | 12/2020 | Foley et al. | B01L 3/50273 204/450 |
| 2024/0207852 | A1* | 6/2024 | Fan | B01L 3/502792 |
| 2024/0376524 | A1* | 11/2024 | Wu | C12Q 1/6806 |

FOREIGN PATENT DOCUMENTS

| | | |
|---|---|---|
| CN | 110270386 A | 9/2019 |
| CN | 111108373 A | 5/2020 |

* cited by examiner

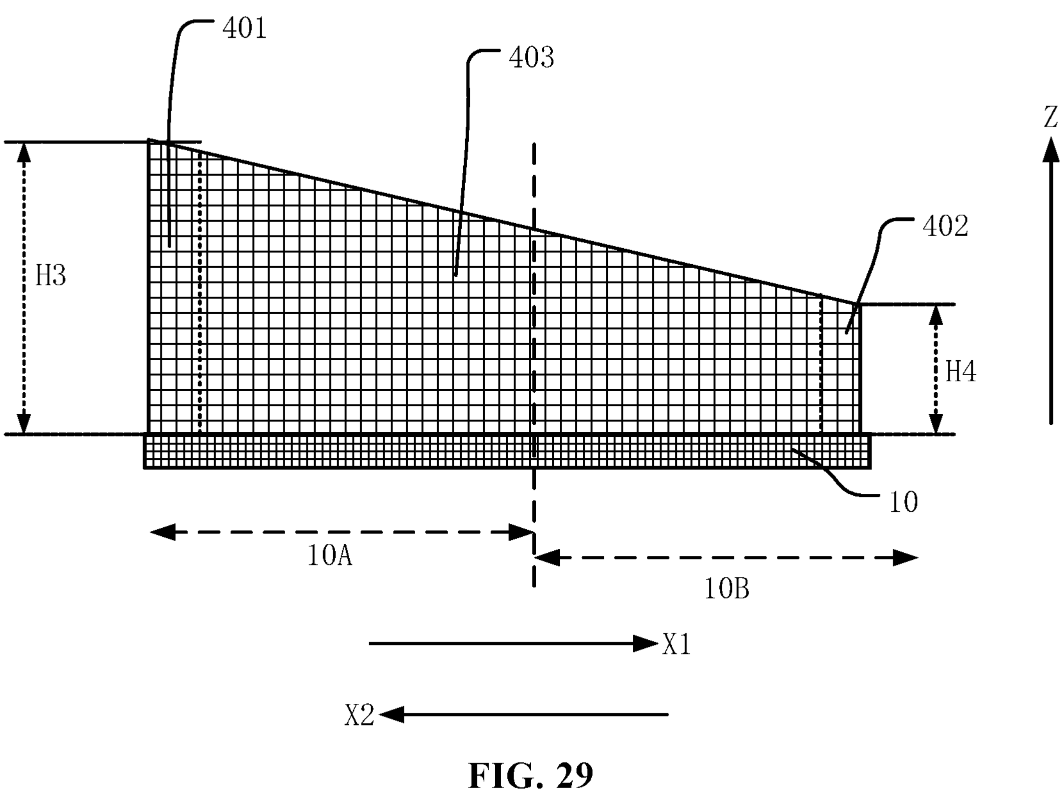

FIG. 29

In the first direction, along a direction pointing from the first region to the second region, connecting the second electrode layer to the ground signal, sequentially providing a driving voltage to the plurality of first electrodes, and driven by electric fields formed between the plurality of first electrodes and the second electrode layer, moving a first droplet between the first substrate and the second substrate along the direction pointing from the first region to the second region

S10

After the first droplet moves to one first electrode adjacent to the plurality of second electrodes, disconnecting a driving voltage of the one first electrode, providing a driving voltage to the plurality of second electrodes, and moving the first droplet on the plurality of second electrodes and splitting the first droplet into a plurality of second droplets, where a size of a second droplet of the plurality of second droplets is less than a size of the first droplet

Figure 35:
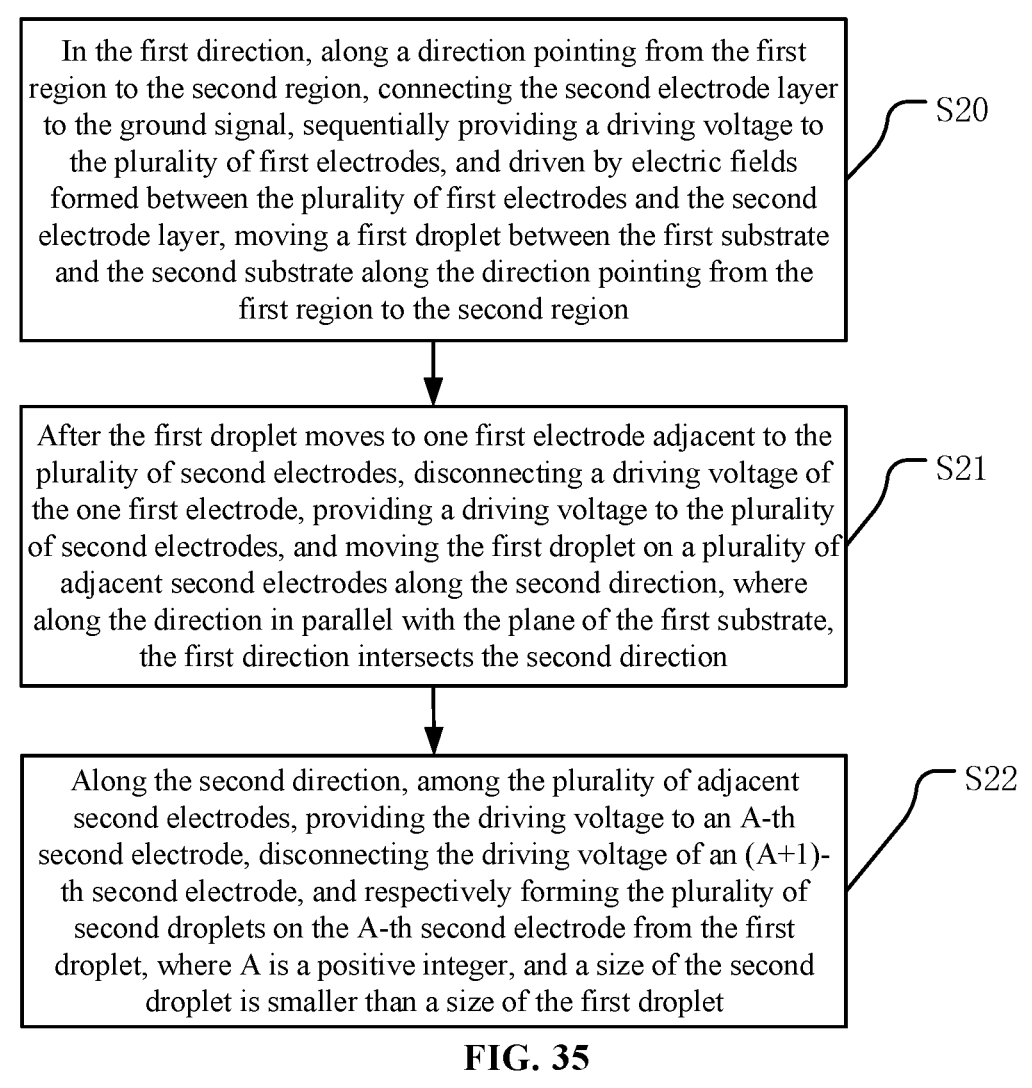

In the first direction, along a direction pointing from the first region to the second region, connecting the second electrode layer to the ground signal, sequentially providing a driving voltage to the plurality of first electrodes, and driven by electric fields formed between the plurality of first electrodes and the second electrode layer, moving a first droplet between the first substrate and the second substrate along the direction pointing from the first region to the second region

S20

After the first droplet moves to one first electrode adjacent to the plurality of second electrodes, disconnecting a driving voltage of the one first electrode, providing a driving voltage to the plurality of second electrodes, and moving the first droplet on a plurality of adjacent second electrodes along the second direction, where along the direction in parallel with the plane of the first substrate, the first direction intersects the second direction

S21

Along the second direction, among the plurality of adjacent second electrodes, providing the driving voltage to an A-th second electrode, disconnecting the driving voltage of an (A+1)-th second electrode, and respectively forming the plurality of second droplets on the A-th second electrode from the first droplet, where A is a positive integer, and a size of the second droplet is smaller than a size of the first droplet

Figure 36:
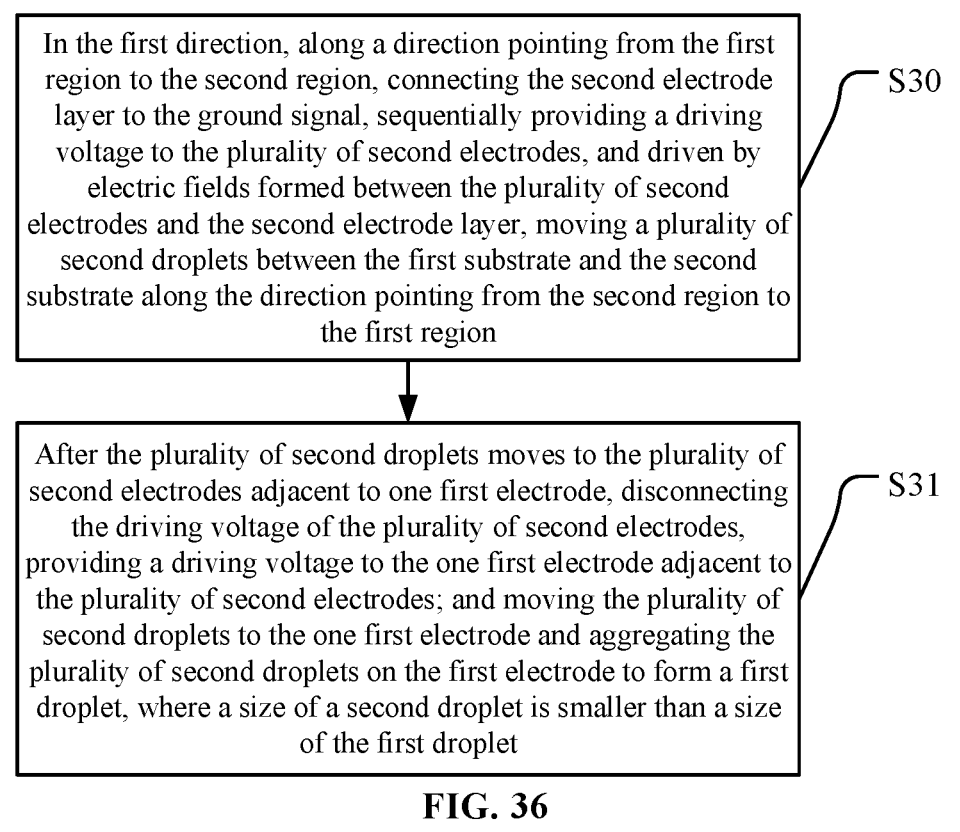

In the first direction, along a direction pointing from the first region to the second region, connecting the second electrode layer to the ground signal, sequentially providing a driving voltage to the plurality of second electrodes, and driven by electric fields formed between the plurality of second electrodes and the second electrode layer, moving a plurality of second droplets between the first substrate and the second substrate along the direction pointing from the second region to the first region

S30

After the plurality of second droplets moves to the plurality of second electrodes adjacent to one first electrode, disconnecting the driving voltage of the plurality of second electrodes, providing a driving voltage to the one first electrode adjacent to the plurality of second electrodes; and moving the plurality of second droplets to the one first electrode and aggregating the plurality of second droplets on the first electrode to form a first droplet, where a size of a second droplet is smaller than a size of the first droplet

MICROFLUIDIC APPARATUS, DRIVING METHOD AND FORMATION METHOD THEREOF

CROSS-REFERENCE TO RELATED APPLICATION

This application claims the priority of Chinese Patent Application No. 202210122213.6, filed on Feb. 9, 2022, the content of which is incorporated herein by reference in its entirety.

TECHNICAL FIELD

The present disclosure generally relates to the field of microfluidic technology and, more particularly, relates to a microfluidic apparatus, and its driving method and formation method.

BACKGROUND

Microfluidic technology is mainly characterized by fluid manipulation in the micron or smaller scale space. Such technology has formed inter-discipline with various subjects such as chemistry, biology, engineering and physics, showing a wide range of application prospects. Droplet microfluidic technology has received extensive attention due to its advantages of simple fluid manipulation, high mono-dispersity, miniaturization, low cost, high sensitivity, high throughput, and the like. The application of droplet microfluidic technology mainly lies in droplet manipulation, such as implementation of droplet splitting, fusion, merging, sorting and other functions. Therefore, the application of microfluidic technology in various fields, such as biomedical research, drug synthesis screening, environmental monitoring and protection, health and quarantine, forensic identification, and detection of biological reagents, has extremely broad prospects. Microfluidic technology mainly uses the principle of dielectric wetting. By adjusting the electric field between the upper and lower substrates of a microfluidic chip, the surface tension between droplet surface and solid is changed, thereby changing the contact angle between the droplet surface and solid and realizing the droplet operation and control.

In the existing technology, the cell thickness of the double-substrate structure of the digital microfluidic chip has a fixed height, which has poor compatibility with droplets of different sizes. Furthermore, for operations of droplets of different sizes, requirements for the cell thickness are different. For the droplet of a certain size, if the cell thickness is excessively small, the droplet movement resistance may be excessively large, and if the cell thickness is excessively large, the contact area between the droplet and the upper substrate may be excessively small or inaccessible, which may not be beneficial for effective driving droplets. Therefore, the cell thickness also needs to match sizes of the droplets and electrodes, and the size of the droplet depends on the product of the electrode area and the cell thickness between the upper and lower substrates. Therefore, the microfluidic apparatuses in the existing technology may have poor compatibility for controlling droplets of different sizes and be difficult to be compatible with the cell thickness requirements for merging and splitting droplets of different sizes.

Therefore, there is a need to provide a microfluidic apparatus and its driving method and formation method, which can be compatible with driving of droplets of different sizes, realize the operation of splitting or merging various droplets, and optimize operational performance including digital microfluidic droplet generation, division, merging, and the like.

SUMMARY

One aspect of the present disclosure provides a microfluidic apparatus. The microfluidic apparatus includes a first substrate and a second substrate which are oppositely disposed. The first substrate and the second substrate are both smooth substrates; an electrode array layer is on a side of the first substrate facing the second substrate; and a second electrode layer is on a side of the second substrate facing the first substrate; the electrode array layer at least includes a plurality of first electrodes and a plurality of second electrodes; in a direction in parallel with a plane of the first substrate, the first substrate includes a first region and a second region along a first direction; the plurality of first electrodes is in the first region, and the plurality of second electrode is in the second region; and in a direction perpendicular to the plane of the first substrate, a distance between the first substrate and the second substrate in the first region is D1, and a distance between the first substrate and the second substrate in the second region is D2, where D1>D2.

Other aspects of the present disclosure can be understood by those skilled in the art in light of the description, the claims, and the drawings of the present disclosure.

BRIEF DESCRIPTION OF THE DRAWINGS

The accompanying drawings, which are incorporated into a part of the specification, illustrate embodiments of the present disclosure and together with the description to explain the principles of the present disclosure.

FIG. 29 illustrates a front structural view of a first substrate in FIG. 28;

FIG. 30 illustrates a flowchart of a driving method of a microfluidic apparatus according to various embodiments of the present disclosure;

FIG. 35 illustrates a flowchart of another driving method of a microfluidic apparatus according to various embodiments of the present disclosure;

FIG. 36 illustrates a flowchart of another driving method of a microfluidic apparatus according to various embodiments of the present disclosure;

DETAILED DESCRIPTION

Figure 1:
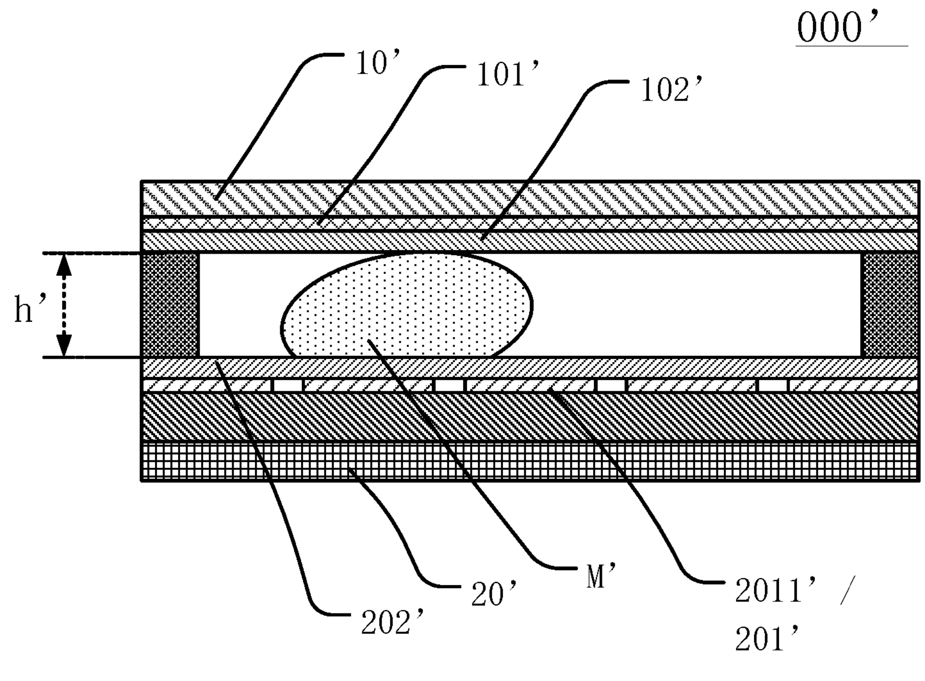
FIG. 1 illustrates a structural schematic of a microfluidic apparatus.

Various exemplary embodiments of the present disclosure are be described in detail with reference to the accompanying drawings. It should be noted that unless specifically stated otherwise, the relative arrangement of components and steps, numerical expressions and numerical values described in these embodiments may not limit the scope of the present disclosure.

The following description of at least one exemplary embodiment may be merely illustrative and may not be used to limit the present disclosure and its application or use.

The technologies, methods, and apparatuses known to those skilled in the art may not be discussed in detail, but where appropriate, the technologies, methods, and apparatuses should be regarded as a part of the present disclosure.

In all examples shown and discussed herein, any specific value should be interpreted as merely exemplary, rather than as a limitation. Therefore, other examples of the exemplary embodiment may have different values.

It should be noted that similar reference numerals and letters indicate similar items in the following drawings. Therefore, once an item is defined in one drawing, it does not need to be further discussed in the subsequent drawings.

Figure 2:
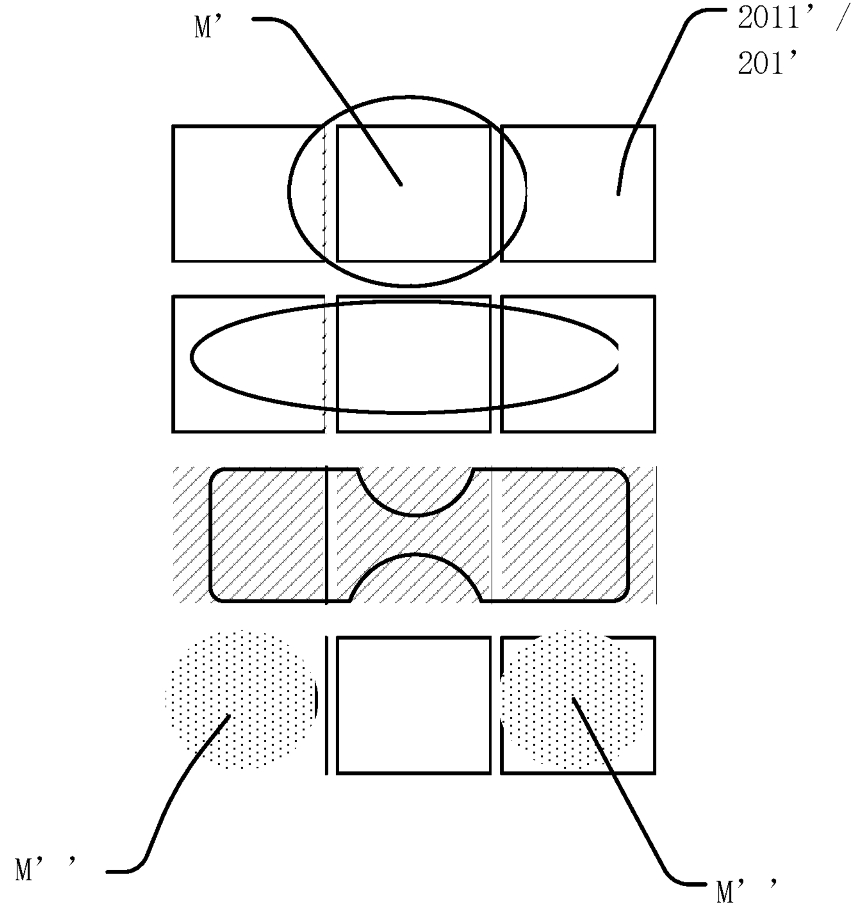
FIG. 2 illustrates a schematic of a basic process of splitting a droplet using the microfluidic apparatus of FIG. 1.
Figure 3:
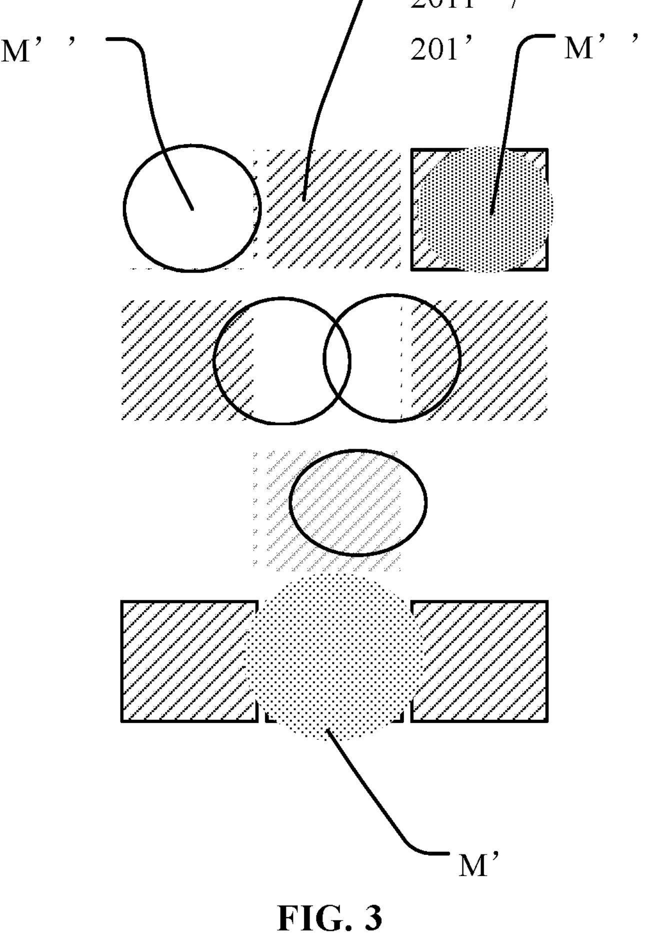
FIG. 3 illustrates a schematic of a basic process of merging droplets using the microfluidic apparatus of FIG. 1.

In the existing technology, as shown in FIGS. 1-3, FIG. 1 illustrates a structural schematic of a microfluidic apparatus; FIG. 2 illustrates a schematic of a basic process of performing droplet splitting using the microfluidic apparatus of FIG. 1; and FIG. 3 illustrates a schematic of a basic process of performing droplet splitting using the microfluidic apparatus of FIG. 1. A microfluidic apparatus 000' shown in FIG. 1 may include an upper substrate 10' and a lower substrate 20'. The upper substrate 10' may be disposed with a first driving electrode layer 101' and a first hydrophobic layer 102'; and the lower substrate 20' may be disposed with a second driving electrode layer 201' and a second hydrophobic layer 202'. By adjusting the electric field between the first driving electrode layer 101' of the upper substrate 10' and the second driving electrode layer 201' of the lower substrate 20', the surface tension between the surface of a droplet M' and the second driving electrode 2011' in the second driving electrode layer 201' may be changed. In such way, the contact angle between the surface of the droplet M' and the second driving electrode 2011' may be changed, and various operations and control of the droplet M' may be realized. As shown in FIG. 2, during the droplet splitting process, the first driving electrode layer 101' and the second driving electrodes 2011' at two ends of the droplet M' may be turned on until the droplet M' is split into two droplets M''. At this point, the cell thickness h' between the upper substrate 10' and the lower substrate 20' may need to be relatively small so that the droplets M' can be pinched off and split. During the merging process of the droplets, two droplets M'' may be moved to a same position to collide and merge, and the cell thickness h' between the upper substrate 10' and the lower substrate 20' may need to be relatively large, which may be beneficial for thorough merging of different droplets M''. However, the cell thickness h' between the upper substrate 10' and the lower substrate 20' in FIG. 1 has a fixed height, such that compatibility of non-stop operation and control of droplets M' of different sizes may be poor.

To solve on above-mentioned problems, the present disclosure provides a microfluidic apparatus, and its driving method and formation method, which can be compatible with driving of droplets of different sizes, realize the operation of splitting or merging various droplets, and optimize operational performance including digital microfluidic droplet generation, division, merging, and the like. The microfluidic apparatus, and its driving method and formation method are described in detail hereinafter.

Figure 4:
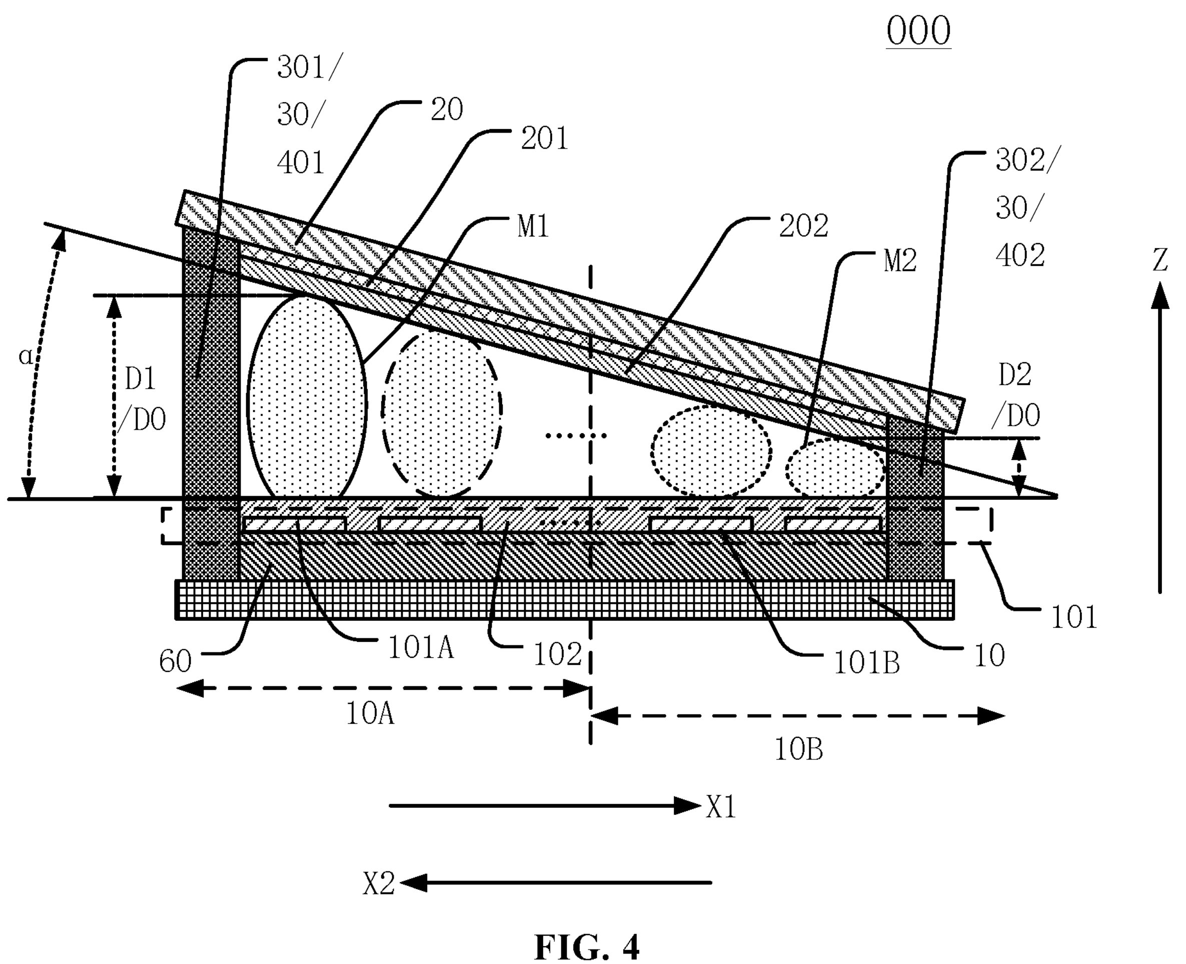
FIG. 4 illustrates a structural schematic of an exemplary microfluidic apparatus according to various embodiments of the present disclosure.

FIG. 4 illustrates a structural schematic of an exemplary microfluidic apparatus according to various embodiments of the present disclosure. A microfluidic apparatus 000 provided in one embodiment may include a first substrate 10 and a second substrate 20 which are oppositely disposed. Each of the first substrate 10 and the second substrate 20 may be a smooth substrate and/or a flat substrate; an electrode array layer 101 may be on the side of the first substrate 10 facing the second substrate 20; and a second electrode layer 201 may be on the side of the second substrate 20 facing the first substrate 10.

The electrode array layer 101 may at least include a plurality of first electrodes 101A and a plurality of second electrodes 101B.

In the direction in parallel with the plane of the first substrate 10, along the first direction X1, the first substrate 10 may include a first region 10A and a second region 10B. The first electrode 101A may be in the first region 10A, and the second electrode 101B may be in the second region 10B.

In the direction Z perpendicular to the plane of the first substrate 10, the distance between the first substrate 10 and the second substrate 20 in the first region 10A is D1, and the distance between the first substrate 10 and the second substrate 20 in the second region 10B is D2, where D1>D2.

For example, the microfluidic apparatus 000 provided in one embodiment may include the first substrate 10 and the second substrate 20 which are oppositely disposed. The first substrate 10 and the second substrate 20 may both be flat substrates. The first substrate 10 and the second substrate 20 may be rigid glass substrates, that is, the entire region of the first substrate 10 and the entire region of the second substrate 20 may be flat substrates without bent portions.

In one embodiment, the side of the first substrate 10 facing the second substrate 20 may include the electrode array layer 101; and the electrode array layer 101 may at least include the plurality of first electrodes 101A and the plurality of second electrodes 101B. Optionally, in one embodiment, the shapes and sizes of the electrodes disposed in the electrode array layer 101 may not be limited, which may only need to satisfy that in the direction in parallel with the plane of the first substrate 10, along the first direction X1, the first substrate 10 may include the first region 10A and the second region 10B, the first electrode 101A may be in the first region 10A, the second electrode 101B may be in the second region 10B, and the electrode array layer 101 may include two electrode types in different regions. Optionally, other film layers may also be between the first substrate 10 and the electrode array layer 101 in one embodiment, such as the driving layer 60 shown in FIG. 4. The driving layer 60 may be a film layer for disposing signal lines, a film layer for disposing transistor arrays, or a film layer for disposing signal lines and transistor arrays (the specific structure is not shown and can be understood with reference to the structure connected to a control circuit in the existing technology). A driving circuit for controlling the movement of the droplets in the microfluidic apparatus 000 may be electrically connected to the driving layer 60 to realize droplet driving and operation.

In one embodiment, the side of the second substrate 20 facing the first substrate 10 may further include the second electrode layer 201. Optionally, the second electrode layer 201 in one embodiment may be an entire-surface structure. The second electrode layer 201 may be connected to a ground signal, or always be connected to a negative potential signal, so that an electric field for driving droplets may be formed between the second electrode layer 201 and each electrode of the electrode array layer 101. When the electrode array layer 101 includes a plurality of blocked electrodes, the second electrode layer 201 may be a whole-surface structure in a partial region formed by the blocked electrodes of the plurality of electrode array layers 101, or may also be an entire-surface structure including a plurality of openings for the entire second substrate 20 (for convenience of illustration, the openings are not shown in FIG. 4), or may also be an entire-surface structure in the first region 10A, an entire-surface structure in the second region 10B, or may also be configured as a blocked structure corresponding to the electrode array layer 101, which may only need to satisfy that for the electrode array layer 101 in a partial region, the second electrode layer 201 may be an entire-surface structure in the partial region of the electrode array layer 101, which may not be limited in one embodiment; and may also only need to satisfy that different electric fields for controlling the droplets may be formed by applying different voltages to the second electrode layer 201 and the electrode array layer 101. As shown in FIG. 4, in one embodiment, the second electrode layer 201 may be an entire-surface structure as an example. It should be noted that when the second electrode layer 201 is an entire-surface structure, it may not need to cover the second substrate 20; on the other hand, when the second electrode layer 201 is an entire-surface structure, the second electrode layer 201 may further include hollow structures or openings.

In one embodiment, in the direction Z perpendicular to the plane of the first substrate 10, the distance between the first substrate 10 and the second substrate 20 in the first region 10A is D1, and the distance between the first substrate 10 and the second substrate 20 in the second region 10B is D2. It can be understood that, as shown in FIG. 4, in one embodiment, the distance between the first substrate 10 and the second substrate 20 can be understood as the distance between the surface of the first substrate 10 facing the side of the second substrate 20 and the surface of the second substrate 20 facing the side of the first substrate 10; and the distance between the first substrate 10 and the second substrate 20 in one embodiment can also be understood as the distance between the surface of the structure closest to the second substrate 20 among the structures on the side of the first substrate 10 facing the second substrate 20 and the surface of the structure closest to the first substrate 10 among the structures on the side of the second substrate 20 facing the first substrate 10. For the convenience of illustration, in one embodiment and following embodiments, the latter distance may indicate the distance between such two substrates. D1>D2, that is, the first substrate 10 and the second substrate 20 with the flat structure may be directly and oppositely disposed at a certain angle, which may achieve different cell thicknesses in different regions. The distance D1 between the first substrate 10 and the second substrate 20 in the first region 10A may be relatively large, and the distance D2 between the first substrate 10 and the second substrate 20 in the second region 10B may be relatively small, which may be matched with droplets of different sizes and be beneficial for different droplet operations.

When the microfluidic apparatus 000 provided in one embodiment performs the operation of splitting a large droplet into small droplets, the large droplet may be arranged on the first electrode 101A of the first region 10A, and the large droplet may move along the first direction X1 (the first direction X1 in one embodiment can be understood as the direction X1 pointing from the first region 10A to the second region 10B) by adjusting the voltage applied to the first electrode 101A in the first region 10A. After the droplet moves to the second region 10B, the distance D2 between the first substrate 10 and the second substrate 20 may be less than the distance D1 between the first substrate 10 and the second substrate 20 in the first region 10A in the second region 10B, and smaller distance D2 between the first substrate 10 and the second substrate 20 may make the large droplet (the large droplet M1 indicated by the solid line in FIG. 4) to be easily pinched off and split to form at least two small droplets (the small droplet M2 indicated by the dotted line in FIG. 4). It can be understood that the droplets indicated by the dotted lines in FIG. 4 may only indicate possible sizes of the droplets moving to such positions after being pinched off and may not indicate the number of droplets actually between the first substrate 10 and the second substrate 20.

When the microfluidic apparatus 000 provided in one embodiment performs the operation of merging at least two small droplets into a large droplet, at least two small droplets may be arranged on the second electrode 101B of the second region 10B, each droplet may move along the third direction X2 (it can be understood that, as shown in FIG. 4, the third direction X2 in one embodiment can be understood as the direction X2 pointing from the second region 10B to the first region 10A and be opposite to the direction X1 pointing from the first region 10A to the second region 10B in the direction in parallel with the plane of the first substrate 10) by adjusting the voltage applied to the second electrode 101B in the second region 10B. After moving to the first region 10A, the distance D1 between the first substrate 10 and the second substrate 20 in the first region 10A may be greater than the distance D2 between the first substrate 10 and the second substrate 20 in the second region 10B, and larger distance D1 between the first substrate 10 and the second substrate 20 may provide a larger space, which may be beneficial for desirable and adequate merging of at least two small droplets into the large droplet (the process is not shown in drawings).

In the microfluidic apparatus 000 of one embodiment, the flat first substrate 10 and the second substrate 20 may be obliquely and directly disposed to be opposite to each other at a certain angle, which may avoid using a flexible substrate to achieve different cell thicknesses resulting in increased process difficulty. In such way, the process may not only be simple, and different cell thicknesses of different regions may also be directly realized through a flat hard substrate, which may be compatible with driving droplets of different sizes, thereby realizing the operation of driving droplets of different sizes and splitting or merging droplets of different sizes and being beneficial for optimizing operational performance. Droplet merging may be realized in the position of the large cell thickness, so that the droplet merging may be more sufficient and efficient; and the droplet splitting may be realized at the position of the small cell thickness, so that the droplet splitting may be more stable and reliable.

Optionally, formation materials of the electrode array layer 101 and the second electrode layer 201 may not be limited in one embodiment, which may be transparent conductive materials such as indium tin oxide (ITO) semiconductor transparent conductive films and the like, and also be metal conductive materials (such as metal copper and the like). Such formation materials may be configured according to actual requirements in an implementation.

It can be understood that, in one embodiment, only a cross-sectional structural schematic of the microfluidic apparatus 000 may be exemplarily illustrated in FIG. 4. In an implementation, the structure of the microfluidic apparatus 000 may include, but may not be limited to, the structure shown in FIG. 4; may also include other structures, such as driving signal lines for supplying voltages to the first electrode 101A and the second electrode 101B of the electrode array layer 101, an insulation film layer, a hydrophobic layer that facilitates the movement of droplets, and the like; and may also include structures for collecting droplets and the like, which may not be described in detail herein and may refer to products of the microfluidic technology in the existing technology. In one embodiment, the angle dimension formed by the flat first substrate 10 and the flat second substrate 20 may not be limited. In an implementation, the angle may only need to satisfy that, in the direction Z perpendicular to the plane of the first substrate 10, the distance D1 between the first substrate 10 and the second substrate 20 in the first region 10A is greater than the distance D2 between the first substrate 10 and the second substrate 20 in the second region 10B.

Optionally, the side of the electrode array layer 101 facing the second substrate 20 may include a first insulation hydrophobic layer 102, and the side of the second electrode layer 201 facing the first substrate 10 may include a second insulation hydrophobic layer 202. The first insulation hydrophobic layer 102 and the second insulation hydrophobic layer 202 may be configured to insulate and isolate moisture.

It should be noted that, in one embodiment, it may not limit the voltage control manner of the electrode array layer 101 and the second electrode layer 201 during the splitting or merging process of droplets, which may include, but may not be limited to, above-mentioned embodiments. In an implementation, the voltage may be applied according to droplet operation requirements, which may not be limited in one embodiment.

It should be further noted that, in one embodiment, it may only exemplarily illustrate the number and size of the first electrodes 101A and the second electrodes 101B in the electrode array layer 10 which may not indicate actual configured number and size of electrodes. In an implementation, compatible electrode sizes may be designed according to actual droplet sizes, which may not be described in detail in one embodiment.

Optionally, referring to FIGS. 4-12, FIGS. 5-8 illustrate schematics of a process of droplet movement and splitting on an electrode array layer according to various embodiments of the present disclosure; and FIGS. 9-12 illustrate schematics of a process of droplet movement and merging on an electrode array layer according to various embodiments of the present disclosure. It can be understood that to clearly illustrate the moving process of the droplets in one embodiment, only electrodes in the electrode array layer that need to be applied with voltage during the moving process are filled with patterns and remaining floating electrodes in the electrode array layer are not filled with patterns. In one embodiment, the areas of the plurality of first electrodes 101A and the plurality of second electrodes 101B of the electrode array layer 101 may be same. That is, the area of the first electrode 101A in the first region 10A and the second electrode 101B in the second region 10B in the electrode array layer 101 may be same, thereby reducing process difficulty of the electrode array layer 101 and improving process efficiency.

Figure 5:
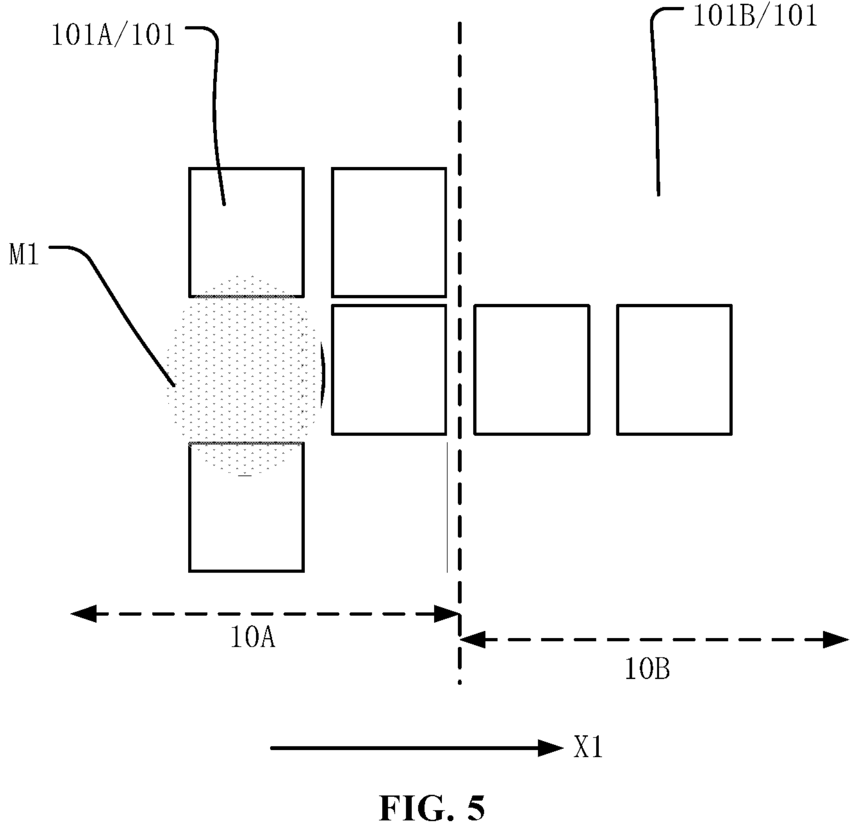
FIGS. 5-8 illustrate schematics of a process of droplet movement and splitting on an electrode array layer according to various embodiments of the present disclosure.
Figure 6:
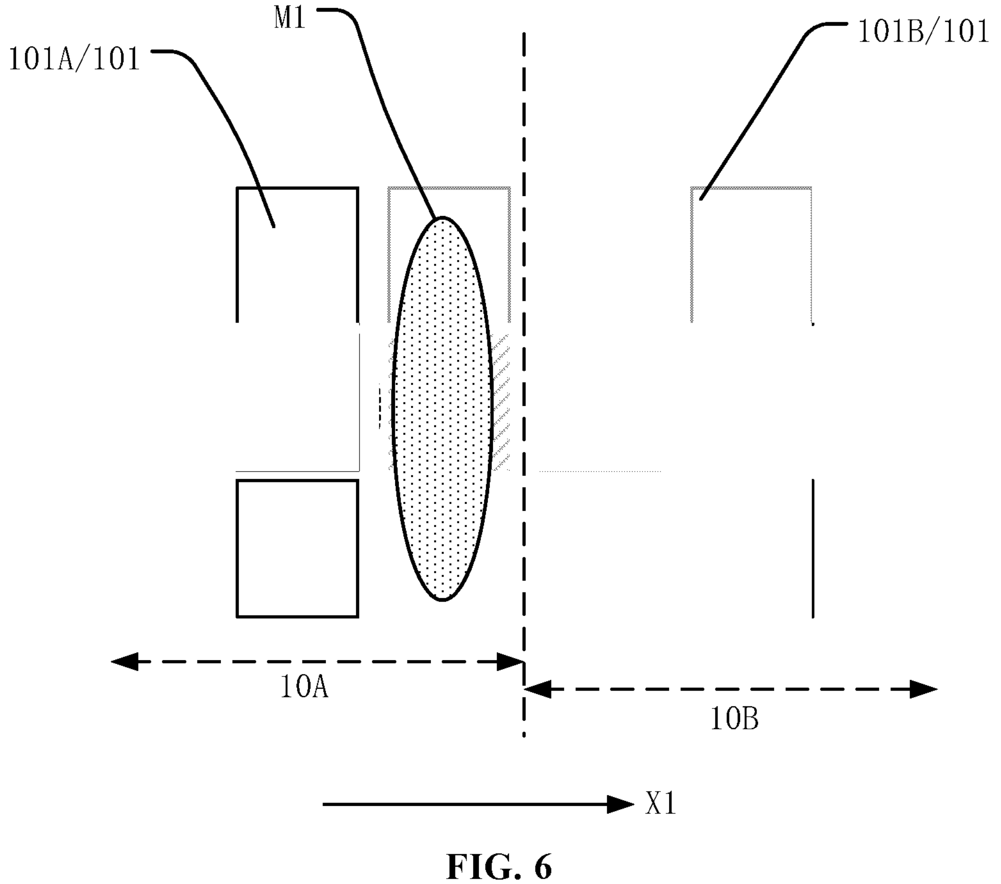
Figure 7:
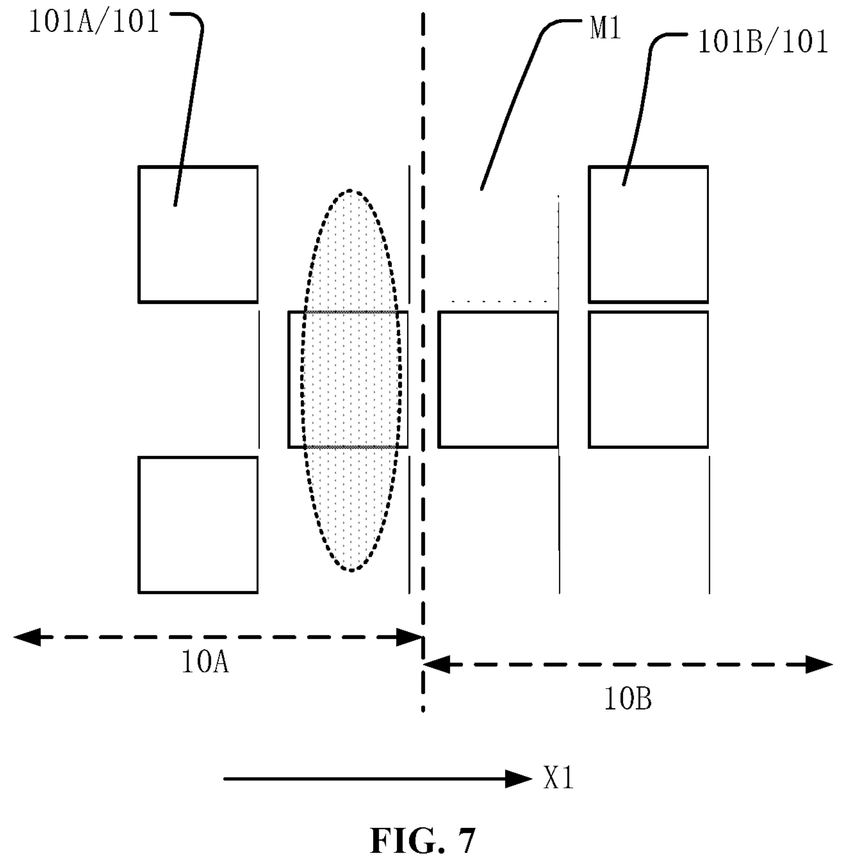
Figure 8:
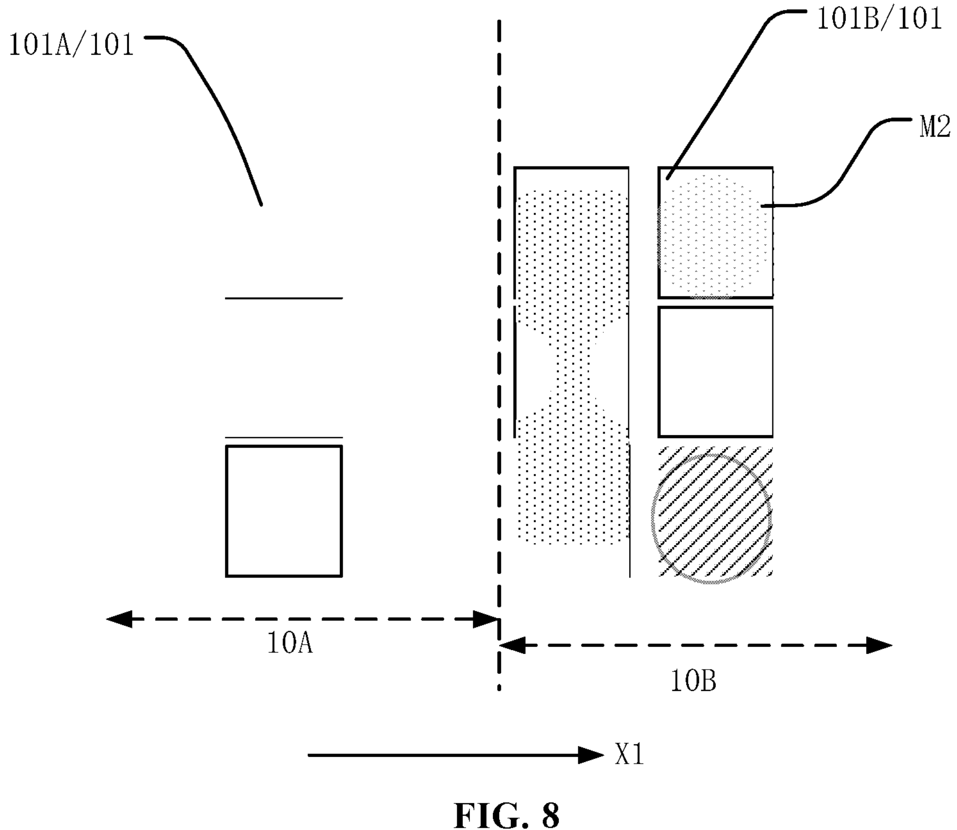

As shown in FIGS. 5-8, when the microfluidic apparatus 000 provided in one embodiment performs the operation of splitting a large droplet into small droplets, along the direction X1 pointing from the first region 10A to the second region 10B, the second electrode layer 201 may be connected to a ground signal, a driving voltage may be provided to the first electrodes 101A sequentially, and the large-sized first droplet M1 between the first substrate 10 and the second substrate 20 may move along the direction X1 pointing from the first region 10A to the second region 10B (as shown in FIG. 5) driven by the electric field formed between the first electrode 101A and the second electrode layer 201. Optionally, sequentially providing the driving voltage to the first electrodes 101A may be that the driving voltage may be sequentially provided to the plurality of first electrode groups, and each first electrode group may be simultaneously supplied with a same voltage; after the first droplet M1 moves to the plurality of first electrodes 101A adjacent to the plurality of second electrodes 101B, the first droplet M1 may be gradually elongated (as shown in FIG. 6) because the distance between the first substrate 10 and the second substrate 20 decreases; then, the driving voltage of the first electrodes 101A may be disconnected, and a driving voltage may be provided for the plurality of second electrodes 101B; one elongated first droplet M1 may continue to move to the plurality of second electrodes 101B (as shown in FIG. 7), and by selectively applying a voltage to second electrodes 101B at different positions, the large-sized first droplet M1 pinched and elongated on the plurality of second electrodes 101B may be split into a plurality of small-sized second droplets M2 (as shown in FIG. 8). In one embodiment, by setting the distance D2 between the first substrate 10 and the second substrate 20 in the second region 10B to be less than the distance D1 between the first substrate 10 and the second substrate 20 in the first region 10A, the first droplet M1 may be pinched and elongated after moving on the plurality of first electrodes 101A adjacent to the plurality of second electrodes 101B, and continue to be pinched after moving to the plurality of second electrodes 101B, thereby being easily split into a plurality of small-sized second droplets M2. The droplets indicated by the dotted lines in FIGS. 5-8 may indicate the morphology of the droplets in previous steps.

Figure 9:
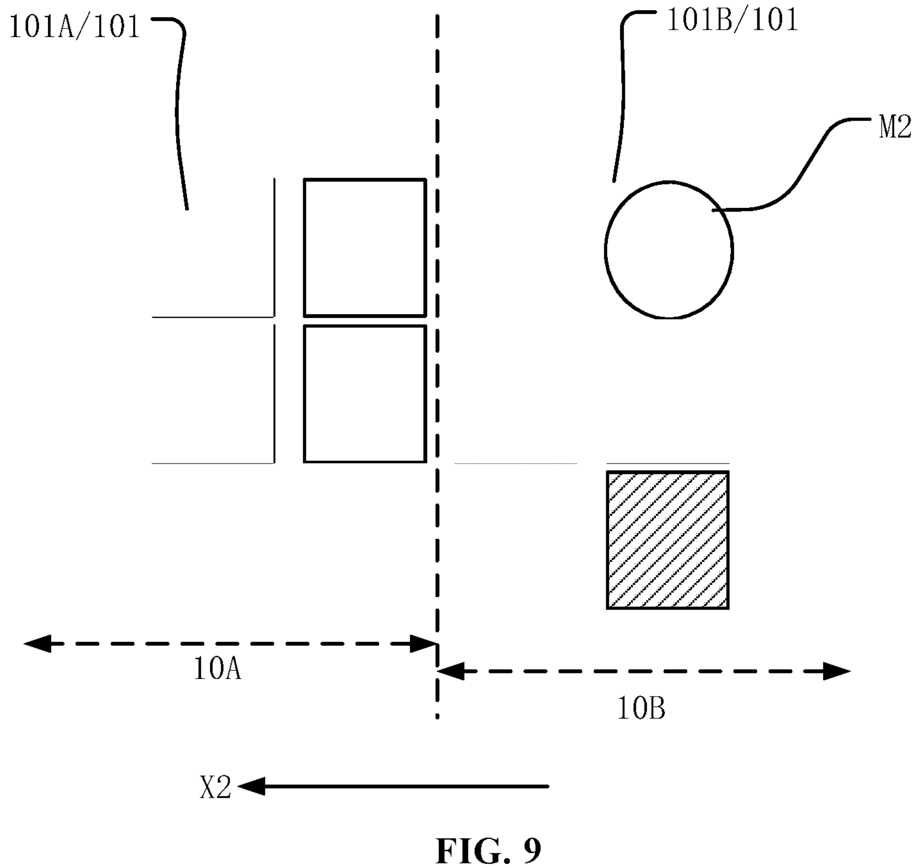
FIGS. 9-12 illustrate schematics of a process of droplet movement and merging on an electrode array layer according to various embodiments of the present disclosure.
Figure 10:
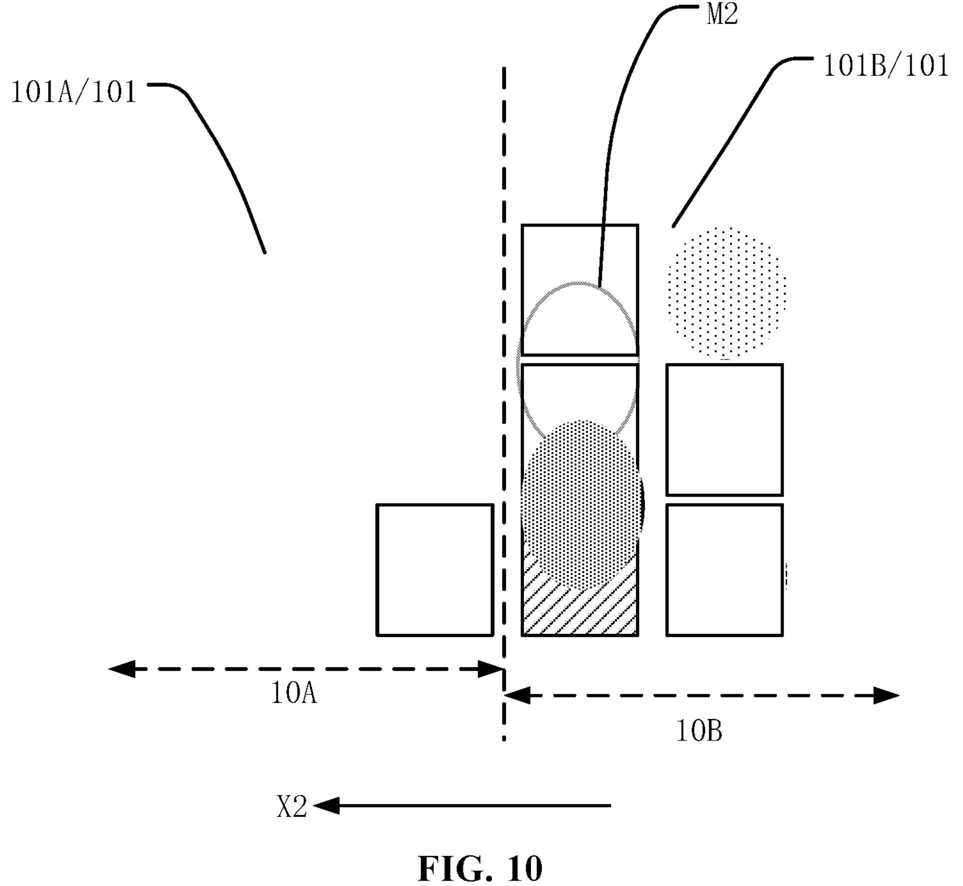
Figure 11:
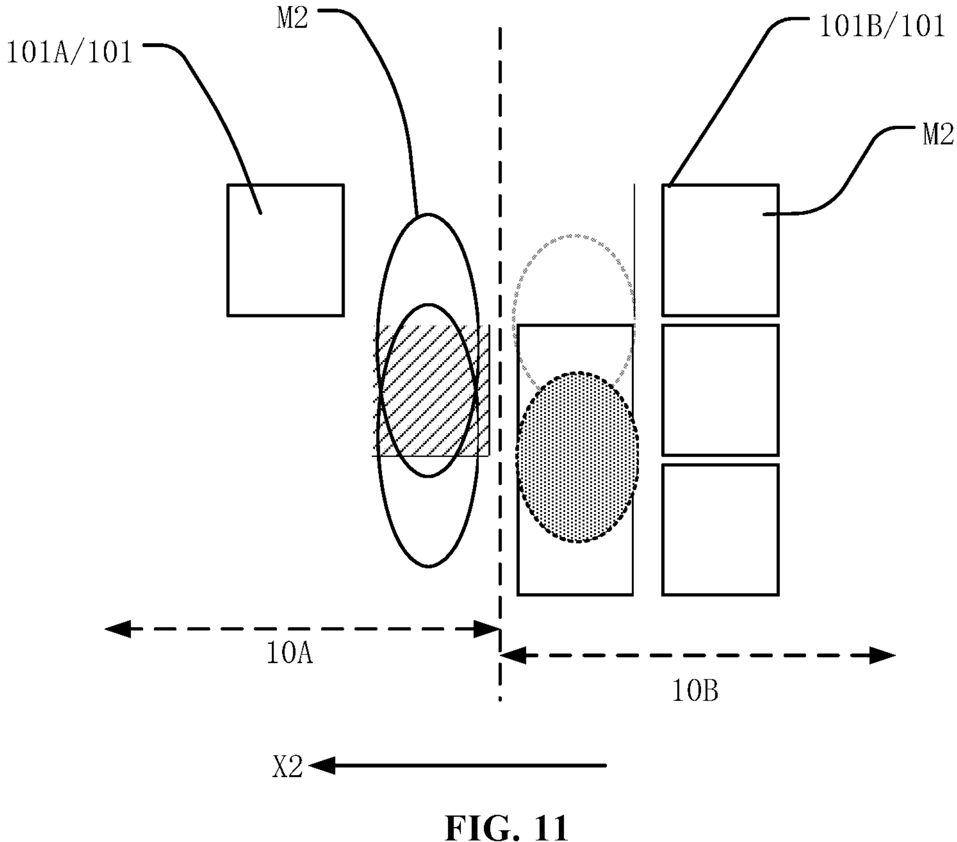
Figure 12:
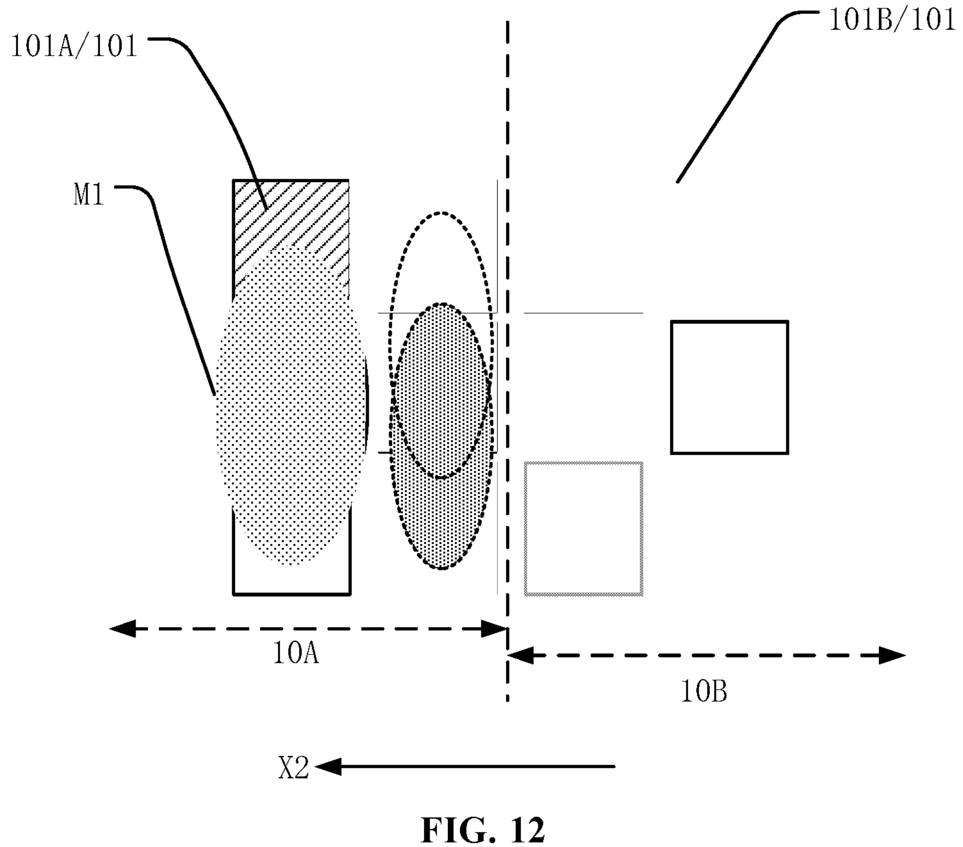

As shown in FIGS. 9-12, when the microfluidic apparatus 000 provided in one embodiment performs the operation of merging at least two small droplets into a large droplet, along the third direction X2 (the direction pointing from the second region 10B to the first region 10A), the second electrode layer 201 may be connected to a ground signal, a driving voltage may be provided to the second electrodes 101B sequentially, and the plurality of small-sized second droplets M2 between the first substrate 10 and the second substrate 20 may move along the direction X2 pointing from the second region 10B to the first region 10A (as shown in FIG. 9) driven by the electric field formed between the second electrode 101B and the second electrode layer 201. After the plurality of small-sized second droplets M2 move to the plurality of second electrodes 101B adjacent to the plurality of first electrodes 101A (as shown in FIG. 10), the driving voltage of the second electrode 101B may be disconnected, the driving voltage may be provided to the plurality of first electrodes 101A adjacent to the plurality of second electrodes 101B, and the plurality of small-sized second droplets M2 may move onto the plurality of first electrodes 101A (as shown in FIG. 11). Since the distance D1 between the first substrate 10 and the second substrate 20 in the first region 10A is relatively large, the plurality of small-sized second droplets M2 may slowly aggregate to form one large-sized first droplet M1 on the plurality of first electrodes 101A (as shown in FIG. 12). In one embodiment, by setting the distance D1 between the first substrate 10 and the second substrate 20 in the first region 10A to be greater than the distance D2 between the first substrate 10 and the second substrate 20 in the second region 10B, the plurality of small-sized second droplets M2 may slowly merge after moving to the plurality of second electrodes 101B adjacent to the plurality of first electrodes 101A, and continue to move to the plurality of first electrodes 101A. Due to relatively large distance D1 between the first substrate 10 and the second substrate 20 in the first region 10A, sufficient space may be provided for more thorough merging, thereby achieving desirable droplet merging effect. The second droplets M2 at different positions in FIG. 9 may be droplets with different components or component contents; and to match droplets with different components or component contents, multiple liquid inlets may be disposed in embodiments of the present disclosure.

Optionally, referring to FIG. 4, in one embodiment, along the first direction X1, the distance D0 between the first substrate 10 and the second substrate 20 may gradually decrease in the direction Z perpendicular to the plane of the first substrate 10.

In one embodiment, it describes that when the first substrate 10 and the second substrate 20 are both flat and rigid substrates, two substrates may be oppositely disposed to form droplet channels with different heights in different regions; and along the first direction X1, the distance D0 between the first substrate 10 and the second substrate 20 in the direction Z perpendicular to the plane of the first substrate 10 may gradually decrease. Therefore, in the process of making the droplets move along the first direction X1 and the third direction X2 (the direction X1 is pointing from the first region 10A to the second region 10B, and the direction X2 is pointing from the second region 10B to the first region 10A), small droplets may be merged into large droplets with sufficient height space, and large droplets may be pinched off and split into small droplets with gradually narrowing space between two substrates. Furthermore, it may realize that one microfluidic apparatus may be compatible with driving droplets of different sizes and may perform various operations of driving, splitting or merging droplets of different sizes with high flexibility.

Optionally, referring to FIG. 4, in one embodiment, the first substrate 10 and the second substrate 20 may form an angle $\alpha$, where $10° \leq \alpha \leq 30°$.

In one embodiment, it describes that when the first substrate 10 and the second substrate 20, which are both flat structures, are directly disposed opposite to each other to form the angle $\alpha$ of a certain value to achieve different cell thicknesses in different regions, the range of the angle $\alpha$ may be $10° \leq \alpha \leq 30°$. For example, the angle $\alpha$ may be 15°, 20°, 25°, and the like. Therefore, the distance D1 between the first substrate 10 and the second substrate 20 in the first region 10A may be avoided from being excessively large when the angle $\alpha$ is excessively large. Excessively large space may result in that the space size between the first substrate 10 and the second substrate 20 may change too slowly, and the changing process of the droplet may be too slow, which may make the effect of droplet splitting and merging not obvious, thereby affecting the use effect. It may also avoid that the space size between the first substrate 10 and the second substrate 20 may change too quickly when the angle α is excessively small, and the movable range of the droplet in the second region 10B may be excessively small which may affect the use. Therefore, in one embodiment, the angle α formed by the first substrate 10 and the second substrate 20 may be set to $10°≤α≤30°$, which may realize that a same microfluidic apparatus 000 may be compatible for droplet splitting and merging, and the effect of controlling droplets may be improved by setting the value of the angle α.

Figure 13:
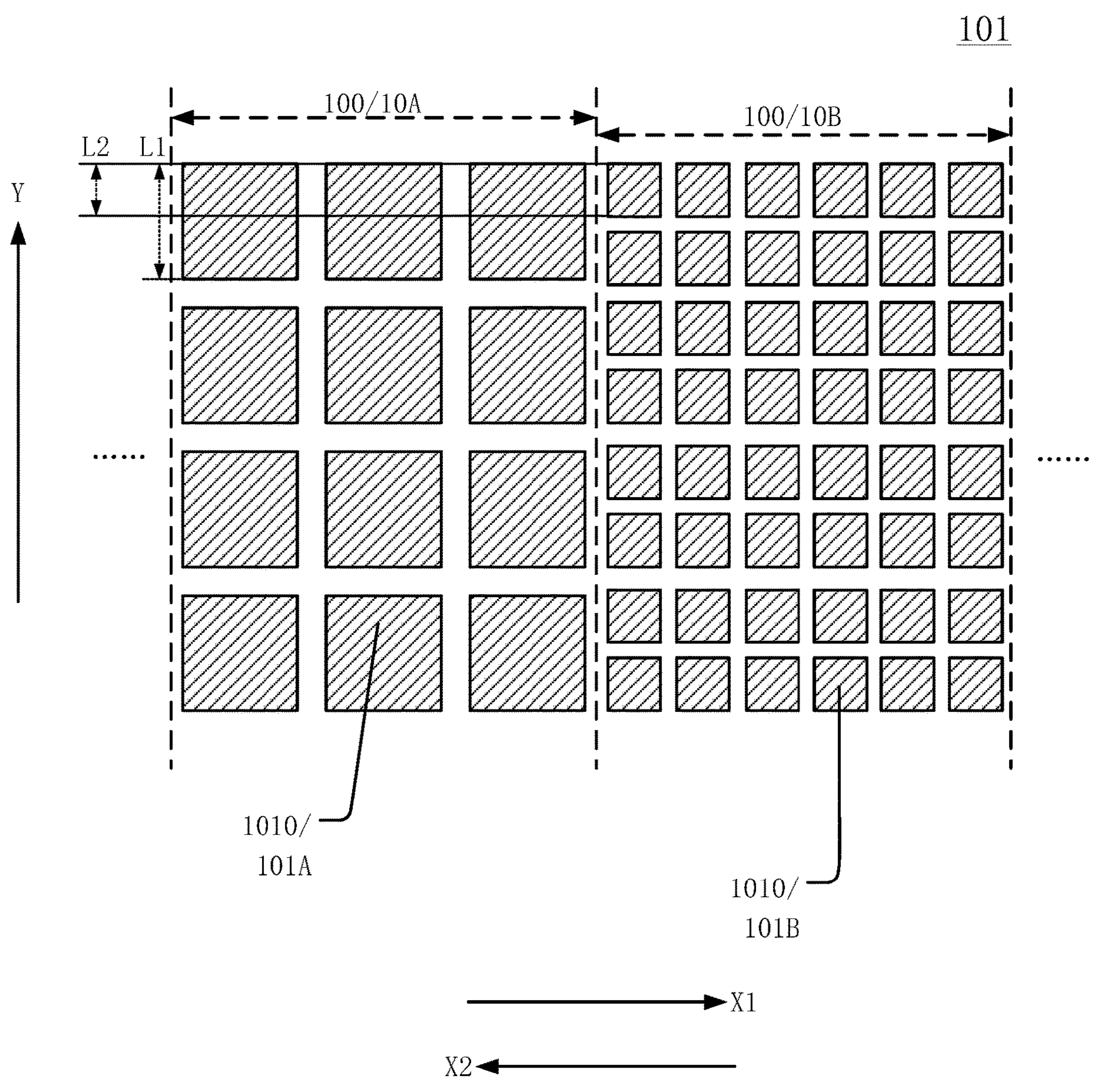
FIG. 13 illustrates a planar structural schematic of an electrode array layer on a first substrate in FIG. 4.

In some optional embodiments, referring to FIGS. 4 and 13, FIG. 13 illustrates a planar structural schematic of the electrode array layer on the first substrate in FIG. 4. In one embodiment, the electrode array layer 101 may include a plurality of electrodes 1010; along the first direction X1, the first substrate 10 may include a plurality of sub-regions 100; and the orthographic projection areas of the electrodes 1010 of different sub-regions 100 on the first substrate 10 may be different.

Along the first direction X1, the orthographic projection areas of the electrodes 1010 of all sub-regions 100 on the first substrate 10 may gradually decrease.

In one embodiment, it describes that the sizes of the plurality of electrodes 1010 disposed in the electrode array layer 101 may be different. For example, the areas of the first electrodes 101A in the first region 10A and the second electrodes 101B in the second region 10B may be different. In one embodiment, the electrode array layer 101 may include the plurality of electrodes 1010; along the first direction X1, the first substrate 10 may include the plurality of sub-regions 100; and the orthographic projection areas of the electrodes 1010 in different sub-regions 100 on the first substrate 10 may be different. For example, along the first direction X1, the orthographic projection areas of the electrodes 1010 of all sub-regions 100 on the first substrate 10 may gradually decrease. That is, the orthographic projection area of the first electrode 101A in the first region 10A on the first substrate 10 may be relatively large, and the orthographic projection area of the second electrode 101B in the second region 10B on the first substrate 10 may be relatively small. If there is another sub-region 100 on the side of the second region 10B away from the first region 10A, the orthographic projection area of the electrode 1010 in such sub-region 100 may continue to be reduced, which may realize that along the first direction X1, the orthographic projection areas of the electrodes 1010 of all sub-regions 100 on the first substrate 10 may gradually decrease. In such way, the area sizes of the electrodes 1010 of different sub-regions 100 on the first substrate 10 may be proportional to distances between the first substrate 10 and the second substrate 20. That is, the greater the distance between the first substrate 10 and the second substrate 20 in the direction Z perpendicular to the plane of the first substrate 10 is, the greater the orthographic projection area of the electrode 1010 of the sub-region 100 on the first substrate 10 is; and the smaller the distance between the first substrate 10 and the second substrate 20 in the direction Z perpendicular to the plane of the first substrate 10 is, the smaller the orthographic projection area of the electrode 1010 of the sub-region 100 on the first substrate 10 is. In one embodiment, the first substrate 10 and the second substrate 20 may be attached at a certain angle. While realizing gradient change of the cell thickness, according to the gradient change of cell thickness, the electrode 1010 with relatively large area may be designed at a position with a large cell thickness, and the electrode 1010 with relatively small area may be designed at a position with a small cell thickness; such that the cell thickness (that is, the distance D0 between the first substrate 10 and the second substrate 20) may be matched with the sizes of the electrodes 1010 in the sub-region 100 (it can be understood that FIGS. 4 and 13 in one embodiment are only exemplary and do not indicate actual sizes and distribution manners of the electrodes 1010). Furthermore, the operation of droplets of different sizes may be realized in the regions where different sub-regions 100 are located, large-sized droplets may be located on electrodes 1010 with large areas in relatively large cell thickness, and small-sized droplets may be located on electrodes 1010 with small areas in relatively small cell thickness. By reasonably allocating electrodes 1010 of different areas in different sub-regions 100 to adapt to droplet sizes in different regions, the droplet manipulation flexibility may be higher.

It should be noted that, in one embodiment, it may exemplarily illustrate the shapes, sizes and arrangement manners of the electrodes 1010 in all sub-regions 100. In an implementation, the number of sub-regions 100 and the number, shapes and arrangement manners of electrodes 1010 may include, but may not be limited to, above-mentioned implementation manners, and may include other implementation manners, which may only need to satisfy that along the first direction X1, the orthographic projection areas of the electrodes 1010 of all sub-regions 100 on the first substrate 10 may gradually decrease and may not be described in detail herein.

Optionally, as shown in FIGS. 4 and 13, in one embodiment, the orthographic projection areas of the electrodes 1010 of one sub-region 100 on the first substrate 10 may be same. In one embodiment, it describes that along the first direction X1, the orthographic projection areas of the electrodes 1010 of all sub-regions 100 on the first substrate 10 may be different and gradually decrease but the orthographic projection areas of the electrodes 1010 of one sub-region 100 on the first substrate 10 may be set to be same. Therefore, the areas of the electrodes 1010 may be gradually changed in different regions, which may be beneficial for reducing formation difficulty of the electrodes 1010 and improve process efficiency.

Figure 14:
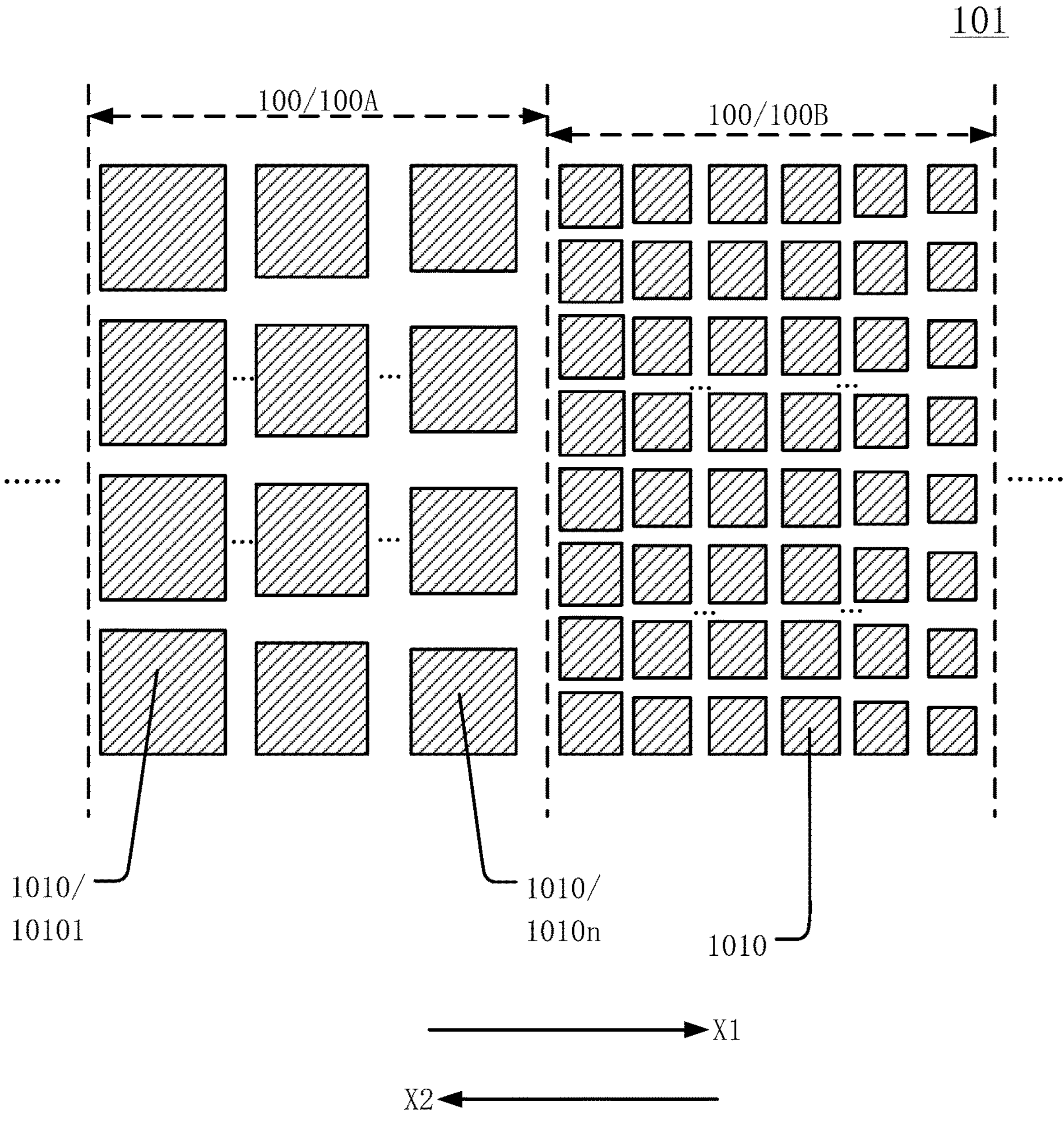
FIG. 14 illustrates another planar structural schematic of an electrode array layer on a first substrate in FIG. 4.

Optionally, referring to FIGS. 4 and 14, FIG. 14 illustrates another planar structural schematic of the electrode array layer on the first substrate in FIG. 4. The orthographic projection areas of the electrodes 1010 of one sub-region 100 on the first substrate 10 may be different; and along the first direction X1, the orthographic projection areas of the electrodes 1010 of one sub-region 100 on the first substrate 10 may gradually decrease. In one embodiment, it further describes that, along the first direction X1, while the orthographic projection areas of the electrodes 1010 of all sub-regions 100 on the first substrate 10 are different and gradually decrease, the orthographic projection areas of the electrodes 1010 of one sub-region 100 on the first substrate 10 may also be configured to gradually decrease along the first direction X1. In the sub-region 100A shown in FIG. 14, along the first direction X1, the orthographic projection area of the first electrode 1010*n*, which is closest to the sub-region 100B, on the first substrate 10 may be the smallest in the sub-region 100A, and the orthographic projection area of the first electrode 10101, which is farthest from the sub-region 100B, on the first substrate 10 may be the largest in the sub-region 100A. Along the first direction X1, the distance D0 between the first substrate 10 and the second substrate 20 in the direction Z perpendicular to the plane of the first substrate 10 gradually decreases; therefore, the area of the electrode 1010 of the electrode array layer 101 may be configured to also be proportionally reduced with the distance D0 between the first substrate 10 and the second substrate 20 in the direction Z perpendicular to the plane of the first substrate 10, which may be beneficial for improving droplet changing effect.

In some optional embodiments, referring to FIGS. 4 and 13, the electrodes 1010 in the electrode array layer 101 may include a plurality of first electrodes 101A in the first region 10A (one sub-region 100) and a plurality of second electrodes 101B in the second region 10B (another sub-region 100). The orthographic projection area of the first electrode 101A on the first substrate 10 may be greater than the orthographic projection area of the second electrode 101B on the first substrate 10.

In one embodiment, it describes that the electrode array layer 101 may have electrodes of different areas arranged in different regions, and the region division is that the first region 10A and the second region 10B in above-mentioned embodiment may be taken as an example for the region division. The first region 10A may be a sub-region 100, the second region 10B may be another sub-region 100, and the electrodes 1010 in the electrode array layer 101 may include the plurality of first electrodes 101A in the first region 10A (one sub-region 100) and the plurality of second electrodes 101B in the second region 10B (another sub-region 100). The orthographic projection areas of the electrodes 1010 in different sub-regions 100 on the first substrate 10 may be different. That is, the orthographic projection area of the first electrode 101A on the first substrate 10 may be greater than the orthographic projection area of the second electrode 101B on the first substrate 10. Furthermore, the operations of droplets of different sizes may be realized in the regions where the first region 10A and the second region 10B are located. Large-sized droplets may be located on large-area electrodes 1010 in relatively large cell thickness of the first region 10A, and small-sized droplets may be located on small-area electrodes 1010 in relatively small cell thickness of the second region 10B. By reasonably allocating electrodes 1010 of different areas in different sub-regions 100 to adapt to the droplet sizes in different regions, the droplet manipulation flexibility may be higher.

In some optional embodiments, referring to FIGS. 4 and 13, the length L1 of the first electrode 101A may be greater than the length L2 of the second electrode 101B along the second direction Y, where the first direction X1 may intersect the second direction Y along the direction in parallel with the plane of the first substrate 10. Optionally, in one embodiment, the first direction X1 and the second direction Y may be perpendicular to each other along the direction in parallel with the plane of the first substrate 10 as an example for illustration.

In one embodiment, it describes that the lengths of the first electrodes 101A and the second electrodes 101B of different sub-regions 100 along the second direction Y may be different; and the first direction X1 and the second direction Y may be perpendicular to or intersect with each other along the direction in parallel with the plane of the first substrate 10. For example, along the second direction Y, the length L1 of the first electrode 101A may be greater than the length L2 of the second electrode 101B. That is, the length L1 of the first electrode 101A in relatively large cell thickness of the first region 10A along the second direction Y may be relatively large, and the length L2 of the second electrode 101B along the second direction Y in relatively small cell thickness of the second region 10B may be relatively small. Therefore, when the droplets move along the direction X1 from the first region 10A to the second region 10B for droplet splitting operation, large droplets on the first electrode 101A with relatively long length L1 may be better elongated, and after moving to the second electrode 101B with relatively short length L2, the splitting operation may be desirably performed. In addition, when the droplets move along the direction X2 pointing from the second region 10B to the first region 10A to perform droplet merging operation, a plurality of small droplets on the second electrode 101B with relatively short length L2 may be better aggregated at the position of one first electrode 101A with relatively long length L1, such that it may be beneficial for the droplets to be merged desirably after moving to the first electrode 101A with relatively long length L1.

Figure 15:
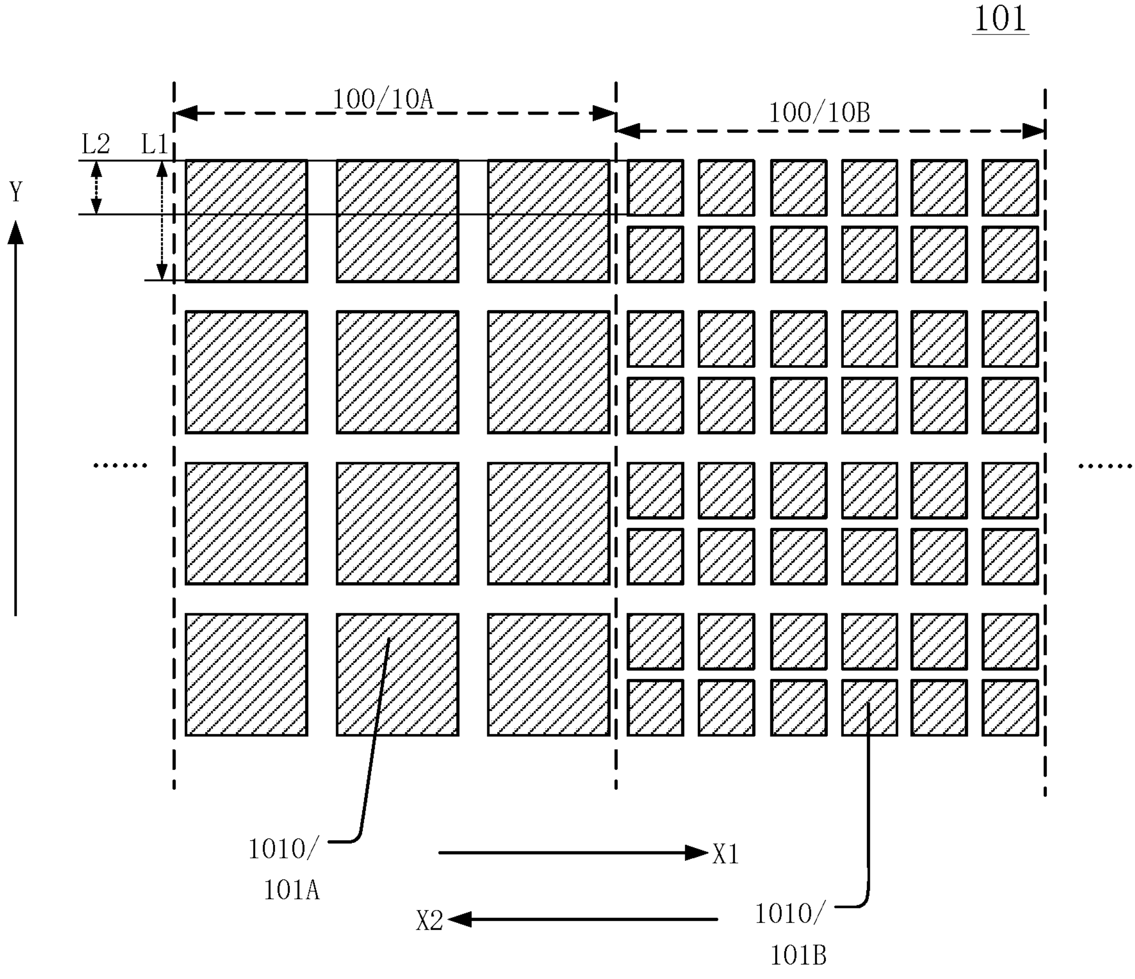
FIG. 15 illustrates another planar structural schematic of an electrode array layer on a first substrate in FIG. 4.

In some optional embodiments, referring to FIGS. 4, 13 and 15, FIG. 15 illustrates another planar structural schematic of the electrode array layer on the first substrate in FIG. 4. In one embodiment, along the second direction Y, the length of the first electrode 101A is L1, the length of the second electrode 101B is L2, L1=m×L2, and m is an integer greater than 1. Optionally, the projection of one first electrode 101A along the first direction X1 may overlap the projections of the number m of second electrodes 101B along the first direction X1. Furthermore, optionally, as shown in FIG. 15, the projection of one first electrode 101A along the first direction X1 may exactly cover the projections of the number m of second electrodes 101B along the first direction X1.

In one embodiment, it describes that when the lengths of the first electrodes 101A and the second electrodes 101B of different sub-regions 100 along the second direction Y are different, the length L1 of the first electrode 101A may be configured to be m times the length L2 of the second electrode 101B along the second direction, where m is an integer greater than 1. That is, along the second direction Y, the length L1 of the first electrode 101A may be an integral multiple of the length L2 of the second electrode 101B. As shown in FIG. 15, the length L1 of the first electrode 101A in the first region 10A may be twice the length L2 of the second electrode 101B in the second region 10B. Therefore, when the droplets move along the direction X1 pointing from the first region 10A to the second region 10B to perform droplet splitting operation, a large droplet on the first electrode 101A may be elongated and better split into an integer number of small droplets after moving to the second electrode 101B of length L2, which may be beneficial for improving uniformity of split droplets. In addition, when the droplets move along the direction X2 pointing from the second region 10B to the first region 10A to perform droplet merging operation, the droplets on the plurality of second electrodes 101B may be desirably aggregated on one first electrode 101A with the length L1, thereby optimizing droplet operation flexibility.

It can be understood that, in FIG. 15 of one embodiment, along the second direction Y, the length L1 of the first electrode 101A in the first region 10A may be twice the length L2 of the second electrode 101B in the second region 10B as an example for illustration. During an implementation, the setting of m may include, but may not be limited to, above-mentioned number, and may also be 3 or 4 or other positive integers, which may not be described in detail in one embodiment.

Figure 16:
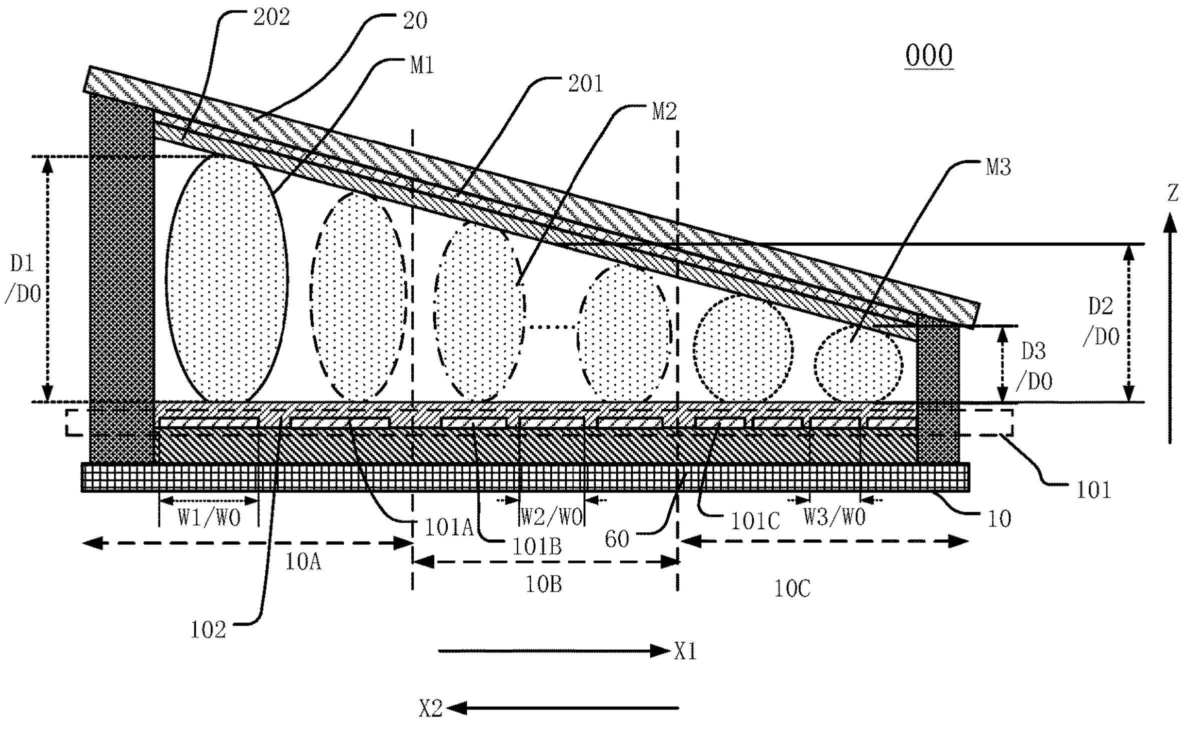
FIG. 16 illustrates another structural schematic of an exemplary microfluidic apparatus according to various embodiments of the present disclosure.
Figure 17:
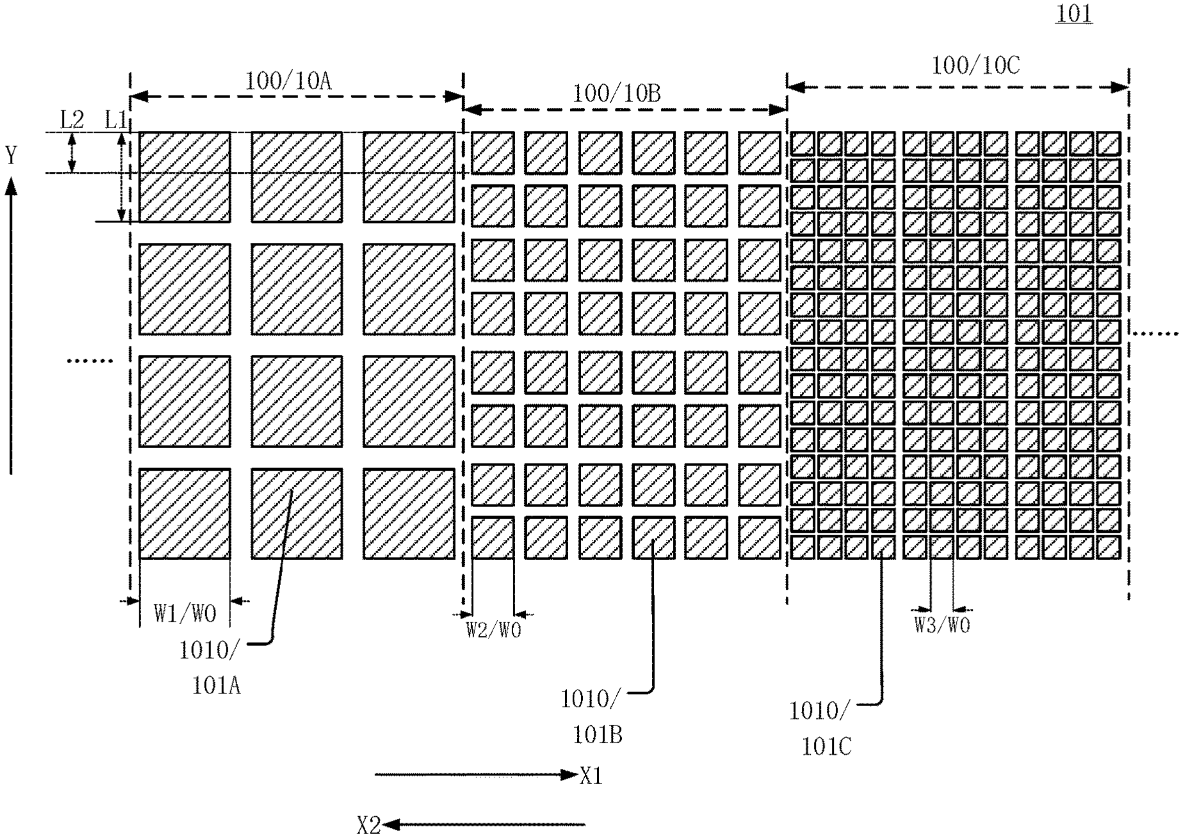
FIG. 17 illustrates a planar structural schematic of an electrode array layer on a first substrate in FIG. 16.

In some optional embodiments, referring to FIGS. 16-17, FIG. 16 illustrates another structural schematic of an exemplary microfluidic apparatus according to various embodiments of the present disclosure; and FIG. 17 illustrates a planar structural schematic of an electrode array layer on a first substrate in FIG. 16. In one embodiment, along the first direction X1, the first substrate 10 may further include a third region 10C; and the third region 10C may be on the side of the second region 10B away from the first region 10A. Optionally, the distance D3 between the first substrate 10 and the second substrate 20 in the third region 10C may be less than the distance D2 between the first substrate 10 and the second substrate 20 in the second region 10B.

The electrode array layer 101 in the third region 10C may include third electrodes 101C; the orthographic projection area of the first electrode 101A on the first substrate 10 may be greater than the orthographic projection area of the second electrode 101B on the first substrate 10; and the orthographic projection area of the third electrode 101C on the first substrate 10 may be less than the orthographic projection area of the second electrode 101B on the first substrate 10.

In one embodiment, it describes that the sizes of the electrodes 1010 disposed in the electrode array layer 101 may be different. For example, the areas of the first electrode 101A in the first region 10A, the second electrode 101B in the second region 10B, and the third electrode 101C in the third region 10C may be different. For example, the electrode array layer 101 may include the plurality of electrodes 1010; along the first direction X1, the first substrate 10 may include the plurality of sub-regions 100; and the orthographic projection areas of the electrodes 1010 of different sub-regions 100 on the first substrate 10 may be different. For example, along the first direction X1, the orthographic projection areas of the electrodes 1010 of all sub-regions 100 on the first substrate 10 may gradually decrease. That is, the orthographic projection area of the first electrode 101A in the first region 10A on the first substrate 10 may be relatively large, the orthographic projection area of the third electrode 101C in the third region 10C on the first substrate 10 may be relatively small, and the orthographic projection area of the second electrode 101B in the second region 10B on the first substrate 10 may be between above-mentioned two areas. It may realize that along the first direction X1, the orthographic projection areas of the electrodes 1010 of all sub-regions 100 on the first substrate 10 may gradually decrease. In such way, the area sizes of the electrodes 1010 of different sub-regions 100 on the first substrate 10 may be proportional to distances between the first substrate 10 and the second substrate 20. That is, the greater the distance between the first substrate 10 and the second substrate 20 in the direction Z perpendicular to the plane of the first substrate 10 is, the greater the orthographic projection area of the electrode 1010 of the sub-region 100 on the first substrate 10 is; and the smaller the distance between the first substrate 10 and the second substrate 20 in the direction Z perpendicular to the plane of the first substrate 10 is, the smaller the orthographic projection area of the electrode 1010 of the sub-region 100 on the first substrate 10 is. In one embodiment, the first substrate 10 and the second substrate 20 may be attached at a certain angle. While realizing gradient change of the cell thickness, according to the gradient change of cell thickness, the electrode 1010 with relatively large area may be designed at a position with a large cell thickness, and the electrode 1010 with relatively small area may be designed at a position with a small cell thickness; such that the cell thickness (that is, the distance D0 between the first substrate 10 and the second substrate 20) may be matched with the sizes of the electrodes 1010 in the sub-region 100 (it can be understood that FIGS. 4 and 13 in one embodiment are only exemplary and do not indicate actual sizes and distribution manners of the electrodes 1010). Furthermore, the operation of droplets of different sizes may be realized in the regions where different sub-regions 100 are located, large-sized droplets may be located on electrodes 1010 with large areas in relatively large cell thickness, and small-sized droplets may be located on electrodes 1010 with small areas in relatively small cell thickness. By reasonably allocating electrodes 1010 of different areas in different sub-regions 100 to adapt to droplet sizes in different regions, the droplet manipulation flexibility may be higher.

It can be understood that, in one embodiment, it may exemplarily illustrate that along the first direction X1, the sub-region 100 of the first substrate 10 may at least include the first region 10A, the second region 10B and the third region 10C. During an implementation, the number of sub-regions 100 may include, but may not be limited to, above number of sub-regions 100 and may also include the number of other sub-regions 100, which may not be limited in one embodiment.

Figure 18:
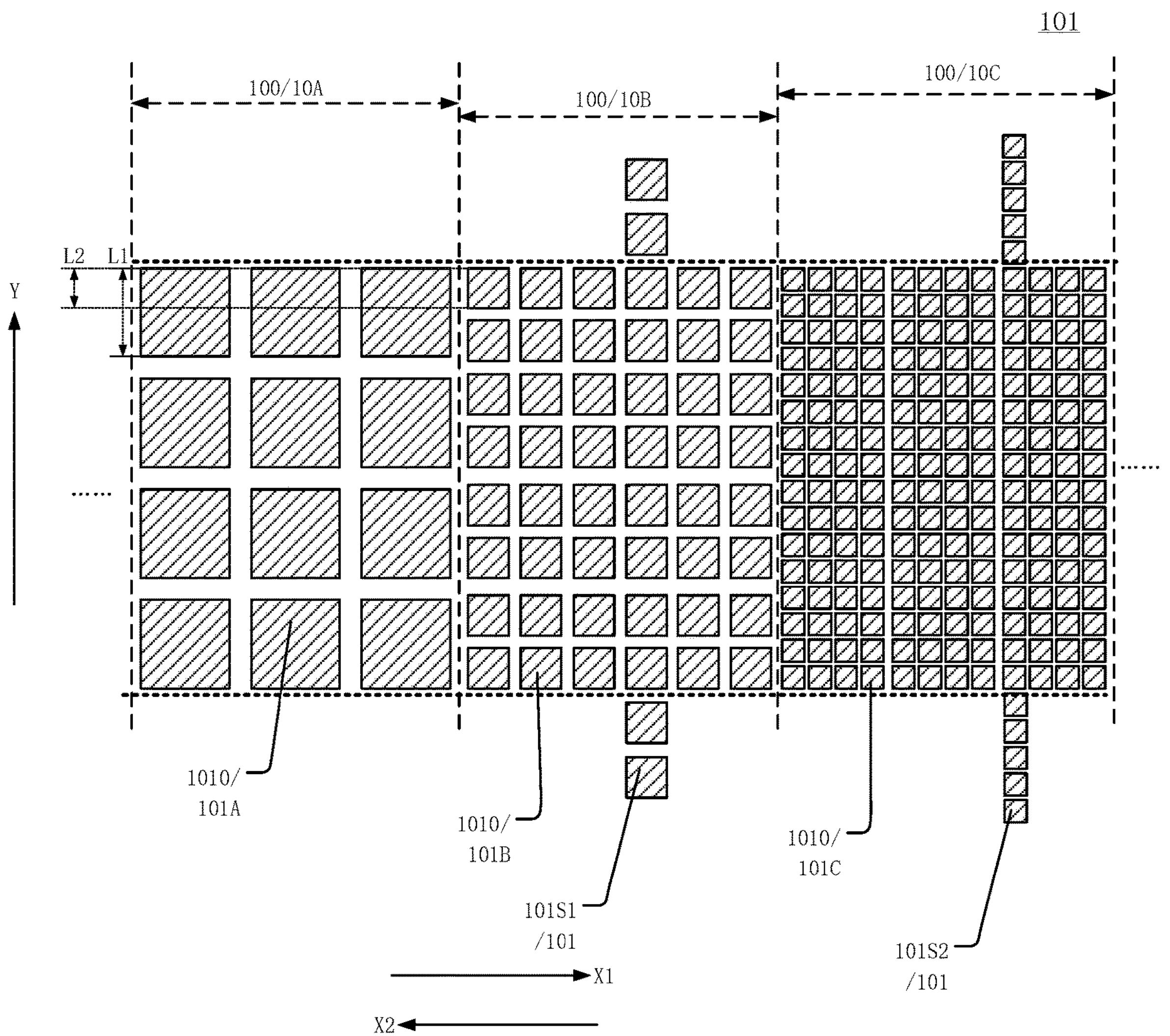
FIG. 18 illustrates another planar structural schematic of an electrode array layer on a first substrate in FIG. 16.

In some optional embodiments, referring to FIGS. 16 and 18, FIG. 18 illustrates another planar structural schematic of the electrode array layer on the first substrate in FIG. 16. In one embodiment, the electrode array layer 101 of the second region 10B may include one or more first collection electrodes 101S1; and along the second direction Y, the one or more first collection electrodes 101S1 may be on at least one side of the second electrode 101B.

The electrode array layer 101 of the third region 10C may include one or more second collection electrodes 101S2; and along the second direction Y, the one or more second collection electrodes 101S2 may be on at least one side of the third electrode 101C.

The first direction X1 may intersect the second direction Y along the direction in parallel with the plane of the first substrate 10. Optionally, in one embodiment, the first direction X1 and the second direction Y may be perpendicular to each other along the direction in parallel with the plane of the first substrate 10 as an example for illustration.

In one embodiment, it describes that the electrode array layer 101 on the first substrate 10 may also be disposed with collection electrodes. Optionally, the collection electrode may be connected to an external device for collecting droplets (not shown in FIGS. 16 and 18), which may realize the collection and packaging of droplets after the microfluidic apparatus 000 completes droplet splitting or merging operation. In one embodiment, the electrode array layer 101 of the second region 10B may include the first collection electrodes 101S1; and along the second direction Y, the first collection electrodes 101S1 may be on at least one side of the second electrode 101B. Optionally, in FIG. 18 of one embodiment, two first collection electrodes 101S1 may be on two sides of the second electrode 101B respectively as an example for illustration. The electrode array layer 101 in the third region 10C may include the second collection electrodes 101S2; and along the second direction Y, the second collection electrodes 101S2 may be on at least one side of the third electrode 101C. Optionally, in FIG. 18 of one embodiment, two second collection electrodes 101S2 may be on two sides of the third electrode 101C respectively as an example for illustration. When the droplets move along the direction X1 pointing from the first region 10A to the second region 10B to perform droplet splitting operation, the first droplet M1 on one first electrode 101A may be elongated, such that after moving to the second electrodes 101B of length L2, the droplet may be desirably split into an integer number of second droplets M2 (the size of the second droplet M2 is smaller than the size of the first droplet M1). The second droplets M2 may directly move to the first collection electrodes 101S1 on at least one side of the second electrode 101B along the second direction Y to be screened and collected and may flow into an external second droplet collection apparatus. Or, the second droplets M2 may continue to move to the third electrodes 101C in the third region 10C, and be further split into third droplets M3 (the size of the third droplet M3 is smaller than the size of the second droplet M2), and finally, the plurality of third droplets M3 may be screened and collected by the second collection electrodes 101S2 on at least one side of the third electrode 101C along the second direction Y and may flow into an external third droplet collection apparatus, thereby completing the splitting and screening process of droplets of different sizes.

Figure 19:
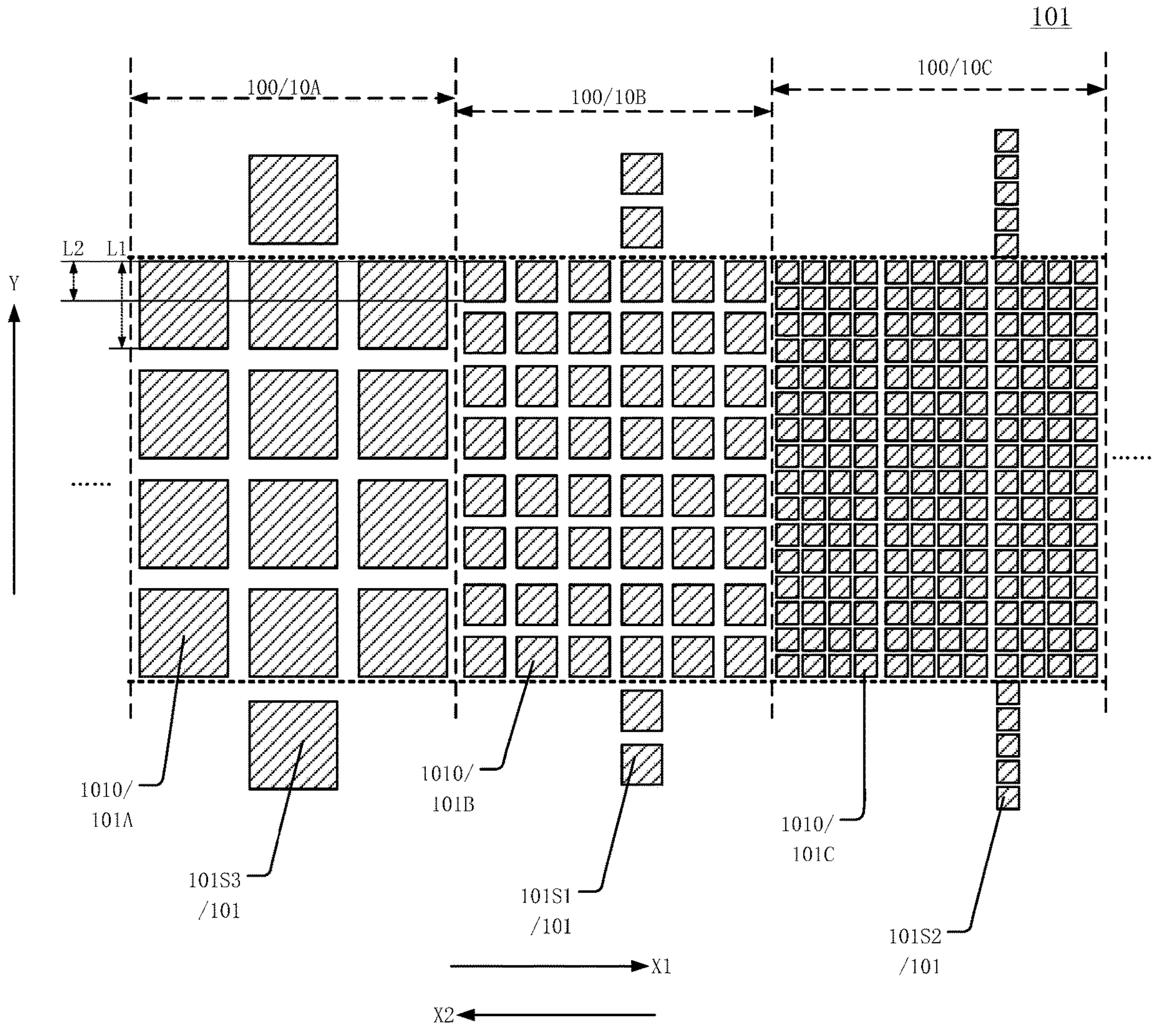
FIG. 19 illustrates another planar structural schematic of an electrode array layer on a first substrate in FIG. 16.

Optionally, referring to FIGS. 16 and 19, FIG. 19 illustrates another planar structural schematic of the electrode array layer on the first substrate in FIG. 16. In one embodiment, the electrode array layer 101 in the first region 10A may further include one or more third collection electrodes 101S3; and along the second direction Y, the one or more third collection electrodes 101S3 may be on at least one side of the first electrode 101A.

In one embodiment, it describes that the electrode array layer 101 in the first region 10A may also include the third collection electrodes 101S3. When the droplets move along the direction X2 from the second region 10B to the first region 10A to perform droplet merging operation, after the third droplets M3 of the plurality of third electrodes 101C are aggregated, the third droplets may move to one second electrode 101B of the length L2 for merging to form one second droplet M2 (the size of the second droplet M2 is larger than the size of the third droplet M3). The second droplet M2 may directly move to the first collection electrodes 101S1 on at least one side of the second electrode 101B along the second direction Y to be screened and collected and may flow into the external second droplet collection apparatus. Or a plurality of second droplets M2 may continue to move to one first electrode 101A in the first region 10A, and further aggregate and merge to form the first droplet M1 (the size of the first droplet M1 is larger than the size of the second droplet M2). Finally, the plurality of first droplets M1 are screened and collected by the third collection electrode 101S3 on at least one side of the first electrode 101A along the second direction Y and may flow into the external first droplet collection apparatus, thereby completing the process of merging small droplets into droplets of various sizes. The microfluidic apparatus 000 provided in one embodiment may not only be used to realize splitting and merging of droplets, but also may realize, through disposing the collection electrodes, the function of moving droplets of corresponding sizes to the regions where the collection electrodes are located and collecting droplets of different sizes in different regions.

It can be understood that, in one embodiment, voltages applied to the collection electrodes and the electrodes around the collection electrodes during the process of collecting droplets may not limited in embodiments of the present disclosure. For example, in the process of collecting the second droplets M2 in the second region 10B, after the second droplets M2 are formed, a driving voltage may be applied to each second electrode 101B in sequence along the direction pointing from the second electrode 101B where the second droplet M2 is located to the first collection electrode 101S1, such that the second droplets M2 may move toward the direction adjacent to the first collection electrodes 101S1 and finally be collected by the first collection electrodes 101S1. Or other driving manners may also be used, which may not be described in detail in one embodiment.

Optionally, referring to FIGS. 16, 18 and 19, in one embodiment, the shapes and sizes of the first collection electrode 101S1 and the second electrode 101B may be same, and the shapes and sizes of the second collection electrode 101S2 and the third electrode 101C may be same. Furthermore, optionally, the shapes and sizes of the third collection electrode 101S3 and the first electrode 101A may be same.

In one embodiment, it describes that the driving electrodes (the first electrode 101A, the second electrode 101B, the third electrode 101C, etc.) and the collection electrodes in the electrode array layer 101 may be made of a same material at a same layer, the first collection electrode 101S1 may also be configured to have the same shape and size as the second electrode 101B, the second collection electrode 101S2 may also be configured to have the same shape and size as the third electrode 101C, and the third collection electrode 101S3 may also be configured to have the same shape and size as the first electrode 101A. Therefore, the materials, shapes and sizes of the driving electrodes and the collection electrodes of a same sub-region 100 may be same; and such electrodes may be formed in a same process, which is beneficial for improving process efficiency; and it may also avoid that when the collection electrodes and the driving electrodes have different sizes and shapes, the driving voltage provided for the collection process may need to be changed, which may be beneficial for reducing driving power consumption.

Figure 20:
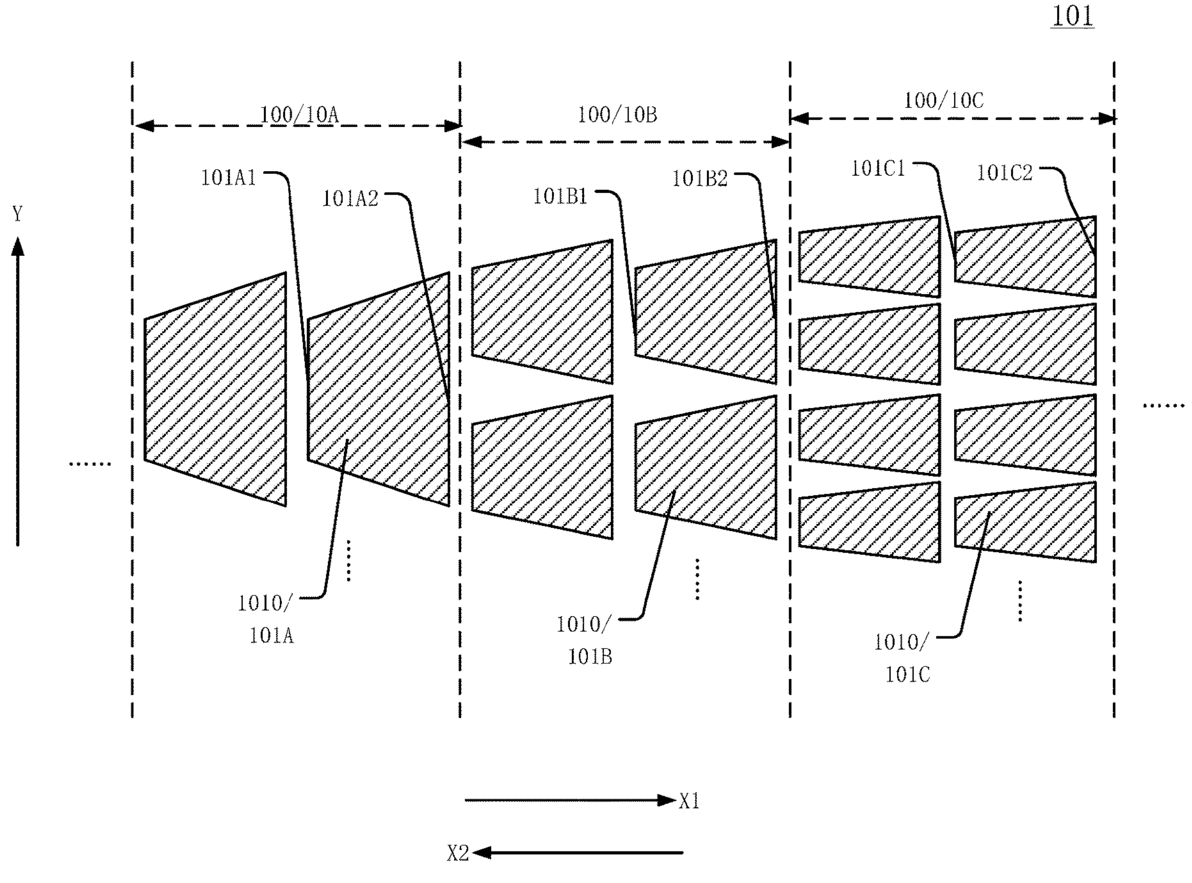
FIG. 20 illustrates another planar structural schematic of an electrode array layer on a first substrate in FIG. 16.

In some optional embodiments, referring to FIGS. 16 and 20, FIG. 20 illustrates another planar structural schematic of the electrode array layer on the first substrate in FIG. 16. In one embodiment, the orthographic projection shape of the first electrode 101A on the first substrate 10 may be a trapezoid, and the orthographic projection shape of the second electrode 101B on the first substrate 10 may be a trapezoid. Optionally, the orthographic projection shape of the third electrode 101C on the first substrate 10 may be a trapezoid.

In one embodiment, it describes that the shapes of the driving electrodes disposed in the electrode array layer 101 may be the square shape in above-mentioned embodiment, the trapezoidal shape shown in FIG. 20 in one embodiment, or any other suitable shapes. In one embodiment, the electrodes 1010 in the electrode array layer 101 may have a same shape only as an example for illustration, which may be beneficial for improving process efficiency. During an implementation, the shapes of the electrodes 1010 in the electrode array layer 101 may also be different, which may not be described in detail in one embodiment.

In one embodiment, the orthographic projection shape of the electrode 1010 on the first substrate 10 may be designed as a trapezoid, so that the change trend of the electrode 1010 may be matched with the change of the distance between the first substrate 10 and the second substrate 20. Therefore, the area and shape of the electrode 1010 may be maintained to be consistent with droplet volume change, which may further be beneficial for being desirably matched with the electrode shape in the process of driving droplets.

For example, the trapezoidal first electrode 101A may include a first short side 101A1 and a first long side 101A2, and along the first direction X1, the first long side 101A2 may be on the side of the first short side 101A1 adjacent to the second region 10B; and the trapezoidal second electrode 101B may include a second short side 101B1 and a second long side 101B2, and along the first direction X1, the second long side 101B2 may be on the side of the second short side 101B1 away from the first region 10A. Optionally, the trapezoidal third electrode 101C may include a third short side 101C1 and a third long side 101C2; and along the first direction X1, the third long side 101C2 may be on the side of the third short side 101C1 away from the second region 10B. In one embodiment, each trapezoidal electrode 1010 may be designed to be that the long side of the trapezoid is closer to a next sub-region 100 than the short side. It can be understood that the long side and the short side of the trapezoid in one embodiment can be understood as the upper base and the lower base that are in parallel with each other in the trapezoid. As shown in FIG. 20, the length of the long side along the second direction Y may be greater than the length of the short side along the second direction Y in each trapezoidal electrode. The long side of the electrode 1010 is closer to the side with smaller cell thickness than the short side, that is, the distance D2 between the first substrate 10 and the second substrate 20 in the second region 10B may be less than the distance D1 between the first substrate 10 and the second substrate 20 in the first region 10A, such that the first long side 101A2 of the trapezoidal first electrode 101A may be closer to the second region 10B than the first short side 101A1 of the trapezoidal first electrode 101A. The distance D3 between the first substrate 10 and the second substrate 20 in the third region 10C may be less than the distance D2 between the first substrate 10 and the second substrate 20 in the second region 10B, such that the second long side 101B2 of the trapezoidal second electrode 101B may be closer to the third region 10C than the second short side 101B1 of the trapezoidal second electrode 101B. Therefore, in the process of splitting the first droplet M1 into the plurality of second droplets M2, after moving to the first electrode 101A adjacent to the second electrode 101B, the first droplet M1 may be further elongated by configuring the first long side 101A2. The first droplet M1 may be first elongated and then be split after moving to the plurality of second electrodes 101B. During the process of splitting the second droplet M2 into the plurality of third droplets M3, after moving to the second electrode 101B adjacent to the third electrode 101C, the second droplet M2 may be further elongated by configuring the second long side 101B2. The second droplet M2 may be first elongated and then be split after moving to the plurality of second electrodes 101B, which may be beneficial for reducing difficulty of splitting the droplets and being easier to split the droplets.

Figure 21:
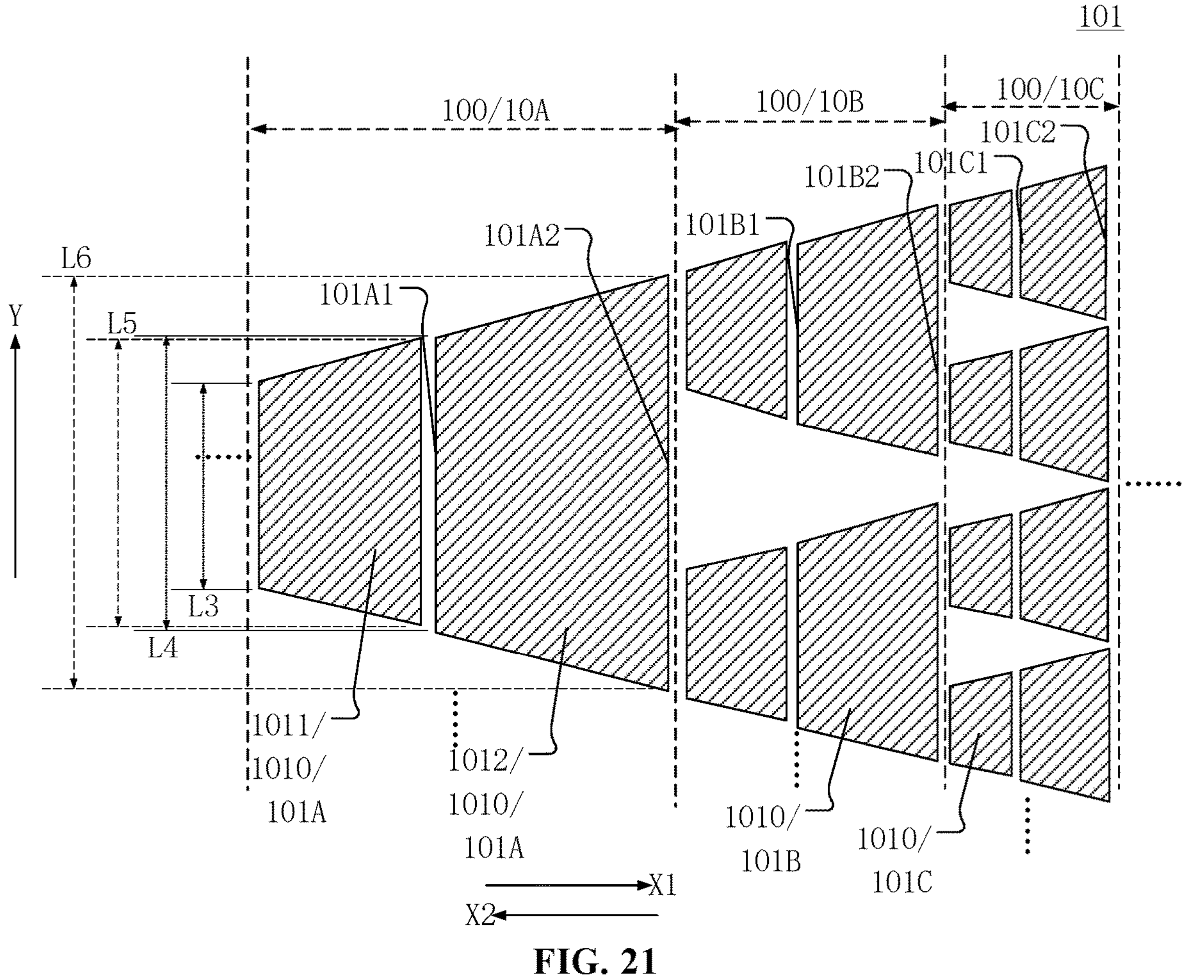
FIG. 21 illustrates another planar structural schematic of an electrode array layer on a first substrate in FIG. 16.

In some optional embodiments, referring to FIGS. 16 and 21, FIG. 21 illustrates another planar structural schematic of the electrode array layer on the first substrate in FIG. 16. In one embodiment, the plurality of first electrodes 101A may include at least a first sub-electrode 1011 and a second sub-electrode 1012; and along the first direction X1, the first sub-electrode 1011 may be on the side of the second sub-electrode 1012 away from the second region 10B.

The orthographic projection area of the first sub-electrode 1011 on the first substrate 10 may be less than the orthographic projection area of the second sub-electrode 1012 on the first substrate 10.

In one embodiment, it describes that the orthographic projection areas of the electrodes 1010 in one sub-region 100 on the first substrate 10 may be different. As shown in FIG. 21, taking the first region 10A as an example, the plurality of first electrodes 101A may at least include the first sub-electrode 1011 and the second sub-electrode 1012, and along the first direction X1, the first sub-electrode 1011 may be on the side of the second sub-electrode 1012 away from the second region 10B. That is, the distance between the first substrate 10 and the second substrate 20 where the first sub-electrode is located may be greater than the distance between the first substrate 10 and the second substrate 20 where the second sub-electrode 1012 is located. The orthographic projection area of the first sub-electrode 1011 on the first substrate 10 may be configured to be less than the orthographic projection area of the second sub-electrode 1012 on the first substrate 10. In such way, when the first droplets M1 of a same size move in the first region 10A, the closer to smaller cell thickness, the larger the area of the first electrode 101A. Therefore, the cell thickness becomes small (the distance between the first substrate 10 and the second substrate 20 becomes small); however, the first droplet M1 that has not been split may still be entirely located on one second sub-electrode 1012 with relatively large area in the first region 10 by configuring that the orthographic projection area of the second sub-electrode 1012 on the first substrate 10 is larger than the orthographic projection area of the first sub-electrode 1011 on the first substrate 10, which may be beneficial for ensuring integrity of the first droplet M1 before splitting.

Optionally, the second electrode 101B in the second region 10B and the third electrode 101C in the third region 10C may refer to the arrangement manner of the first electrode 101A in the first region 10A, such that the integrity of the droplets of a same volume at positions of different cell thicknesses may be satisfied, which may not be described in detail in one embodiment.

In some optional embodiments, referring to FIGS. 16 and 21, along the second direction Y, the length of the first short side 101A1 of the first sub-electrode 1011 is L3, and the length of the first short side 101A1 of the second sub-electrode 1012 is L4, where L4>L3; the length of the first long side 101A2 of the first sub-electrode 1011 is L5, and the length of the first long side 101A2 of the second sub-electrode 1012 is L6, where L6>L5. The first direction X1 may intersect the second direction Y along the direction in parallel with the plane of the first substrate 10.

In one embodiment, it describes that the orthographic projection areas of the electrodes 1010 in one sub-region 100 on the first substrate 10 may be different. As shown in FIG. 21, taking the first region 10A as an example, the plurality of first electrodes 101A may at least include the first sub-electrode 1011 and the second sub-electrode 1012. Along the first direction X1, the first sub-electrode 1011 may be on the side of the second sub-electrode 1012 away from the second region 10B. That is, the distance between the first substrate 10 and the second substrate 20 where the first sub-electrode is located is greater than the distance between the first substrate 10 and the second substrate 20 where the second sub-electrode 1012 is located. The orthographic projection area of the first sub-electrode 1011 on the first substrate 10 may be configured to be less than the orthographic projection area of the second sub-electrode 1012 on the first substrate 10. In such way, when the first droplets M1 of a same size move in the first region 10A, the closer to smaller cell thickness, the larger the area of the first electrode 101A. Therefore, the cell thickness becomes small (the distance between the first substrate 10 and the second substrate 20 becomes small); however, the first droplet M1 that has not been split may still be entirely located on one second sub-electrode 1012 with relatively large area in the first region 10 by configuring that the orthographic projection area of the second sub-electrode 1012 on the first substrate 10 is larger than the orthographic projection area of the first sub-electrode 1011 on the first substrate 10, which may be beneficial for ensuring integrity of the first droplet M1 before splitting. In addition, the orthographic projection area of the first sub-electrode 1011 on the first substrate 10 may be configured to be less than the orthographic projection area of the second sub-electrode 1012 on the first substrate 10, which may be that the length L5 of the first long side 101A2 of the first sub-electrode 1011 may be configured to be less than the length L6 of the first long side 101A2 of the second sub-electrode 1012. Therefore, it may be beneficial for that with the reduction of the cell thickness in the first region 10A, the closer to the second region 10B, the larger the first long side 101A2 of the second sub-electrode 1012, and the larger the first short side 101A1 of the second sub-electrode 1012, which may further be beneficial for the elongation of the first droplet M1 along the second direction Y in the first region 10A, so that the first droplet M1 may be easily split after the first droplet M1 reaches the second region 10B. Similarly, the length L3 of the first short side 101A1 of the first sub-electrode 1011 along the second direction Y may be configured to be less than the length L4 of the first short side 101A1 of the second sub-electrode 1012. Therefore, it may be beneficial for that with the increase of the cell thickness in the first region 10A, the further away from the second region 10B, the smaller the first short side 101A1 of the first sub-electrode 1011, and the smaller the first long side 101A2 of the first sub-electrode 1011, which may further be beneficial for the aggregation of the second droplets M2 along the second direction Y in the first region 10A, so that the second droplets M2 may be easily aggregated and merged after the plurality of second droplets M2 reaches the first region 10A.

Figure 22:
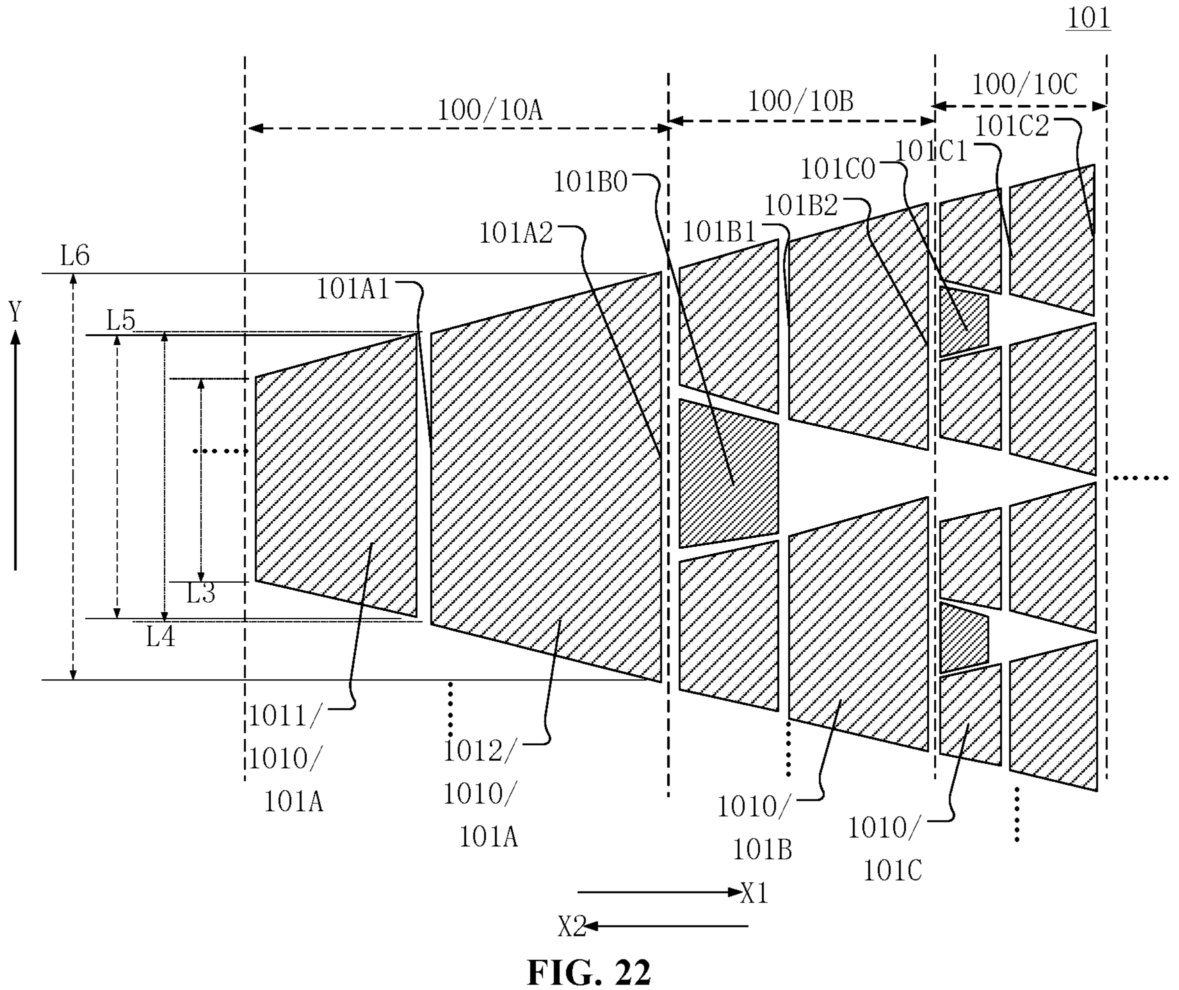
FIG. 22 illustrates another planar structural schematic of an electrode array layer on a first substrate in FIG. 16.

Optionally, referring to FIGS. 16 and 22, FIG. 22 illustrates another planar structural schematic of the electrode array layer on the first substrate in FIG. 16. In one embodiment, along the second direction Y, a first auxiliary electrode 101B0 may be further between adjacent second electrodes 101B, and a second auxiliary electrode 101C0 may be further between adjacent third electrodes 101C. The first auxiliary electrode 101B0 and the second auxiliary electrode 101C0 may be used to fill the vacant areas of the electrodes 1010 in the second region 10B and the third region 10C and may also be used to desirably split droplets. For example, for the first auxiliary electrode 101B0 between the second electrodes 101B, when the first droplet M1 moves to two second electrodes 101B and the first auxiliary electrode 101B0 between two second electrodes, the first auxiliary electrode 101B0 may be configured to float (removing the driving voltage signal), and the driving voltage signal may be applied to two second electrodes 101B at two ends of the first auxiliary electrode 101B0. Therefore, one first droplet M1 may be split at the position of the first auxiliary electrode 101B0 and split into two second droplets M2. In such way, the first auxiliary electrode 101B0 and the second auxiliary electrode 101C0 of one embodiment may make the droplet division easier.

Furthermore, optionally, referring to FIGS. 16 and 22, the first auxiliary electrode 101B0 may be between two second electrodes 101B closest to the first region 10A, and the second auxiliary electrode 101C0 may be between two third electrodes 101C closest to the second region 10B. Therefore, after the first droplet M1 moves from the first region 10A to the second region 10B, the division may be completed immediately by the cooperation of the first auxiliary electrode 101B0; and after the second droplet M2 moves from the second region 10B to the third region 10C, the division may be completed immediately by the cooperation of the second auxiliary electrode 101C0, which may be beneficial for improving splitting efficiency of droplets.

It can be understood that the first auxiliary electrode 101B0 and the second auxiliary electrode 101C0 in one embodiment may be configured in a same layer with a same material as the electrodes 1010 in the electrode array layer 101 and may also be configured through a conductive film layer, which may not be limited in one embodiment. Above-mentioned configuration may only need to satisfy that the first auxiliary electrode 101B0 is configured between at least two second electrodes 101B corresponding to one first electrode 101A, the second auxiliary electrode 101C0 is configured between at least two third electrodes 101C corresponding to one second electrode 101B, which may cooperate with the electrodes 1010 on two sides of above auxiliary electrodes to complete the division of droplets. The arrangement and shapes of the auxiliary electrodes may not be limited in one embodiment.

Optionally, as shown in FIG. 16 and FIG. 17, in one embodiment, the widths W0 of the electrodes 1010 in different sub-regions 100 along the first direction X1 may be different. The width W1 of the first electrode 101A of the first region 10A along the first direction X1 may be set to be greater than the width W2 of the second electrode 101B of the second region 10B along the first direction X1; and the width W2 of the second electrode 101B of the second region 10B along the first direction X1 may be set to be greater than the width W3 of the third electrode 101C of the third region 10C along the first direction X1. Therefore, during droplet splitting operation, since the width X1 along the first direction becomes small, in the direction from the first region 10A to the third region 10C, the droplet may be more elongated along the second direction Y, which may be more beneficial for division. During droplet merging operation, along the direction pointing from the third region 10C to the first region 10A, the droplets may gradually aggregate along the second direction Y to provide sufficient width space for sufficient merging.

Figure 23:
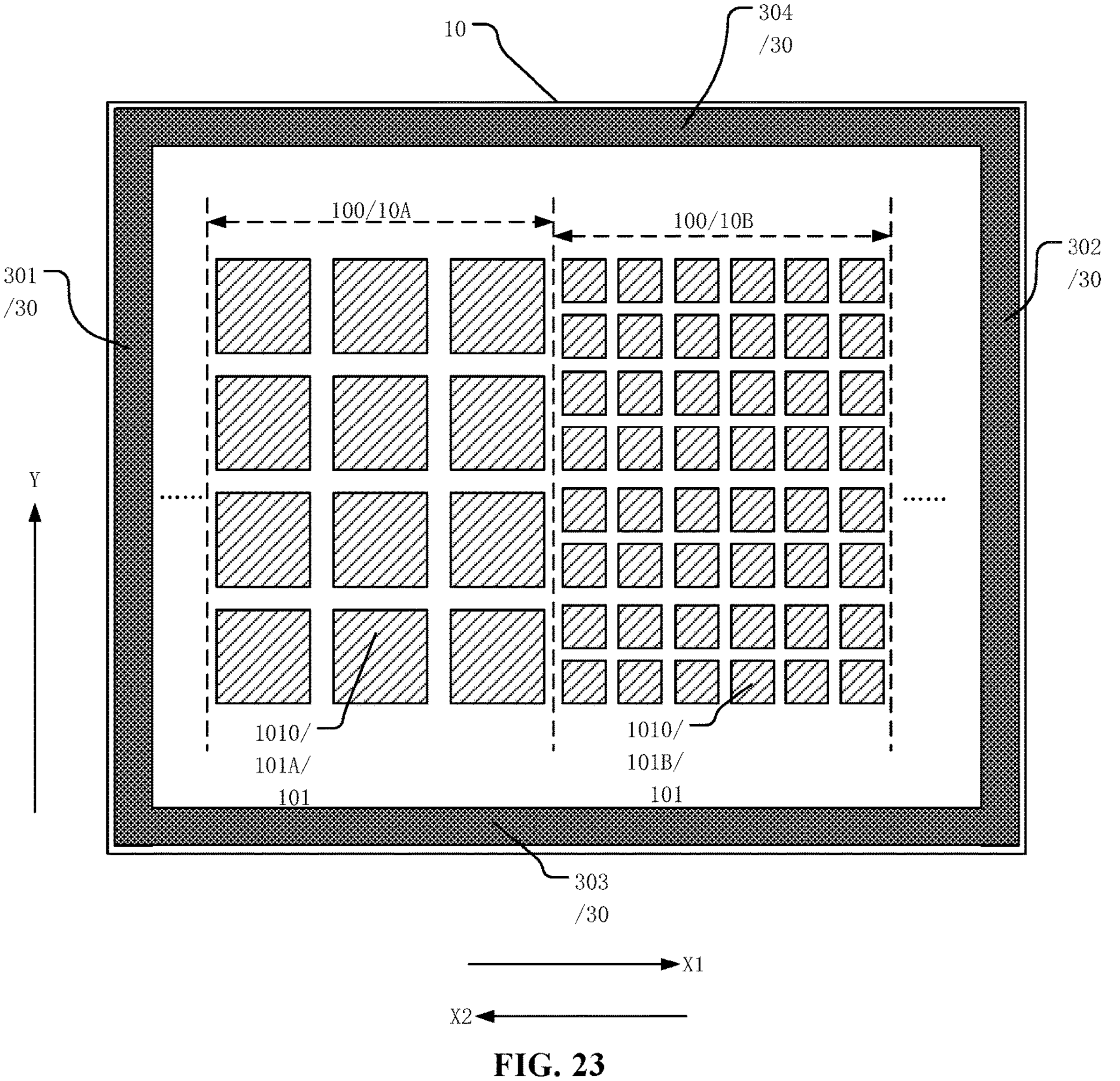
FIG. 23 illustrates a top structural view of a first substrate in FIG. 4.
Figure 24:
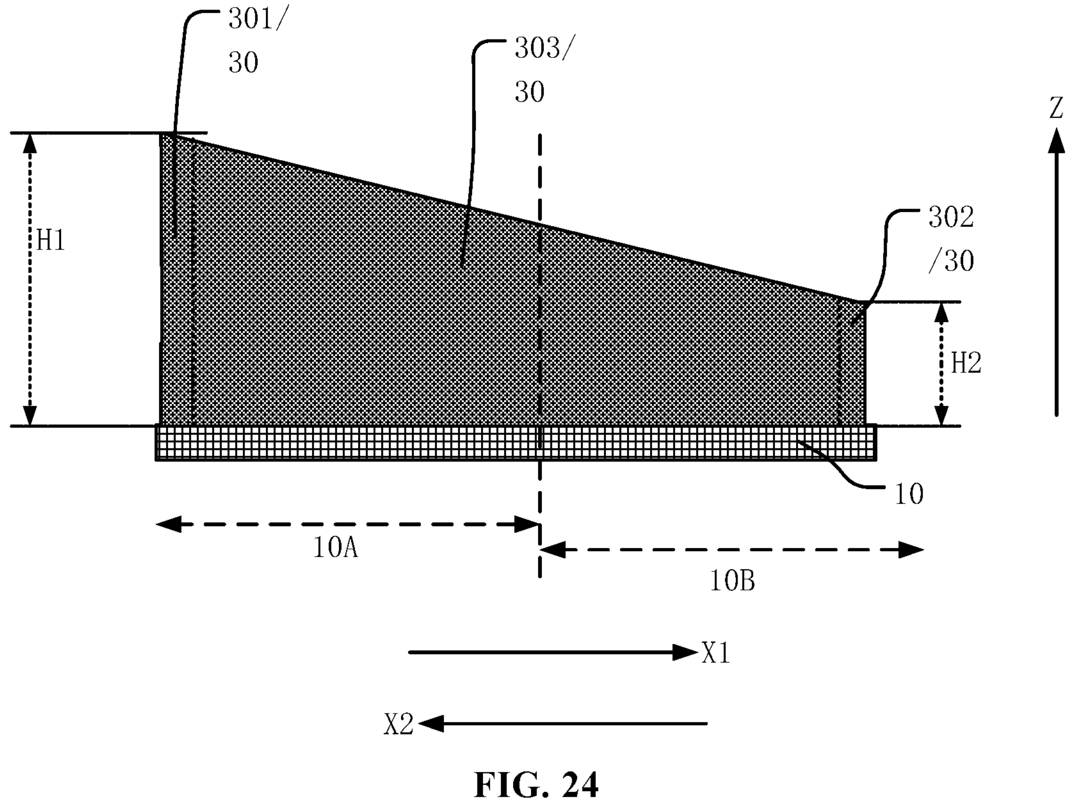
FIG. 24 illustrates a front structural view of a first substrate in FIG. 23.

In some optional embodiments, referring to FIGS. 4, 23 and 24, FIG. 23 illustrates a top structural view of the first substrate in FIG. 4; and FIG. 24 illustrates a front structural view of the first substrate in FIG. 23 (it can be understood that, in order to clearly illustrate the structure of one embodiment, filling may not be performed on the first substrate 10 in FIG. 23). In one embodiment, a frame adhesive 30, disposed by surrounding the electrode array layer 101, may be between the first substrate 10 and the second substrate 20.

The frame adhesive 30 may at least include a first sub-section 301 and a second sub-section 302. Along the first direction X1, the first sub-section 301 may be on the side of the first region 10A away from the second region 10B, and the second sub-section 302 may be on the side of the second region 10B away from the first region 10A.

In the direction Z perpendicular to the plane of the first substrate 10, the thickness H1 of the first sub-section 301 may be consistent, the thickness H2 of the second sub-section 302 may be consistent, and the thickness H1 of the first sub-section 301 may be greater than the thickness H2 of the second sub-section 302.

In one embodiment, it describes that the first substrate 10 and the second substrate 20 may be fixed opposite with each other through the frame adhesive 30 which is disposed by surrounding the electrode array layer 101, thereby forming a cavity for accommodating droplets. That is, the frame adhesive 30 may be disposed by surrounding the electrode array layer 101 at outer contours of the first substrate 10 and the second substrate 20, which may avoid that the frame adhesive 30 affects the functions of the electrodes in the electrode array layer 101. In one embodiment, the frame adhesive 30 may at least include the first sub-section 301 and the second sub-section 302. Along the first direction X1, the first sub-section 301 and the second sub-section 302 may be on two opposite sides of the electrode array layer 101, respectively. The first sub-section 301 may be on the side of the first region 10A away from the second region 10B, and the second sub-section 302 may be on the side of the second region 10B away from the first region 10A. In the direction Z perpendicular to the plane of the first substrate 10, the thickness H1 of the first sub-section 301 may be configured to be consistent, the thickness H2 of the second sub-section 302 may be configured to be consistent, and the thickness H1 of the first sub-section 301 may be configured to be greater than the thickness H2 of the second sub-section 302. Therefore, after the electrode array layer 101 and other structures are formed on the first substrate 10, and after the second electrode layer 201 and other structures are formed on the second substrate 20, the first substrate 10 and the second substrate 20 after the attaching operation may directly form the angle α by configuring the first sub-section 301 and the second sub-section 302 of the frame adhesive 30, which may be beneficial for ensuring the overall stability and sealing of the microfluidic apparatus 000, simplifying the process of forming the box using the first substrate 10 and the second substrate 20, and reducing formation difficulty.

Optionally, the microfluidic apparatus 000 in one embodiment may be the box independently formed by the first substrate 10 and the second substrate 20 which are small-sized, rather than formed by cutting a formed box using a large sheet of glass. In such way, it may avoid the impact of the cutting process on apparatus performance and may also avoid that when the large sheet of glass is re-cut into boxes, the angles between the first substrates 10 and the second substrates 20 of different microfluidic apparatuses after cutting may be different which may affect mass production of products.

It can be understood that, in one embodiment, the surface of the first sub-section 301 of the frame adhesive 30 facing the first substrate 10 and the surface of the second sub-section 302 facing the first substrate 10 may be on a same horizontal plane, which may be beneficial ensuring flatness after the frame adhesive 30 is attached to the first substrate 10.

Optionally, as shown in FIGS. 23 and 24, the frame adhesive 30 in one embodiment may further include a third sub-section 303 and a fourth sub-section 304. Along the second direction Y, the third sub-section 303 and the fourth sub-section 304 may be on two opposite sides of the electrode array layer 101, respectively. Two ends of the third sub-section 303 may be respectively connected to one end of the first sub-section 301 and one end of the second sub-section 302; and two ends of the fourth sub-section 304 may be respectively connected to the other end of the first sub-section 301 and the other end of the second sub-section 302. Therefore, the first sub-section 301, the third sub-section 303, the second sub-section 302, and the fourth sub-section 304 may be sequentially connected end to end to form a sealed frame body surrounding the electrode array layer 101.

In one embodiment, in the direction Z perpendicular to the plane of the first substrate 10, the thickness of the third sub-section 303 of the first region 10A may be greater than the thickness of the third sub-section 303 of the second region 10B; and in the direction Z perpendicular to the plane of the first substrate 10, the thickness of the fourth sub-section 304 of the first region 10A may be greater than the thickness of the fourth sub-section 304 of the second region 10B. Furthermore, optionally, the distance between the first substrate 10 and the second substrate 20 in the direction Z perpendicular to the plane of the first substrate 10 may gradually change along the first direction X1. Therefore, in order to ensure the attaching and sealing property between the first substrate 10 and the second substrate 20, along the direction X1 pointing from the first region 10A to the second region 10B, the thickness of the third sub-section 303 in the direction Z perpendicular to the plane of the first substrate 10 may be configured to gradually decrease, and the thickness of the fourth sub-section 304 in the direction Z perpendicular to the plane of the first substrate 10 may also be configured to gradually decrease. In such way, the flat first substrate 10 and the flat second substrate 20 may be desirably attached to form the microfluidic apparatus with the angle α.

Figure 25:
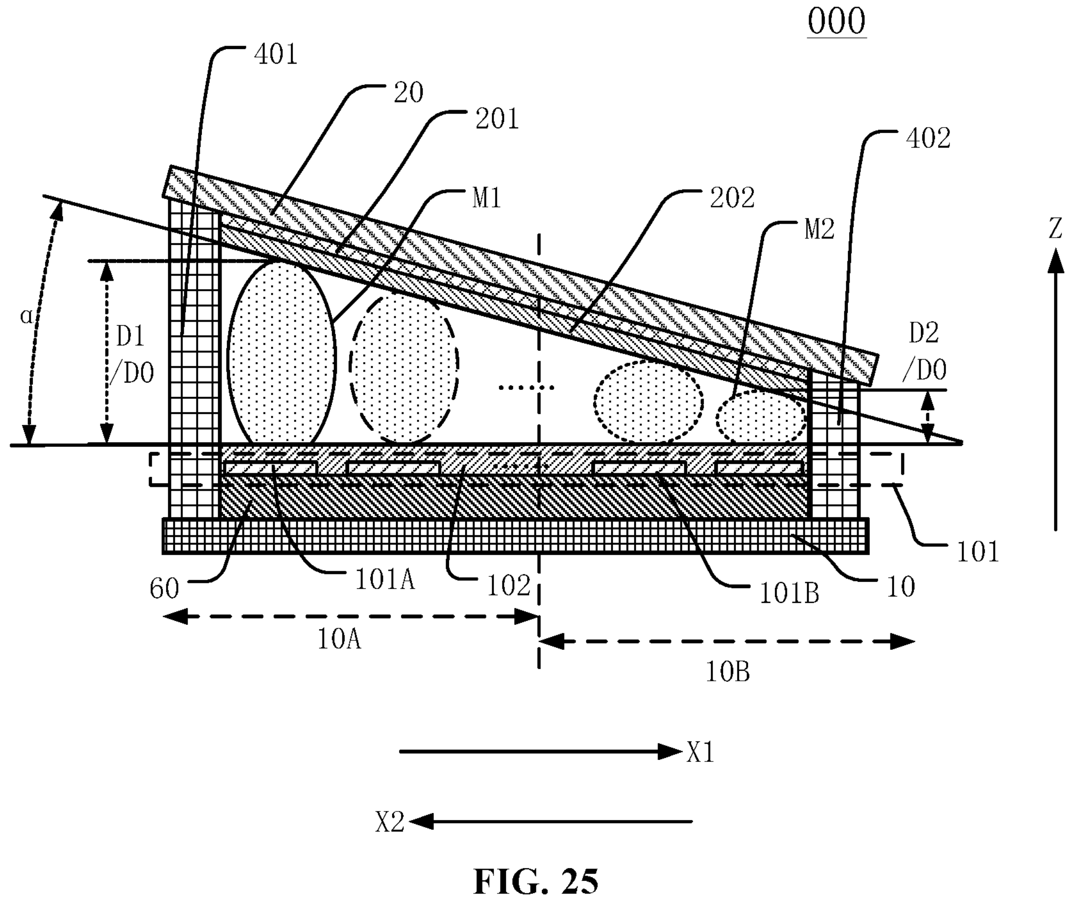
FIG. 25 illustrates another structural schematic of an exemplary microfluidic apparatus according to various embodiments of the present disclosure.
Figure 26:
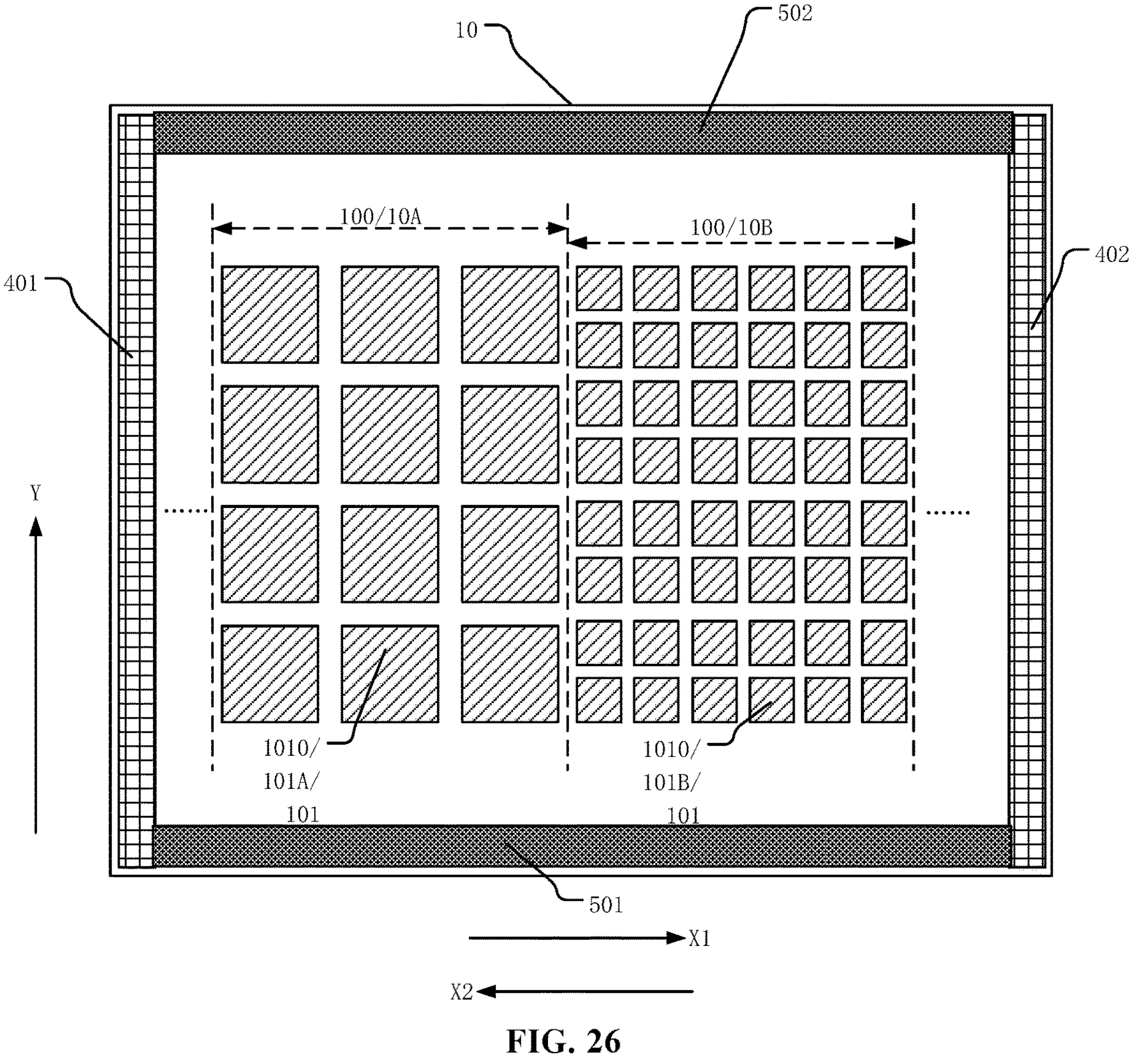
FIG. 26 illustrates a top structural view of a first substrate in FIG. 25.
Figure 27:
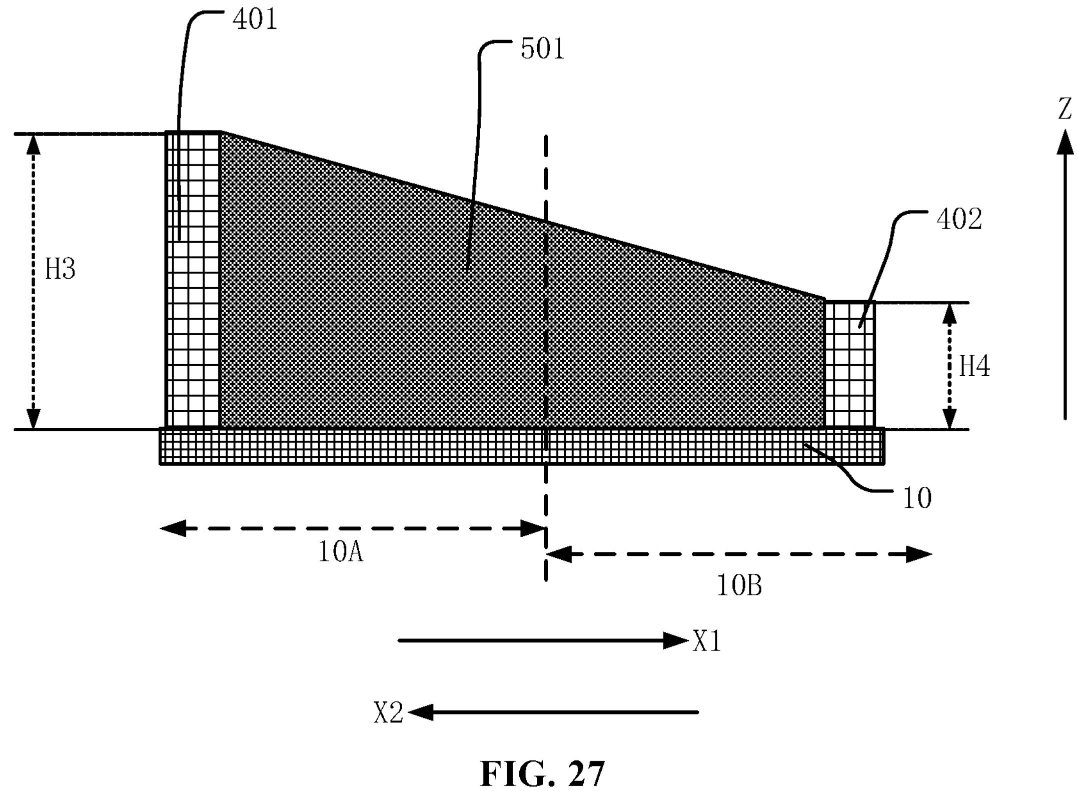
FIG. 27 illustrates a front structural view of a first substrate in FIG. 26.

In some optional embodiments, referring to FIGS. 25, 26 and 27, FIG. 25 illustrates another structural schematic of an exemplary microfluidic apparatus according to various embodiments of the present disclosure; FIG. 26 illustrates a top structural view of the first substrate in FIG. 25; and FIG. 27 illustrates a front structural view of the first substrate in FIG. 26 (it can be understood that, in order to clearly illustrate the structure of one embodiment, filling may not be performed on the first substrate 10 in FIG. 26). In one embodiment, a first patch 401 and a second patch 402 may be between the first substrate 10 and the second substrate 20; and along the first direction X1, the first patch 401 may be on the side of the first region 10A away from the second region 10B, and the second patch 402 may be on the side of the second region 10B away from the first region 10A.

In the direction Z perpendicular to the plane of the first substrate 10, the thickness H3 of the first patch 401 may be consistent, the thickness H4 of the second patch 402 may be consistent, and the thickness H3 of the first patch 401 may be greater than the thickness H4 of the second patch 402.

In one embodiment, it describes that opposite attaching of the first substrate 10 and the second substrate 20 may be achieved through two independent patches including the first patch 401 and the second patch 402. Along the first direction X1, the first patch 401 and the second patch 402 may be on two opposite sides of the electrode array layer 101, respectively. The first patch 401 may be on the side of the first region 10A away from the second region 10B, and the second patch 402 may be on the side of the second region 10B away from the first region 10A. In the direction Z perpendicular to the plane of the first substrate 10, the thickness H3 of the first patch 401 may be consistent, the thickness H4 of the second patch 402 may be consistent, and the thickness H3 of the first patch 401 may be greater than the thickness H4 of the second patch 402. During the formation process, after the electrode array layer 101 and other structures are formed on the first substrate 10, the first patch 401 and the second patch 402 may be respectively disposed on the outer contour of the first substrate 10; the surfaces of the first patch 401 and the second patch 402 facing the first substrate 10 may be fixed to the first substrate 10 by liquid glue or double-sided tape (not shown in FIGS. 25-27); and a gradient opposite to the second substrate 20 may be pre-formed on the first substrate 10 by the first patch 401 and the second patch 402 with different thicknesses. Optionally, the structure connecting the first patch 401 and the second patch 402 at the periphery of the electrode array layer 101 may be adhesive, filling adhesive, and/or the like. Finally, the second substrate 20 with formed second electrode layer 201 and other structures may be directly and oppositely attached to the surfaces of the first patch 401 and the second patch 402 on the side away from the first substrate 10, thereby forming the cavity for accommodating droplets. After the attaching process, the first substrate 10 and the second substrate 20 may directly form the angle α. In such way, it may be beneficial for ensuring the overall stability and sealing of the microfluidic apparatus 000 and simplifying the process of forming box using the first substrate 10 and the second substrate 20 through directly attaching the first patch 401 and the second patch 402 on the first substrate 10, thereby reducing formation difficulty.

It can be understood that, in one embodiment, the side surface of the first patch 401 facing the first substrate 10 and the side surface of the second patch 402 facing the first substrate 10 may be on a same horizontal plane, which may further be beneficial for ensuring the flatness between the first patch 401 and the first substrate 10 and between the second patch 402 and the first substrate 10 after the fixing and attaching process.

Optionally, as shown in FIGS. 25 to 27, in one embodiment, a first filling adhesive strip 501 and a second filling adhesive strip 502 may further be between the first substrate 10 and the second substrate 20. One end of the first patch 401 and one end of the second patch 402 may be connected by the first filling adhesive strip 501, and the other end of the first patch 401 and the other end of the second patch 402 may be connected by the second filling adhesive strip 502.

Along the direction in parallel with the plane of the first substrate 10, the first filling adhesive strip 501 and the second filling adhesive strip 502 may respectively be on two opposite sides of the electrode array layer 101. The first patch 401, the first filling adhesive strip 501, the second patch 402, and the second filling adhesive strip 502 may form a structure surrounding the electrode array layer 101. That is, the first patch 401, the first filling adhesive strip 501, the second patch 402, and the second filling adhesive strip 502 may be fixedly connected end to end in sequence to form a sealed frame body surrounding the electrode array layer 101.

Along the first direction X1, the thickness of the first filling adhesive strip 501 in the direction Z perpendicular to the plane of the first substrate 10 may gradually decrease, and the thickness of the second filling adhesive strip 502 in the direction Z perpendicular to the plane of the first substrate 10 may gradually decrease.

In one embodiment, along the first direction X1, the thickness of the first filling adhesive strip 501 in the direction Z perpendicular to the plane of the first substrate 10 may gradually decrease, and the thickness of the second filling adhesive strip 502 in the direction Z perpendicular to the plane of the first substrate 10 may gradually decrease. The distance between the first substrate 10 and the second substrate 20 in the direction Z perpendicular to the plane of the first substrate 10 may gradually change along the first direction X1. Therefore, in order to ensure the attaching and sealing property between the first substrate 10 and the second substrate 20, along the direction X1 pointing from the first region 10A to the second region 10B, the thickness of the first filling adhesive strip 501 in the direction Z perpendicular to the plane of the first substrate 10 may be configured to gradually decrease, and the thickness of the second filling adhesive strip 502 in the direction Z perpendicular to the plane of the first substrate 10 may be configured to gradually decrease. In such way, the flat first substrate 10 and the flat second substrate 20 may be desirably attached to form the microfluidic apparatus with the angle α.

Optionally, the first patch 401, the second patch 402 and the frame adhesive 30 in one embodiment may be sealing structures made of different materials. The first patch 401 and the second patch 402 may be prefabricated solid support insulation structures; and the upper and lower surfaces of the first patch 401 and the second patch 402 may be disposed with liquid glue or double-sided tape to make the upper and lower surfaces have a certain viscosity and may be fixedly attached to the substrates. For the frame adhesive 30, a filling adhesive may be filled around the outer contours of the substrates during the formation process of the microfluidic apparatus 000, thereby forming the frame adhesive 30 surrounding the electrode array layer 101.

Figure 28:
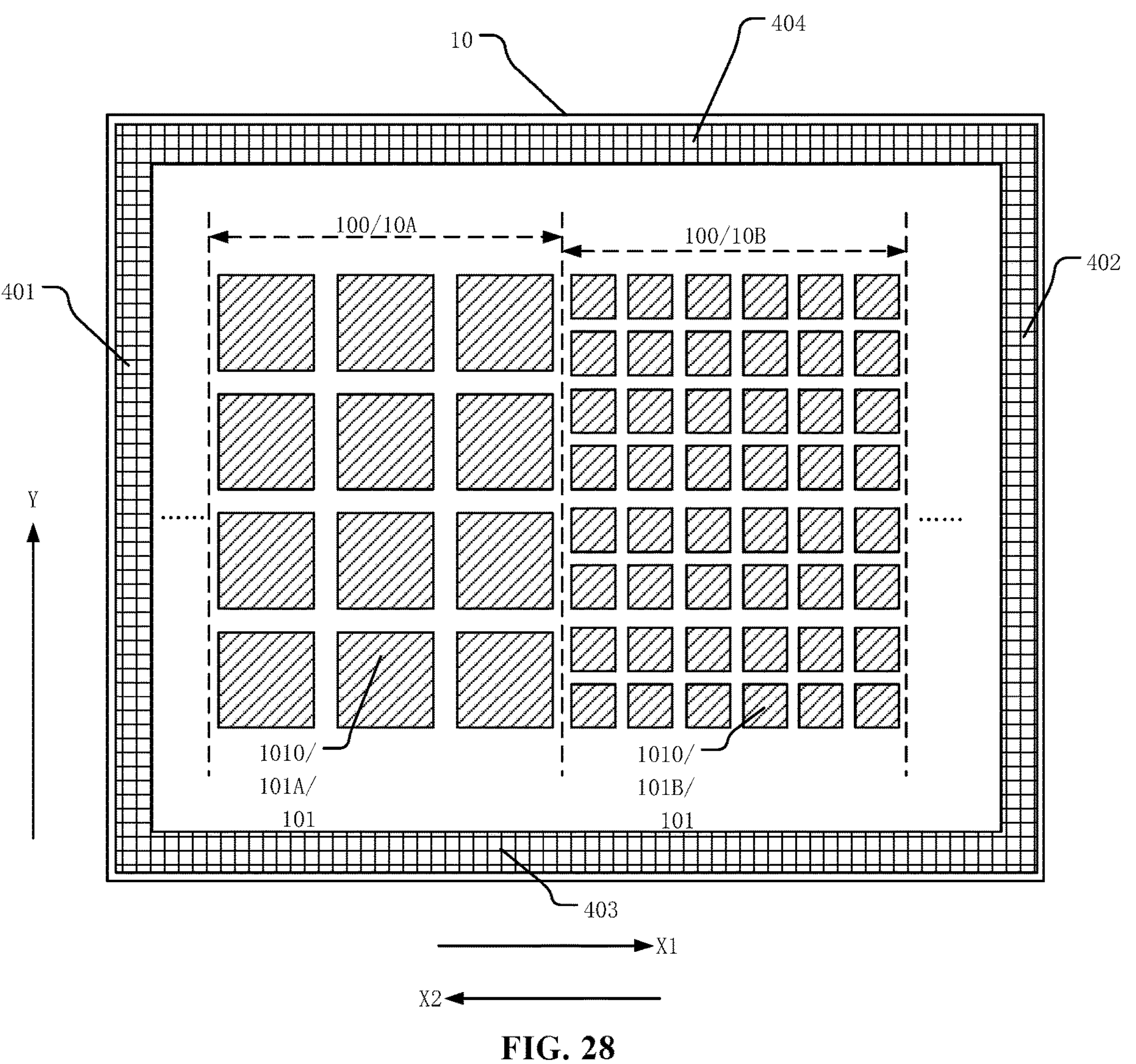
FIG. 28 illustrates another top structural view of a first substrate in FIG. 25.

In some optional embodiments, referring to FIGS. 25, 28 and 29, FIG. 28 illustrates a top structural view of the first substrate in FIG. 25; and FIG. 29 illustrates a front structural view of the first substrate in FIG. 28 (it can be understood that in order to clearly illustrate the structure of one embodiment, filling may not be performed on the first substrate 10 in FIG. 28). In one embodiment, the first patch 401 and the second patch 402 may be between the first substrate 10 and the second substrate 20; along the first direction X1, the first patch 401 may be on the side of the first region 10A away from the second region 10B, and the second patch 402 may be on the side of the second region 10B away from the first region 10A; and in the direction Z perpendicular to the plane of the first substrate 10, the thickness H3 of the first patch 401 may be consistent, the thickness H4 of the second patch 402 may be consistent, and the thickness H3 of the first patch 401 may be greater than the thickness of the second patch 402 H4.

A third patch 403 and a fourth patch 404 may further be between the first substrate 10 and the second substrate 20. Two ends of the third patch 403 may be respectively connected to one end of the first patch 401 and one end of the second patch 402; and two ends of the fourth patch 404 may be respectively connected to the other end of the first patch 401 and the other end of the second patch 402.

Along the direction in parallel with the plane of the first substrate 10, the third patch 403 and the fourth patch 404 may be respectively located on two opposite sides of the electrode array layer 101. The first patch 401, the third patch 403, the second patch 402, and the fourth patch 404 may integrally form a structure surrounding the electrode array layer 101. Optionally, the first patch 401, the third patch 403, the second patch 402, and the fourth patch 404 may be prefabricated before the formation of the microfluidic apparatus. The horizontal surface of an insulation patch at one side may be cut obliquely so that the upper and lower surfaces of the insulation patch may form the required angle; and the middle area may be hollowed out to form a hollow structure corresponding to the size of the electrode array layer 101. Therefore, one side of the insulation patch along the first direction X1 is the first patch 401, and the other side is the second patch 402, where in the direction Z perpendicular to the plane of the first substrate 10, the thickness H3 of the first patch 401 may be consistent, the thickness H4 of the second patch 402 may be consistent, and the thickness H3 of the first patch 401 may be greater than the thickness H4 of the second patch 402; and one side of the insulation patch along the second direction Y is the third patch 403, and the other side is the fourth patch 404, where along the first direction X1, the thickness of the third patch 403 in the direction Z perpendicular to the plane of the first substrate 10 may gradually decrease and the thickness of the fourth patch 404 in the direction Z perpendicular to the plane of the first substrate 10 may gradually decrease. In one embodiment, the first substrate 10 and the second substrate 20 may be sealed to form the box structure by four surrounding patches, integrally, which may be beneficial for ensuring the overall stability and sealing of the microfluidic apparatus 000; and the first patch 401, the second patch 402, the third patch 403, and the fourth patch 404 may be directly attached on the first substrate 10, which may further simplify the process of forming the first substrate 10 and the second substrate 20 into a box and more effectively reduce formation difficulty.

Optionally, in one embodiment, fixing the first substrate 10 and the second substrate 20 into the box may also be realized by insulation patches and a frame adhesive (not shown in drawings). Not only insulation patches formed by the first patch 401, the second patch 402, the third patch 403 and the fourth patch 404, but also the adhesive frame attached with the insulation patches may be between the first substrate 10 and the second substrate 20. In the direction Z perpendicular to the plane of the first substrate 10, the thickness H3 of the first patch 401 may be consistent, the thickness H4 of the second patch 402 may be consistent, and the thickness H3 of the first patch 401 may be greater than the thickness H4 of the second patch 402. Along the second direction Y, the insulation patch on one side may be the third patch 403, and the insulation patch on the other side may be the fourth patch 404. Along the first direction X1, the thickness of the third patch 403 in the direction Z perpendicular to the plane of the first substrate 10 may gradually decrease; and the thickness of the fourth patch 404 in the direction Z perpendicular to the plane of the first substrate 10 may gradually decrease. In the box-forming process of the first substrate 10 and the second substrate 20, the side of the insulation patch facing the first substrate 10 may be on a same horizontal plane; the surface of the insulation patch facing the first substrate 10 may be fixedly attached to the surface of the first substrate 10 facing the second substrate 20 through the frame adhesive; and the frame adhesive may be an adhesive structure arranged by surrounding the electrode array layer 101. In addition, the side of the insulation patch facing the second substrate 20 may be a structure with different heights, and the surface of the insulation patch facing the side of the second substrate 20 may be fixedly attached to the surface of the second substrate 20 facing the side of the first substrate 10. Therefore, the first substrate 10 and the second substrate 20 may be fixed to form the box through the cooperation of the insulation patch and the frame adhesive. In such way, the use of the insulation patch may not only reduce the difficulty of forming the box, but also avoid the problem that the required cell thickness of the first substrate 10 and the second substrate 20 may be difficult to be achieved because the thickness is insufficient in the formation process of the frame adhesive when only the frame adhesive is used to fix the first substrate 10 with the second substrate 20, which may be beneficial for improving process yield and process efficiency.

In some optional embodiments, referring to FIGS. 4-29, 30, 31, 32, 33 and 34, FIG. 30 illustrates a flowchart of a driving method of a microfluidic apparatus according to various embodiments of the present disclosure; and FIGS. 31-34 illustrate schematics of a process of performing droplet splitting using the driving method provided in FIG. 30. It can be understood that, in order to clearly illustrate the process of moving and splitting droplets in one embodiment, only the electrodes in the electrode array layer that need to be applied with voltage during the moving process may be filled with patterns; and remaining floating electrodes in the electrode array layer may not be filled with patterns. The driving method provided in one embodiment may be applied to the microfluidic apparatus 000 in above-mentioned embodiments to perform droplet splitting operation. It can be understood that, in one embodiment, the orthographic projection area of the first electrode 101A on the first substrate 10 and the orthographic projection area of the second electrode 101B on the first substrate 10 are different, which is taken as an example to illustrate the driving method. The driving method may include following exemplary steps.

Figure 31:
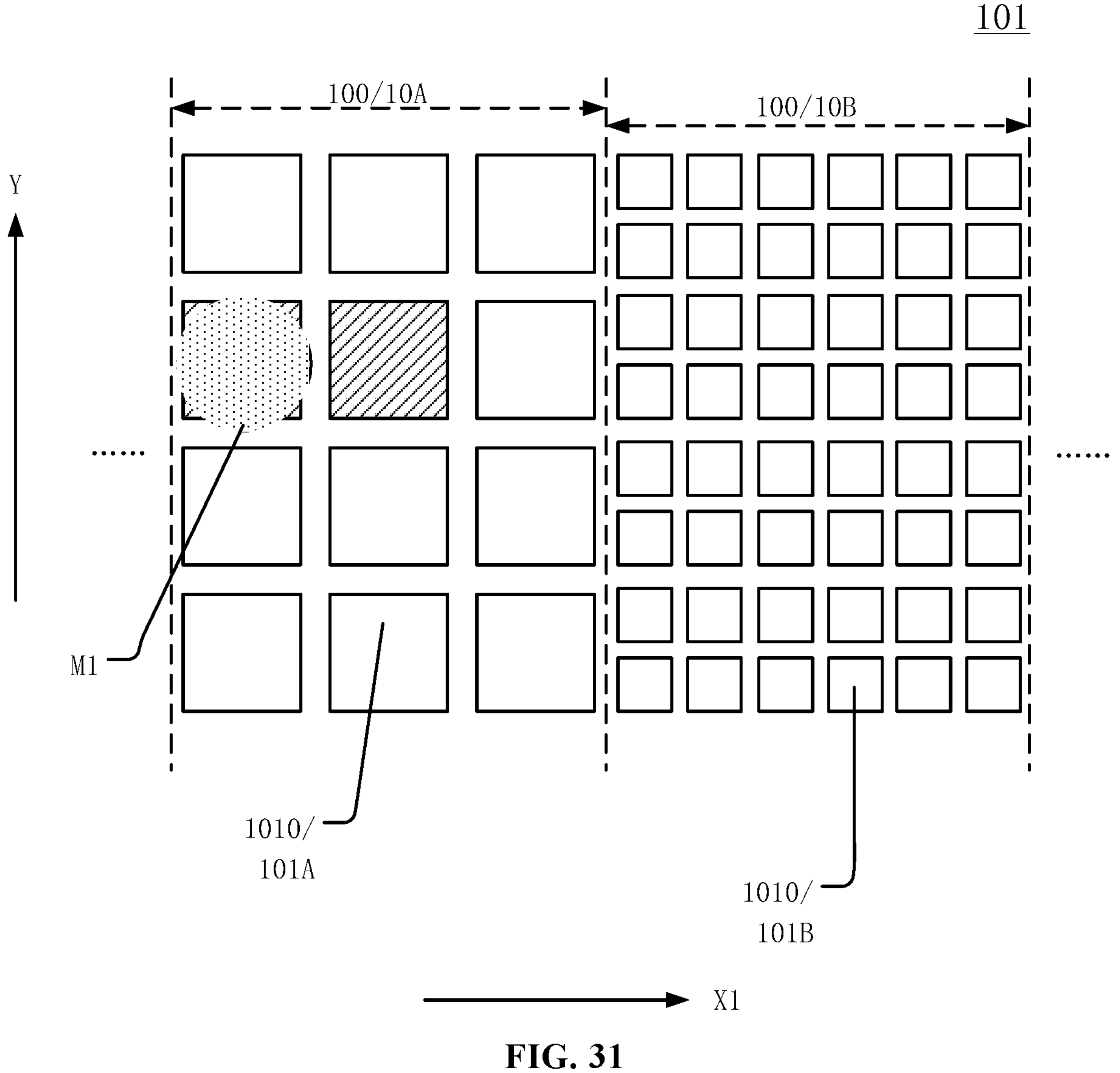
FIGS. 31-34 illustrate schematics of a process of performing droplet splitting using a driving method provided in FIG. 30.

At S10, along the first direction X1 (the direction X1 pointing from the first region 10A to the second region 10B), the second electrode layer 201 may be connected to a ground signal, and the driving voltage may be provided to the first electrodes 101A sequentially. Optionally, a driving electric field for driving the first droplet M1 to move may be formed between the first electrode 101A of the driving voltage and the second electrode layer 201 of the ground signal; and driven by the electric field formed between the first electrode 101A and the second electrode layer 201, the first droplet M1 between the first substrate 10 and the second substrate 20 may move along the direction X1 pointing from the first region 10A to the second region 10B. As shown in FIG. 31, for the first electrode 101A to which the driving voltage needs to be applied when the first droplet M1 moves in the first region 10A may refer to the schematic of the first electrode 101A with filled pattern in FIG. 31. Furthermore, optionally, in FIG. 31, only one first droplet M1 is used as an example for illustration. During an implementation, the number of droplets for droplet operation in the microfluidic apparatus 000 may not be limited to one, and multiple first droplets M1 may be operated simultaneously. In one embodiment, only one first droplets M1 is used as an example for clear illustration.

Figure 32:
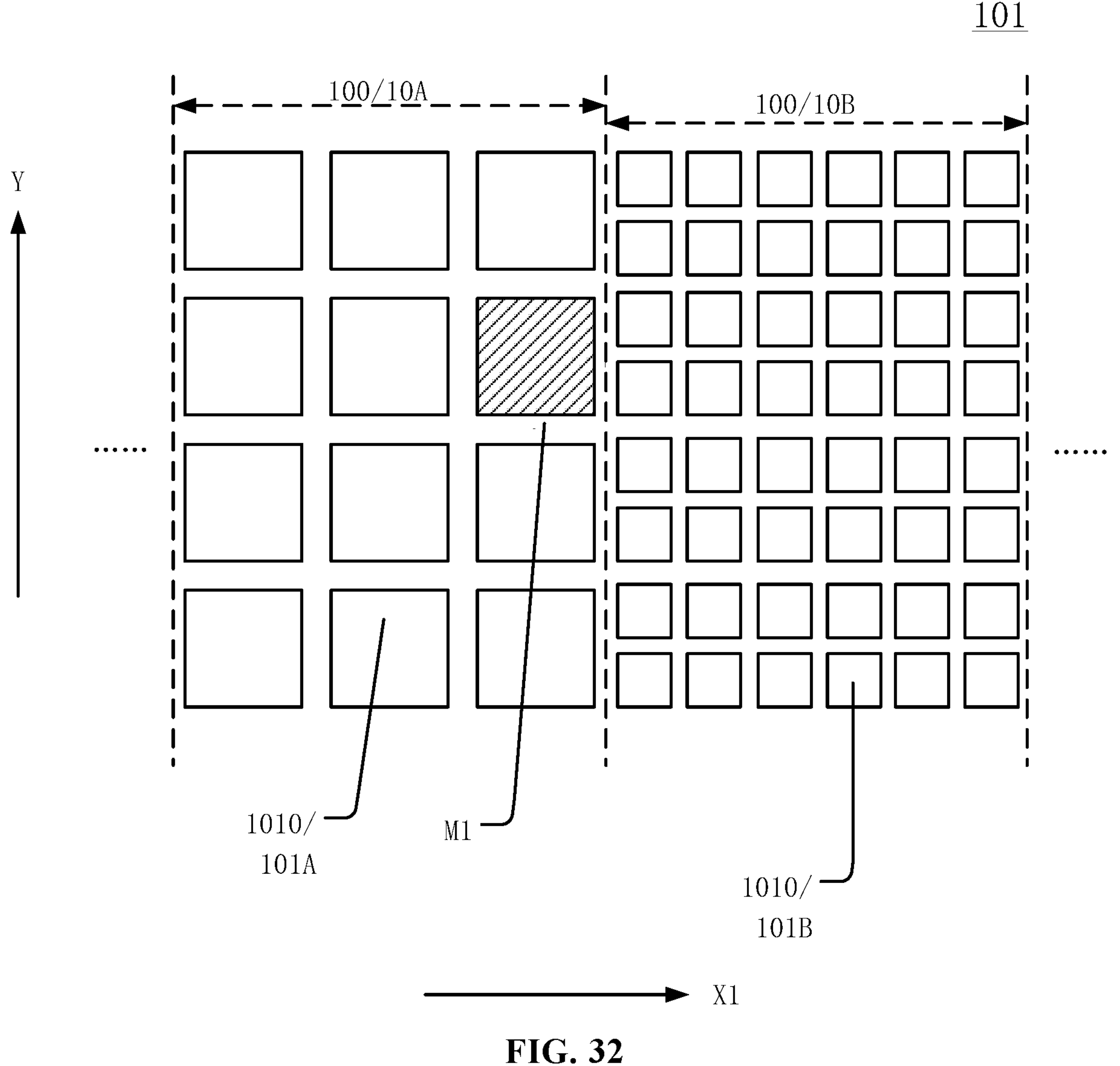
Figure 33:
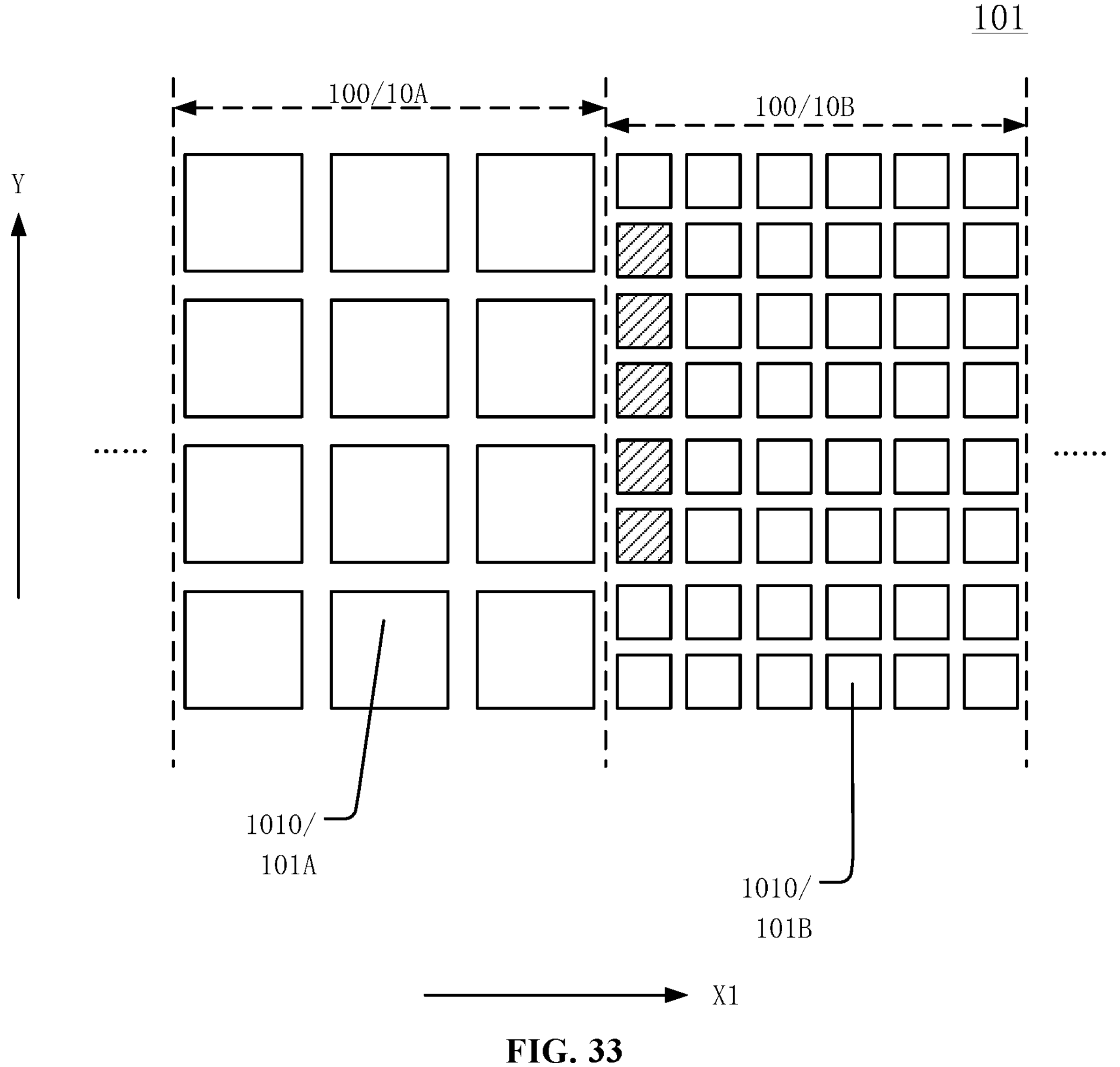
Figure 34:
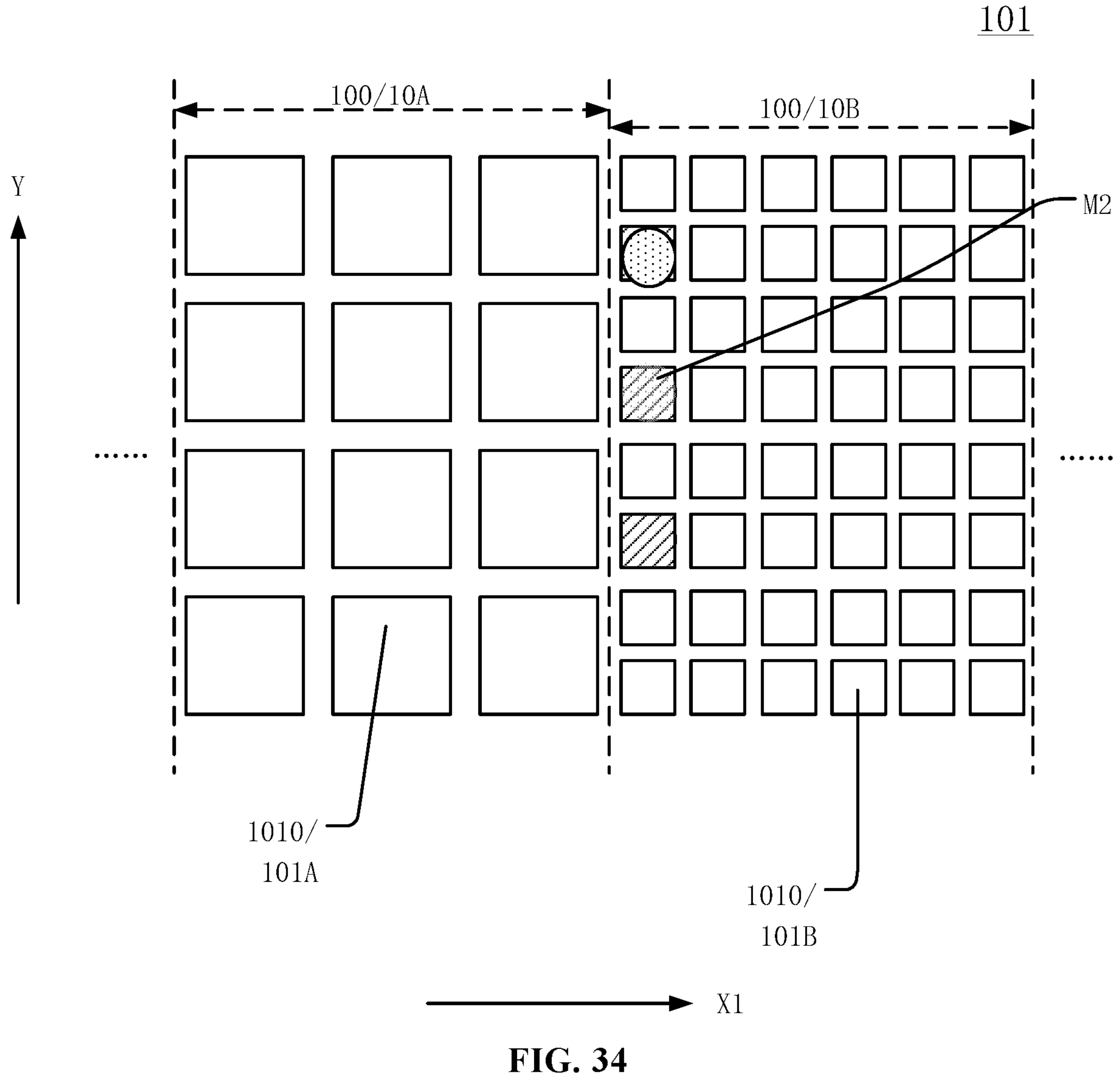

At S11, after the first droplet M1 moves to one first electrode 101A adjacent to the plurality of second electrodes 101B, the driving voltage of the first electrode 101A may be disconnected, a driving voltage may be provided for the plurality of second electrodes 101B, and the first droplet M1 may move on the plurality of second electrodes 101B and may be split into the plurality of second droplets M2. The size of the second droplet M2 may be less than the size of the first droplet M1, as shown in FIGS. 32-34.

The driving method provided in one embodiment may be used for the microfluidic apparatus 000 in above-mentioned embodiments to perform the operation of splitting large droplets into small droplets. The first droplet M1 may be disposed on the first electrode 101A of the first region 10A. By adjusting the voltage applied to the first electrode 101A in the first region 10A, the first droplet M1 may move along the first direction X1 (the direction X1 pointing from the first region 10A to the second region 10B). After moving to the second region 10B, the distance D2 between the first substrate 10 and the second substrate 20 may be less than the distance D1 between the first substrate 10 and the second substrate 20 in the first region 10A. By applying the driving voltage to the second electrode 101B, and relatively small distance D2 between the first substrate 10 and the second substrate 20, the first droplet M1 may be easily pinched off to be split into at least two second droplets M2. It can be understood that the droplet shown in FIGS. 31-34 only represents a possible size of the droplet moving to the position after being pinched off and does not represent the actual size of the droplet between the first substrate 10 and the second substrate 20.

Optionally, referring to FIGS. 31-35, FIG. 35 illustrates a flowchart of another driving method of a microfluidic apparatus according to various embodiments of the present disclosure. In one embodiment, the driving method may include following exemplary steps.

At S20, along the first direction X1 (the direction X1 pointing from the first region 10A to the second region 10B), the second electrode layer 201 may be connected to a ground signal, and the driving voltage may be provided to the first electrodes 101A sequentially. Optionally, a driving electric field for driving the first droplet M1 to move may be formed between the first electrode 101A of the driving voltage and the second electrode layer 201 of the ground signal; and driven by the electric field formed between the first electrode 101A and the second electrode layer 201, the first droplet M1 between the first substrate 10 and the second substrate 20 may move along the direction X1 pointing from the first region 10A to the second region 10B. As shown in FIG. 31, for the first electrode 101A to which the driving voltage needs to be applied when the first droplet M1 moves in the first region 10A may refer to the schematic of the first electrode 101A with filled pattern in FIG. 31. Furthermore, optionally, in FIG. 31, only one first droplet M1 is used as an example for illustration. During an implementation, the number of droplets for droplet operation in the microfluidic apparatus 000 may not be limited to one, and multiple first droplets M1 may be operated simultaneously. In one embodiment, only one first droplets M1 is used as an example for clear illustration.

At S21, after the first droplet M1 moves to one first electrode 101A adjacent to the plurality of second electrodes 101B, the driving voltage of the first electrode 101A may be disconnected, the driving voltage may be provided to the plurality of second electrodes 101B, and the first droplet M1 may move to a plurality of adjacent second electrodes 101B along the second direction Y. Along the direction in parallel with the plane of the first substrate 10, the first direction X1 may intersect the second direction Y. In one embodiment, the first direction X1 and the second direction Y may be perpendicular to each other as an example for illustration, as shown in FIGS. 32-33.

At S22, along the second direction Y, among the plurality of adjacent second electrodes 101B, the driving voltage may be provided to an A-th second electrode 101B, and the driving voltage for an (A+1)-th second electrode 101B may be disconnected. As shown in FIG. 34, the second electrode with filled pattern may be the A-th second electrode 101B with applied driving voltage. One elongated first droplet M1 may form the plurality of second droplets M2 on the A-th second electrode 101B, respectively. A is a positive integer, and the size of the second droplet M2 is smaller than the size of the first droplet M1, as shown in FIG. 34.

In one embodiment, it describes that when using the microfluidic apparatus 000 in above-mentioned embodiment to perform the droplet splitting process, the first droplet M1 with a relatively large size may first be elongated into a long droplet in the second region 10B and on the plurality of second electrodes 101B adjacent to the first region 10A; the elongated droplet may be split in the middle after alternatively (or at intervals) removing the driving voltage on the plurality of second electrodes 101B; and through the cooperation of relatively small distance D2 between the first substrate 10 and the second substrate 20, the first droplet M1 may be easily pinched off to be split into at least two second droplets M2, such that the first droplet M1 may be easier split into the plurality of second droplets M2 with relatively small sizes in the second region 10B.

In some optional embodiments, referring to FIGS. 4-29, and 36-40, FIG. 36 illustrates a flowchart of another driving method of a microfluidic apparatus according to various embodiments of the present disclosure; and FIGS. 37-40 illustrate schematics of a process of performing droplet merging using the driving method provided in FIG. 36. It can be understood that, in order to clearly illustrate the process of moving and merging droplets in one embodiment, only the electrodes in the electrode array layer that need to be applied with voltage during the moving process may be filled with patterns; and remaining floating electrodes in the electrode array layer may not be filled with patterns. The driving method provided in one embodiment may be applied to the microfluidic apparatus 000 in above-mentioned embodiments to perform droplet merging operation. It can be understood that, in one embodiment, the orthographic projection area of the first electrode 101A on the first substrate 10 and the orthographic projection area of the second electrode 101B on the first substrate 10 are different, which is taken as an example to illustrate the driving method. The driving method may include following exemplary steps.

Figure 37:
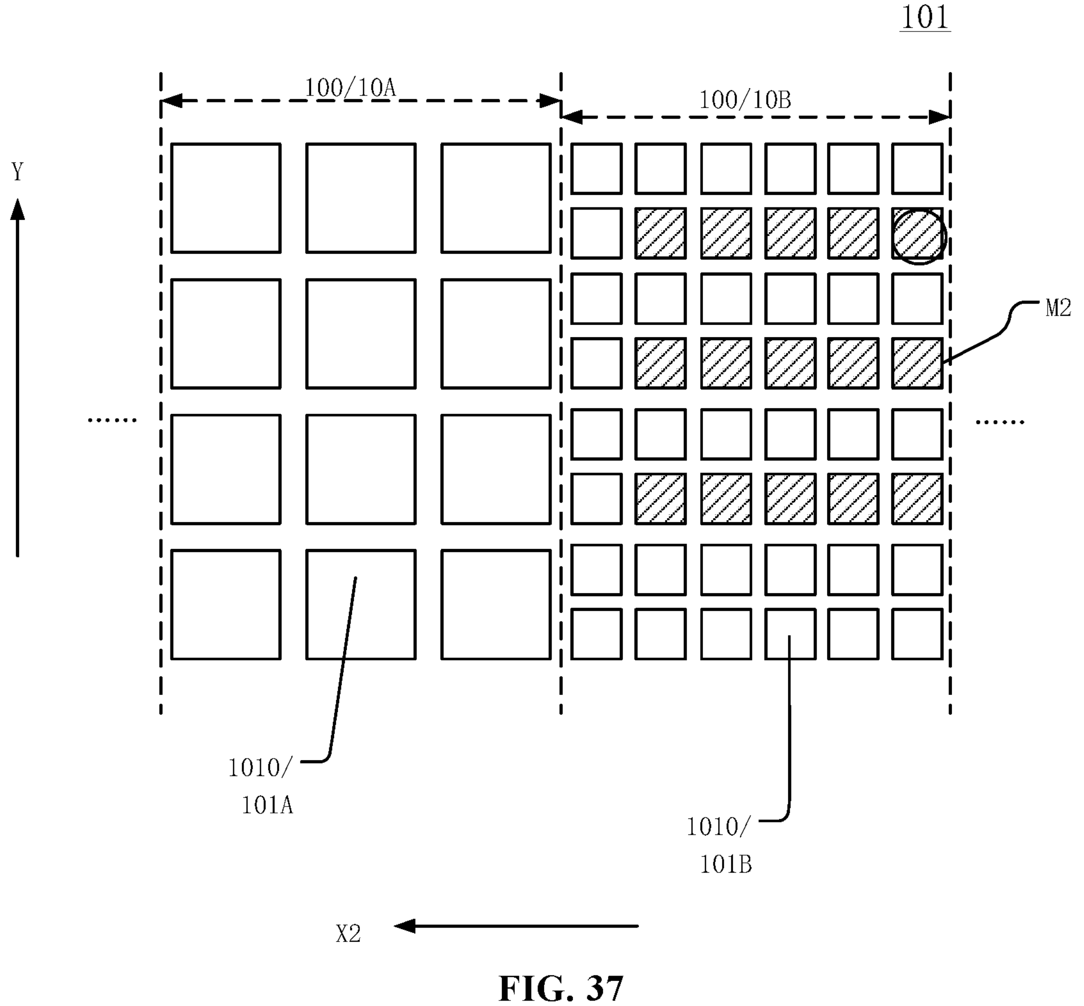
FIGS. 37-40 illustrate schematics of a process of performing droplet merging using a driving method provided in FIG. 36.

At S30, along the third direction X2 (the direction X2 pointing from the second region 10B to the first region 10A), the second electrode layer 201 may be connected a ground signal, and a driving voltage may be provided to the second electrodes 101B sequentially. Optionally, a driving electric field for driving the second droplet M2 to move may be formed between the second electrode 101B of the driving voltage and the second electrode layer 201 of the ground signal; and driven by the electric field formed between the second electrode 101B and the second electrode layer 201, the plurality of second droplets M2 between the first substrate 10 and the second substrate 20 may move along the direction X2 pointing from the second region 10B to the first region 10A, as shown in FIG. 37. Furthermore, optionally, in FIG. 37, only three second droplets M2 are used as an example for illustration. During an implementation, the number of droplets for droplet operation in the microfluidic apparatus 000 may not be limited to three, and multiple second droplets M2 may be operated simultaneously. In one embodiment, only three first droplets M2 are used as an example for clear illustration.

Figure 38:
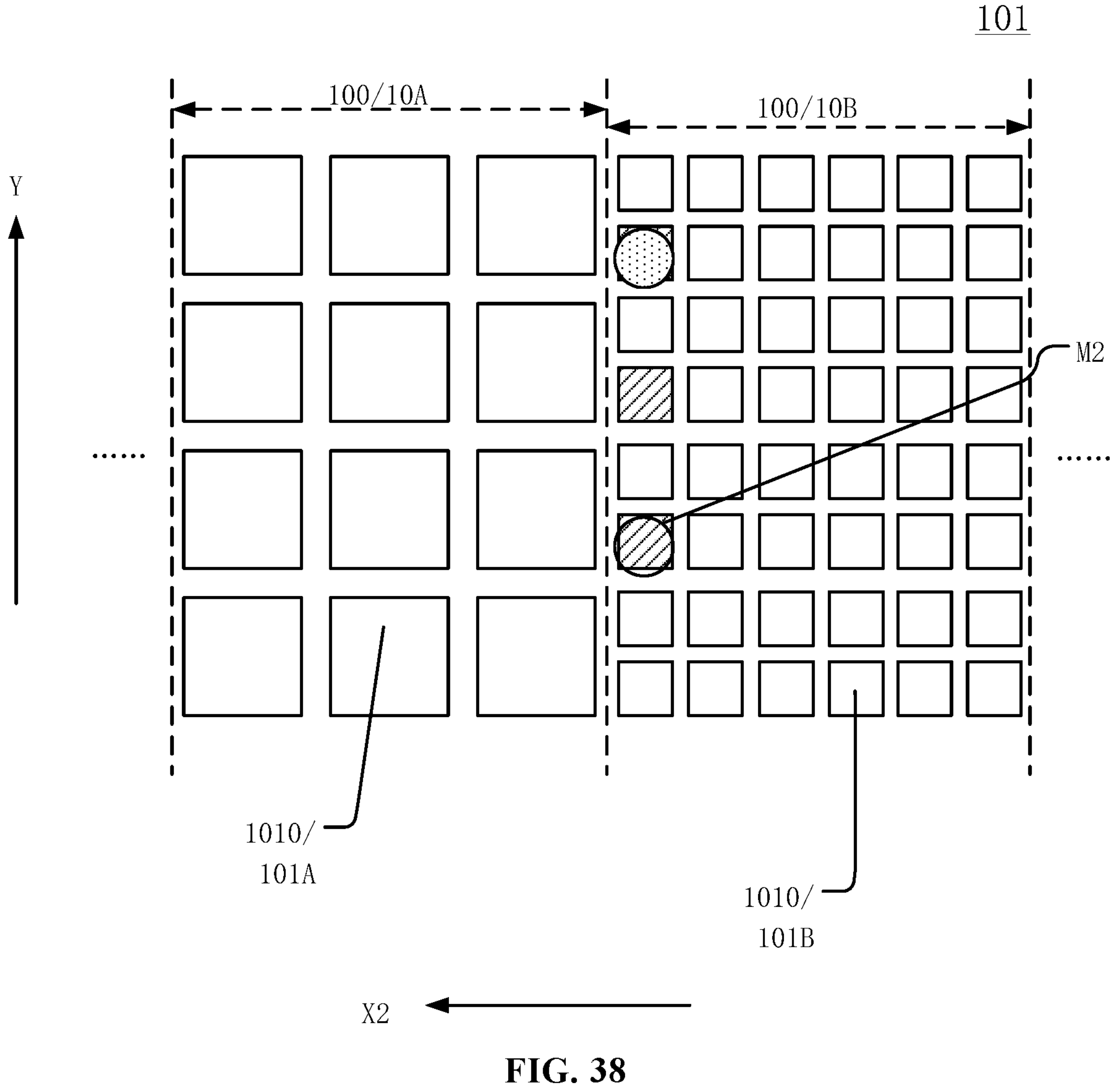
Figure 39:
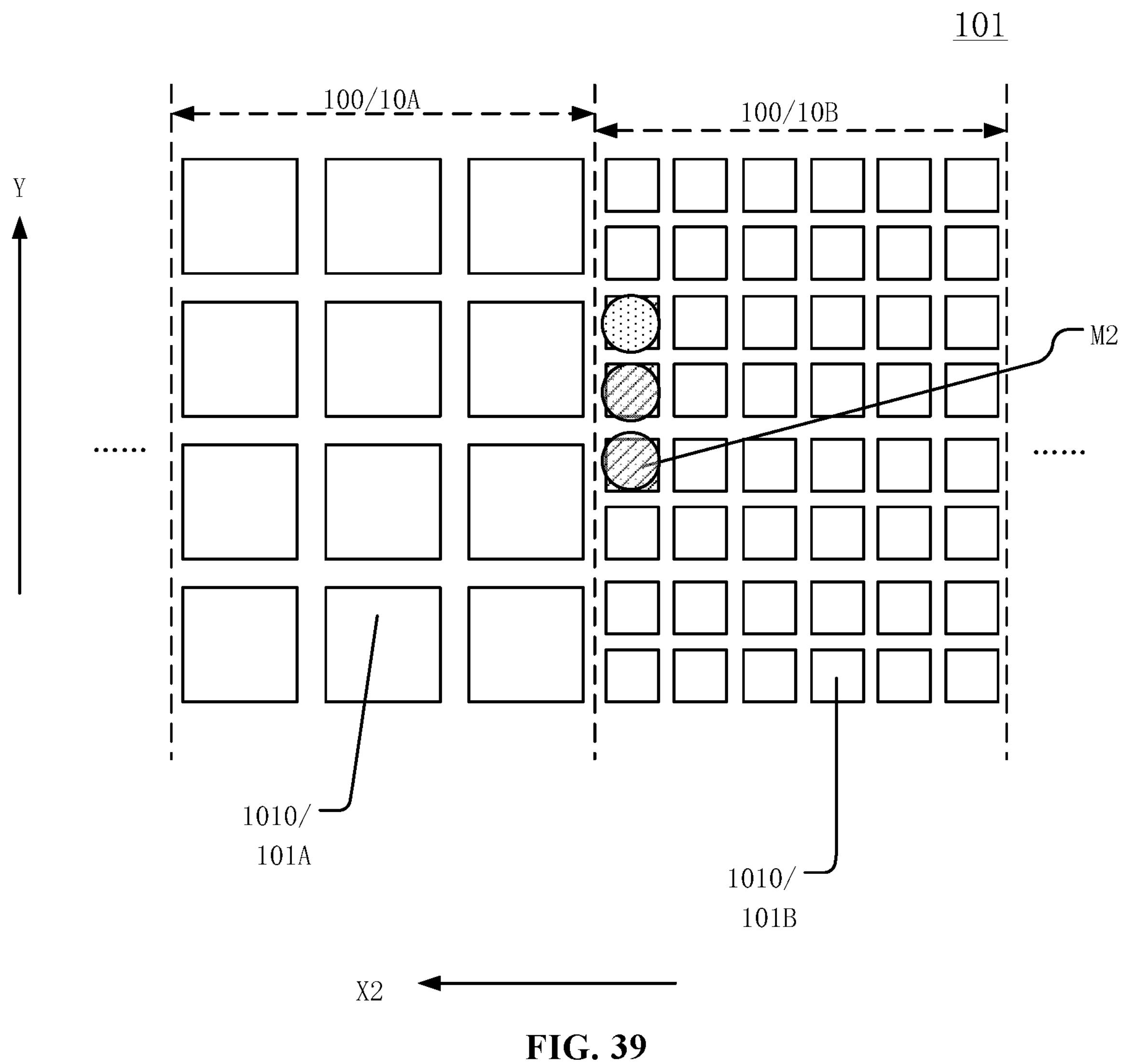
Figure 40:
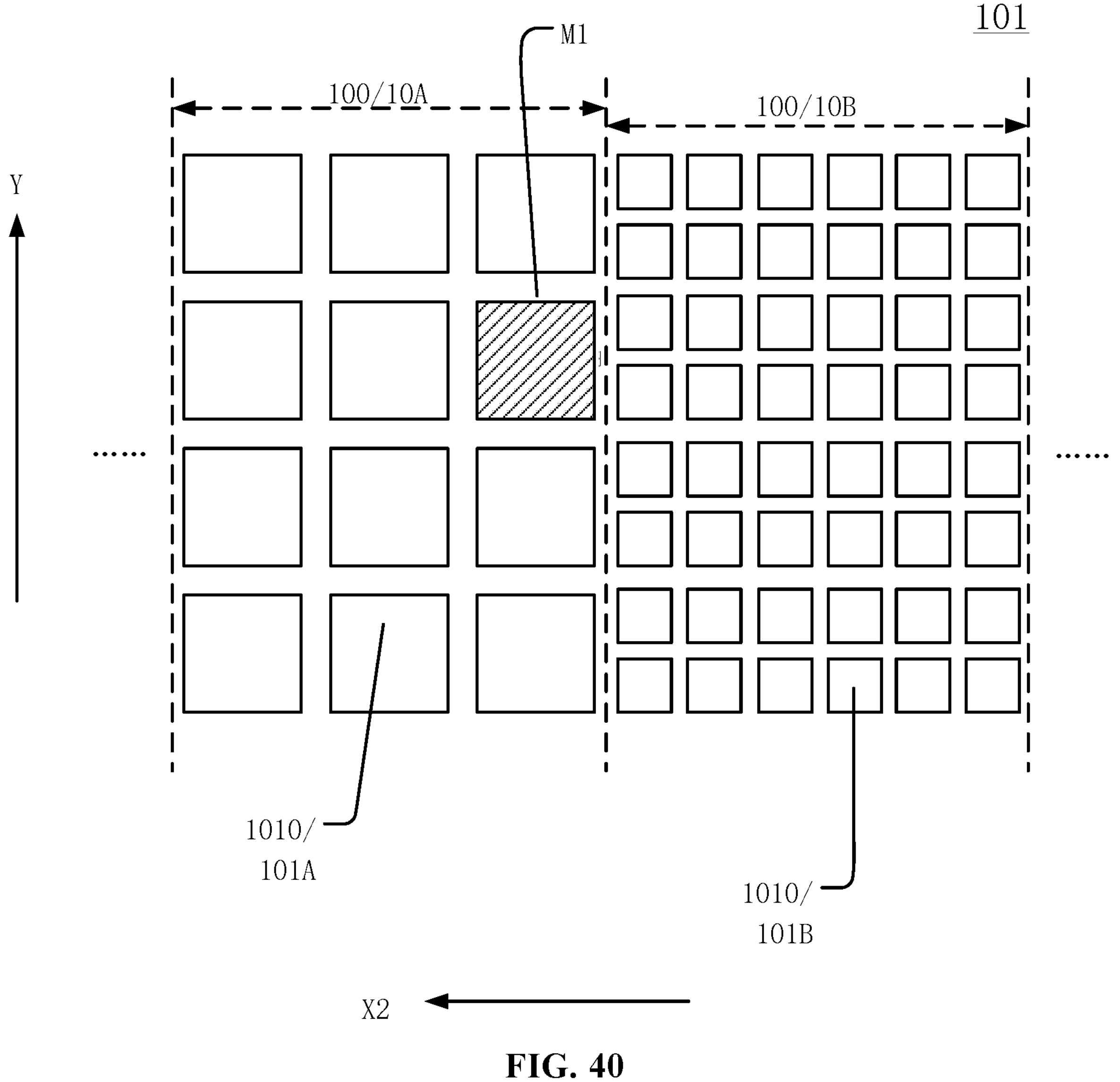

At S31, after the plurality of second droplets M2 move to the plurality of second electrodes 101B adjacent to the first electrode 101A, the driving voltage of the second electrodes 101B may be disconnected; a driving voltage may be provided to one first electrode 101A adjacent to the plurality of second electrodes 101B; and the plurality of second droplets M2 may move to the one first electrode 101A and aggregate on the first electrode 101A to form the first droplet M1. The size of the second droplet M2 may be smaller than the size of the first droplet M1, as shown in FIGS. 38-40.

The driving method provided in one embodiment may be used for the microfluidic apparatus 000 in above-mentioned embodiments to perform the operation of merging small droplets into large droplets. At least two second droplets M2 (three second droplets M2 as shown in FIGS. 38-40) may be disposed on the second electrodes 101B of the second region 10B; and by adjusting the voltage applied to the second electrodes 101B in the second region 10B, each second droplet M2 may move along the third direction X2 (the direction X2 pointing from the second region 10B to the first region 10A). After moving to the first region 10A, the driving voltage may be applied to the first electrodes 101A, and the distance D1 between the first substrate 10 and the second substrate 20 is greater than the distance D2 between the first substrate 10 and the second substrate 20 in the second region 10B. Therefore, relatively large distance D1 between the first substrate 10 and the second substrate 20 may provide a relatively large space, which facilitates desirable aggregation and sufficient merging of at least two second droplets M2 into a large-sized first droplet M1.

It should be noted that, the driving method in one embodiment is only illustrated by taking the first substrate 10 including the first region 10A and the second region 10B as an example. During an implementation, the first substrate 10 may further include more sub-regions 100, such that it may realize splitting large droplets into smaller droplets or merging small droplets to form larger droplets, which may refer to above-mentioned driving process of splitting one first droplet M1 into the plurality of second droplets M2 and merging the plurality of second droplets M2 into one first droplet M1 and may not be described in detail in one embodiment.

Figure 41:
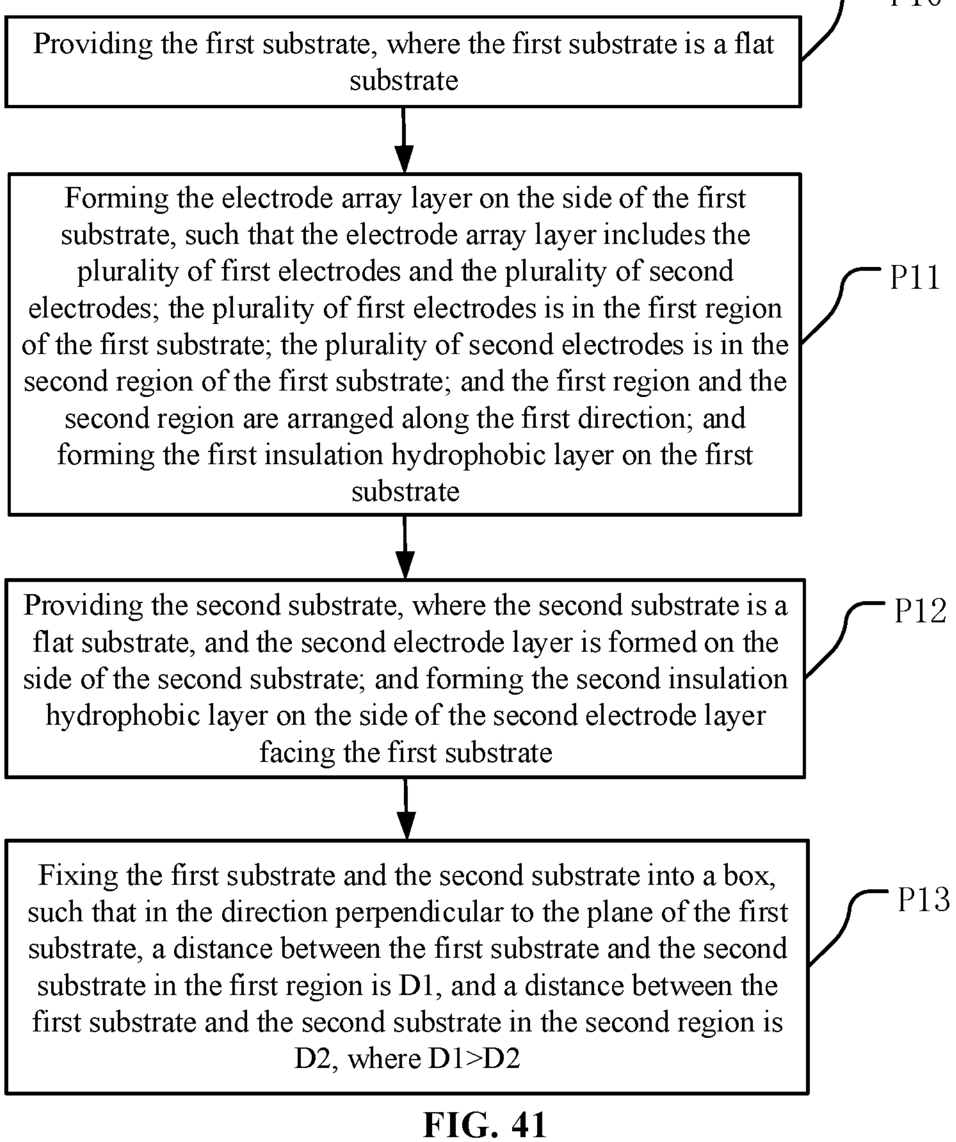
FIG. 41 illustrates a flowchart of a formation method of a microfluidic apparatus according to various embodiments of the present disclosure.
Figure 42:
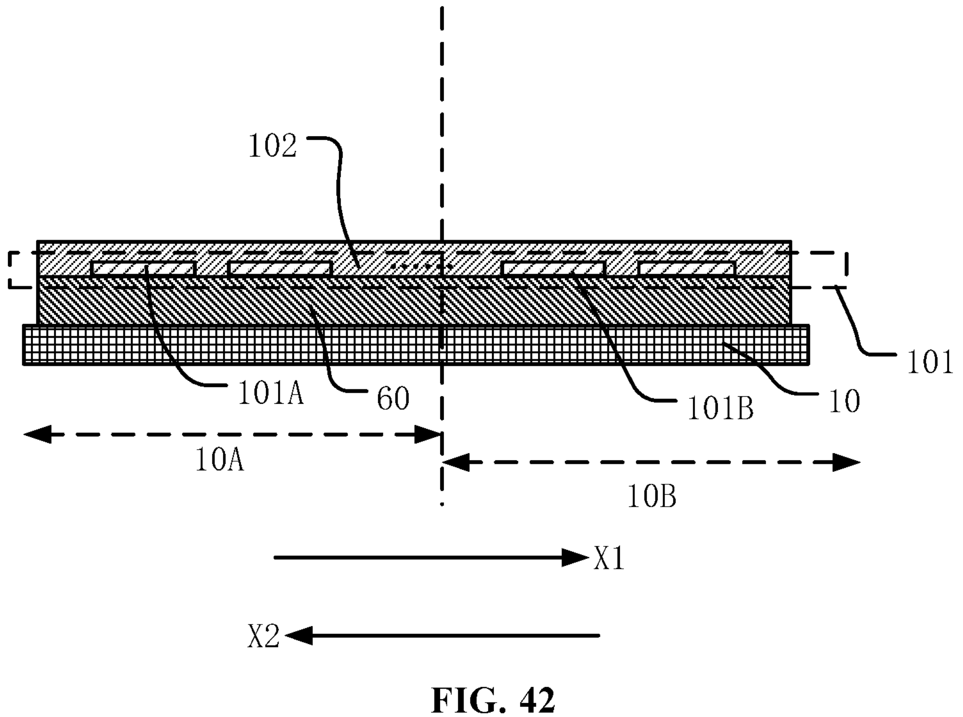
FIG. 42 illustrates a schematic of a first substrate and a structure on the first substrate before the first substrate and the second substrate are fixed to form a box in FIG. 41.
Figure 43:
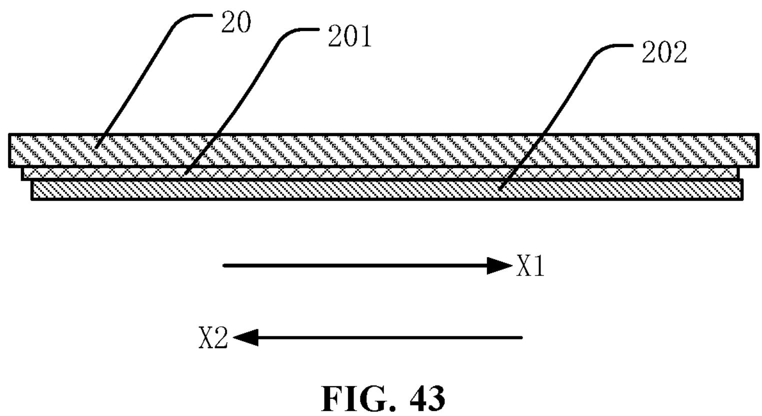
FIG. 43 illustrates a schematic of a second substrate and a structure on the second substrate after the first substrate and the second substrate are fixed to form a box in FIG. 41.
Figure 44:
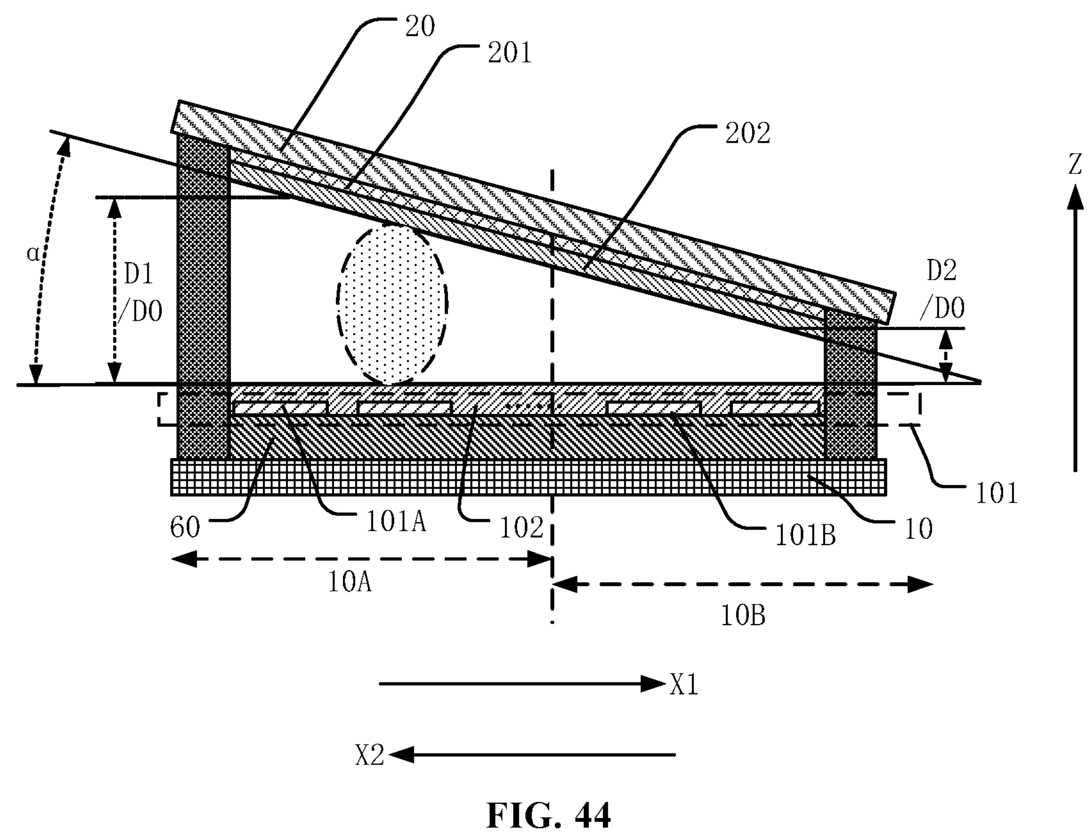
FIG. 44 illustrates a structural schematic of a box formed by fixing a first substrate with a second substrate in FIG. 41.
Figure 45:
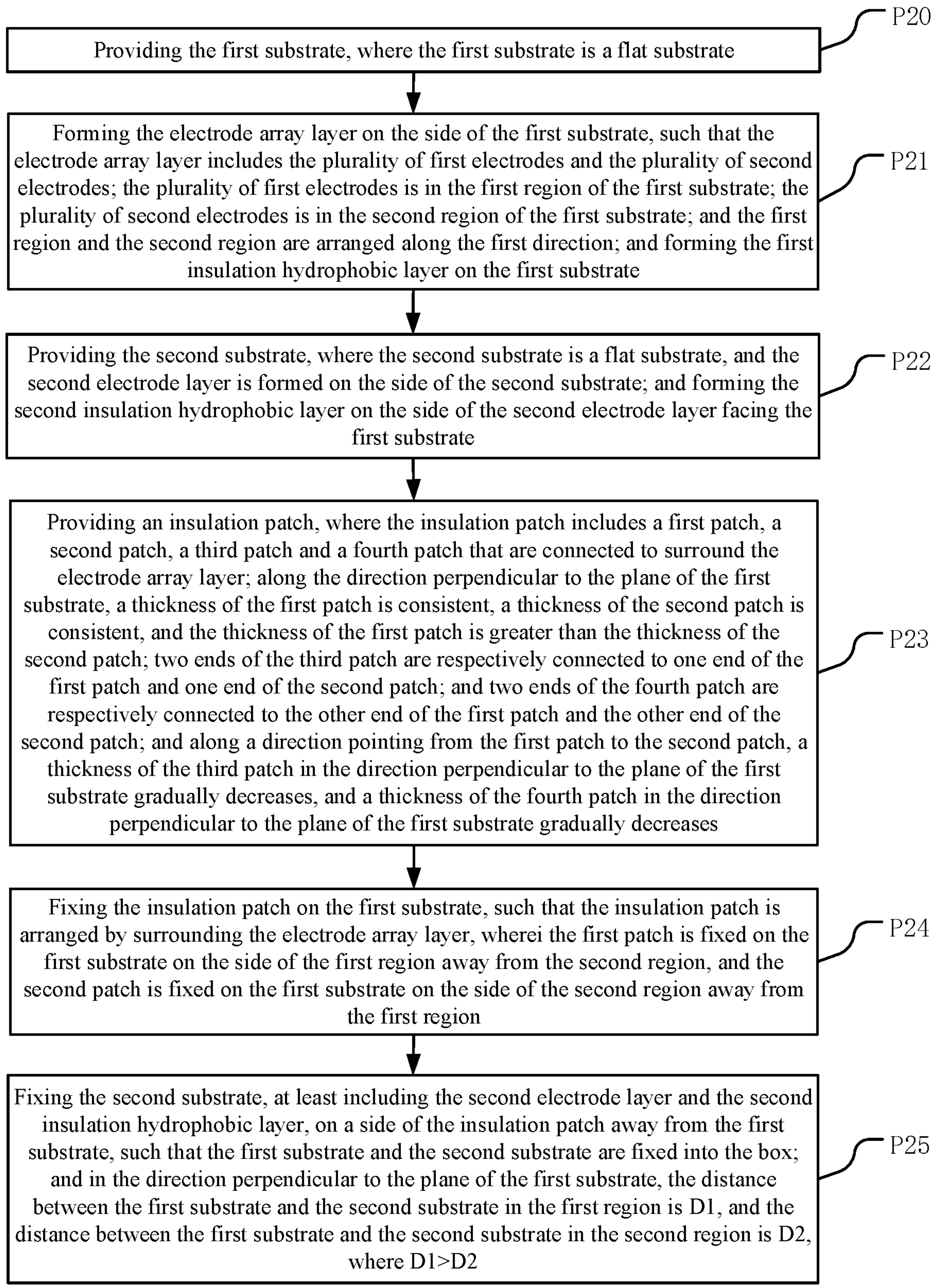
FIG. 45 illustrates a flowchart of another formation method of a microfluidic apparatus according to various embodiments of the present disclosure.

In some optional embodiments, referring to FIGS. 4-29, and 41-44, FIG. 41 illustrates a flowchart of a formation method of a microfluidic apparatus according to various embodiments of the present disclosure; FIG. 42 illustrates a schematic of the first substrate and a structure on the first substrate before the first substrate and the second substrate are fixed to form the box in FIG. 41; FIG. 43 illustrates a schematic of the second substrate and a structure on the second substrate after the first substrate and the second substrate are fixed to form the box in FIG. 41; and FIG. 44 illustrates a structural schematic of the box formed by fixing the first substrate with the second substrate in FIG. 41. The formation method provided in one embodiment may be used to form the microfluidic apparatus 000 in above-mentioned embodiments. In one embodiment, the formation method may include following exemplary steps.

At P10, the first substrate 10 may be provided, where the first substrate 10 is a flat substrate.

At P11, the electrode array layer 101 may be formed on the side of the first substrate 10, such that the electrode array layer 101 may include the plurality of first electrodes 101A and the plurality of second electrodes 101B. The plurality of first electrodes 101A may be in the first region 10A of the first substrate 10; the plurality of second electrodes 101B may be in the second region 10B of the first substrate 10; and the first region 10A and the second region 10B may be arranged along the first direction X1. Optionally, the first insulation hydrophobic layer 102 may also be disposed on the first substrate 10. The first insulation hydrophobic layer 102 may be disposed on the side of the electrode array layer 101 away from the first substrate 10 and may be used to insulate and isolate moisture, as shown in FIG. 42.

At P12, the second substrate 20 may be provided, where the second substrate 20 is a flat substrate, and the second electrode layer 201 may be formed on the side of the second substrate 20. Optionally, the second insulation hydrophobic layer 202 may be formed on the side of the second electrode layer 201 facing the first substrate 10, and may be used to insulate and isolate moisture, as shown in FIG. 43.

At P13, the first substrate 10 and the second substrate 20 may be fixed to form the box, such that in the direction Z perpendicular to the plane of the first substrate 10, the distance between the first substrate 10 and the second substrate 20 in the first region 10A is D1, and the distance between the first substrate 10 and the second substrate 20 in the second region 10B is D2, where D1>D2, as shown in FIG. 44.

In the formation method of one embodiment, provided first substrate 10 and second substrate 20 may both be flat substrates, that is, the first substrate 10 and the second substrate 20 may be hard glass substrates. Flat substrates may be that entire region of the first substrate 10 and the entire region of the second substrate 20 are flat without bending parts, which may be beneficial for reducing the difficulty of forming the electrode structures on the flat substrates. In the formation method of one embodiment, the manner of fixing the first substrate 10 and the second substrate 20 in the box may be through frame adhesive or other sealing manners, which may not be limited in one embodiment. The fixing manner may only need to satisfy requirements of desirable sealing and stability after the first substrate 10 and the second substrate 20 are fixed to form the box and may also make that in the direction Z perpendicular to the plane of the first substrate 10, the distance D1 between the first substrate 10 and the second substrate 20 in the first region 10A is greater than the distance D2 between the first substrate 10 and the second substrate 20 in the second region 10B. That is, the first substrate 10 and the second substrate 20, which are flat structures, may be directly disposed to be opposite to each other at a certain angle, which may achieve different cell thicknesses in different regions. The distance D1 between the first substrate 10 and the second substrate 20 in the first region 10A may be relatively large, and the distance D2 between the first substrate 10 and the second substrate 20 in the second region 10B may be relatively small, thereby being matched with droplets of different sizes to facilitate different droplet operations. In the microfluidic apparatus 000 of one embodiment, the flat first substrate 10 and the second substrate 20 may be obliquely and directly disposed to be opposite to each other at a certain angle, which may avoid using a flexible substrate to achieve different cell thicknesses resulting in increased process difficulty. In such way, the process may not only be simple, and different cell thicknesses of different regions may also be directly realized through a flat hard substrate, which may be compatible with driving droplets of different sizes, thereby realizing the operation of driving droplets of different sizes and splitting or merging droplets of different sizes and being beneficial for optimizing operational performance. Droplet merging may be realized in the position of the large cell thickness, so that the droplet merging may be more sufficient and efficient; and the droplet splitting may be realized at the position of the small cell thickness, so that the droplet splitting may be more stable and reliable.

Figure 46:
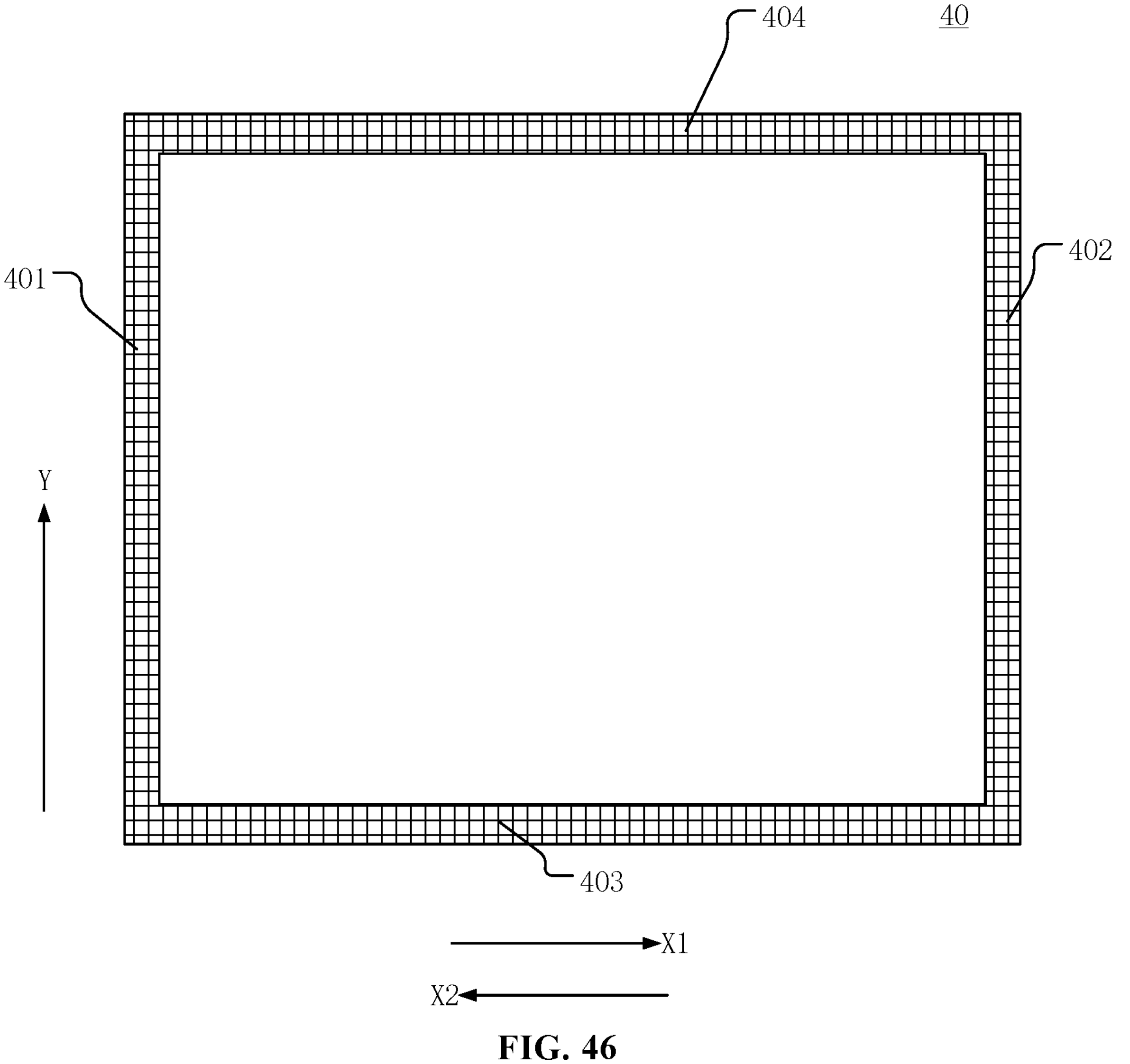
FIG. 46 illustrates a top structural view of an insulation patch provided in FIG. 45.
Figure 47:
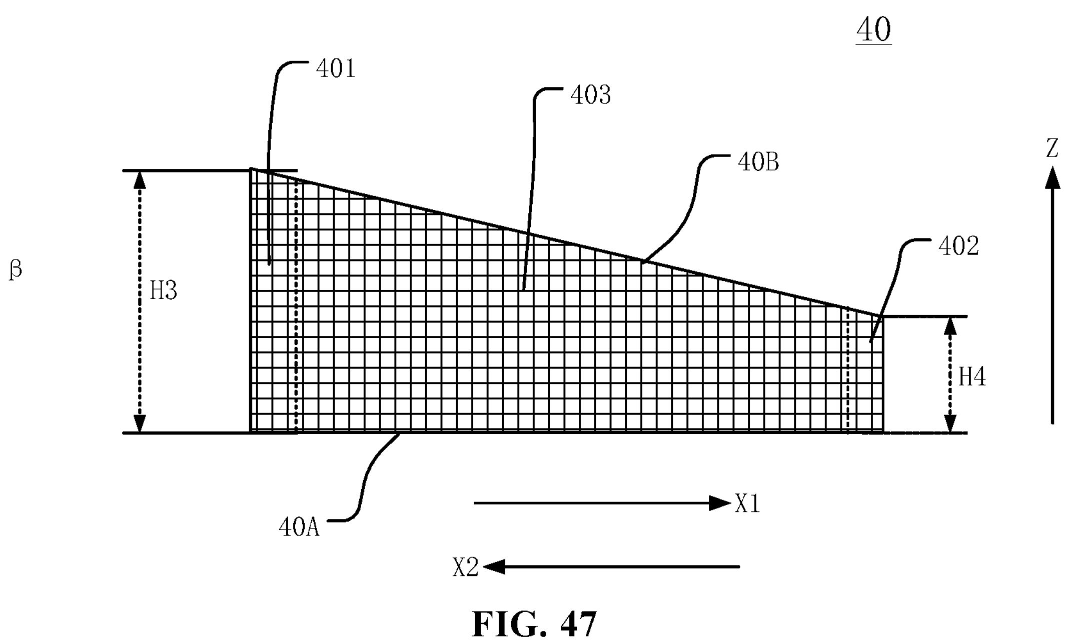
FIG. 47 illustrates a front structural view of an insulation patch in FIG. 46.
Figure 48:
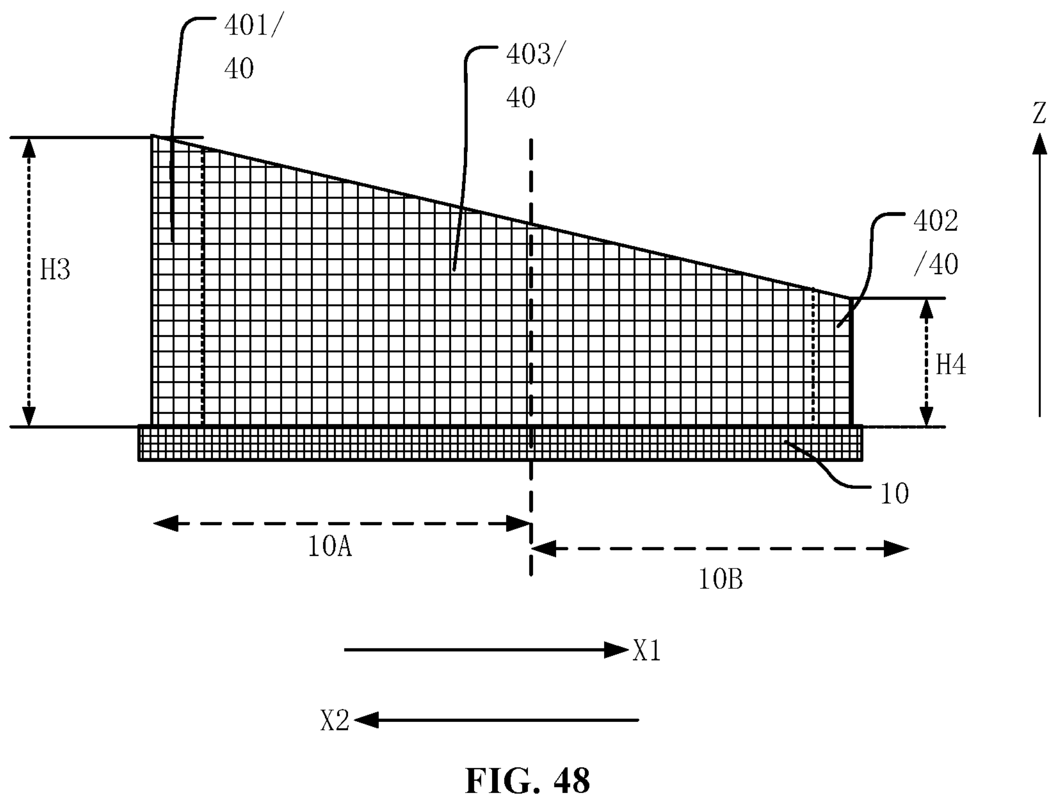
FIG. 48 illustrates a schematic after an insulation patch is fixed on a first substrate in FIG. 45.
Figure 49:
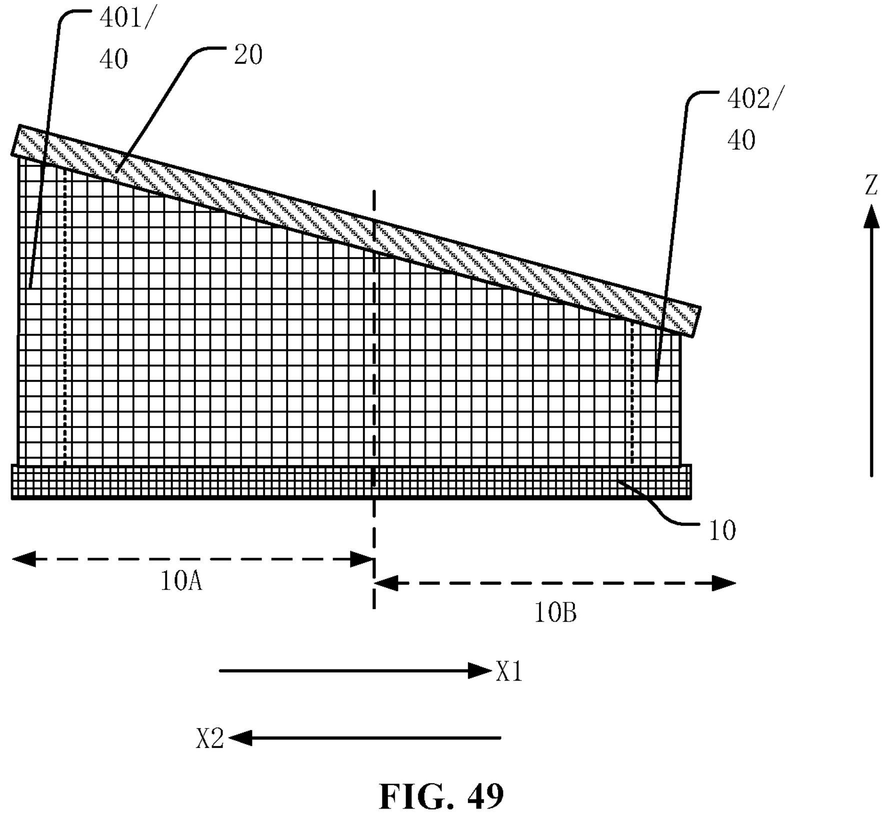
FIG. 49 illustrates a structural schematic after a first substrate and a second substrate are fixed to form a box using an insulation patch in FIG. 45.
Figure 50:
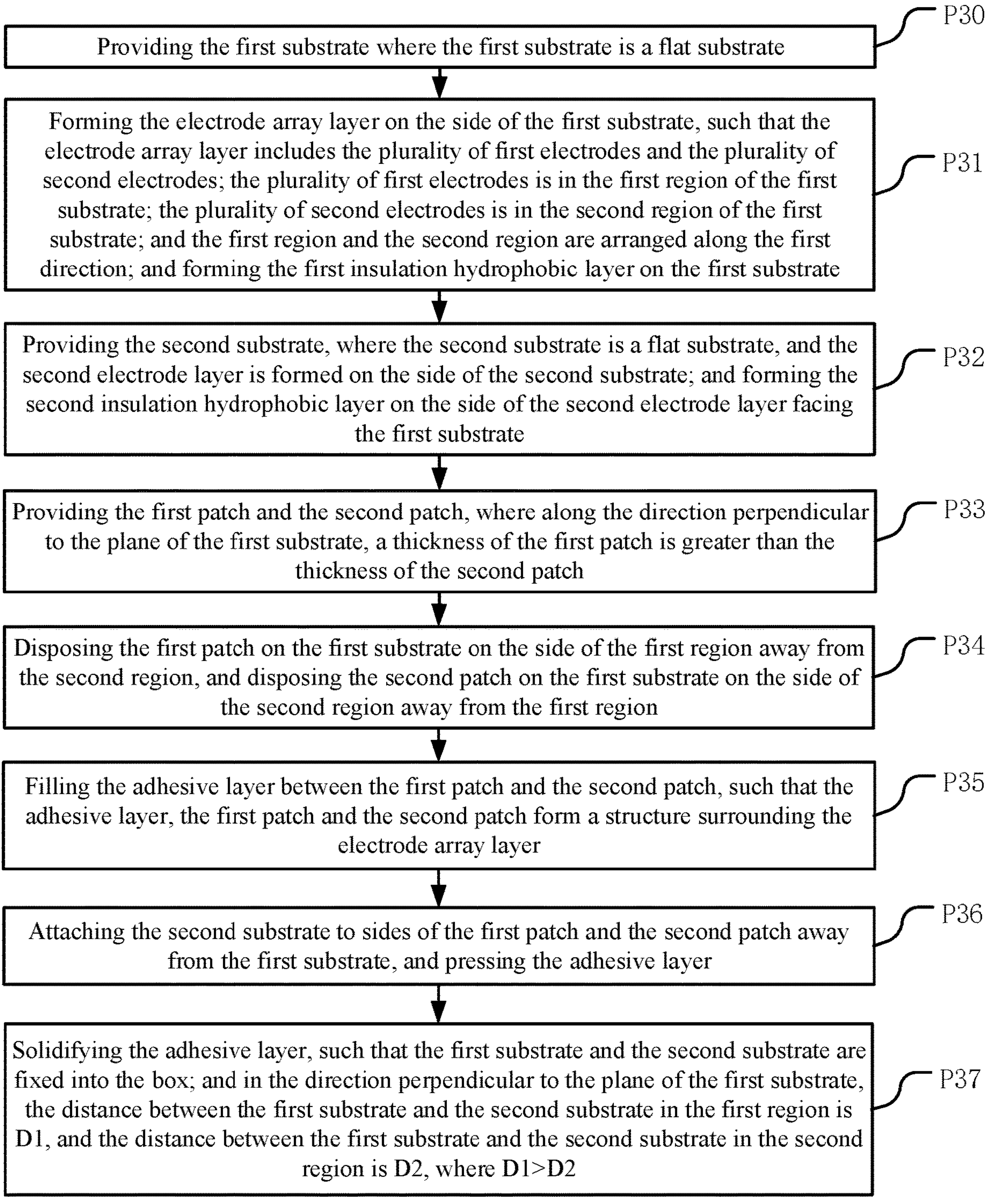
FIG. 50 illustrates a flowchart of another formation method of a microfluidic apparatus according to various embodiments of the present disclosure.

In some optional embodiments, referring to FIGS. 42-43, and 45-49, FIG. 45 illustrates a flowchart of another formation method of a microfluidic apparatus according to various embodiments of the present disclosure; FIG. 46 illustrates a top structural view of the insulation patch provided in FIG. 45; FIG. 47 illustrates a front structural view of the insulation patch in FIG. 46; FIG. 48 illustrates a schematic after the insulation patch is fixed on the first substrate in FIG. 45; and FIG. 49 illustrates a structural schematic after the first substrate and the second substrate are fixed to form the box using the insulation patch in FIG. 45. In one embodiment, the formation method may include following exemplary steps.

At P20, the first substrate 10 may be provided, where the first substrate 10 is a flat substrate.

At P21, the electrode array layer 101 may be formed on the side of the first substrate 10, such that the electrode array layer 101 may include the plurality of first electrodes 101A and the plurality of second electrodes 101B. The plurality of first electrodes 101A may be in the first region 10A of the first substrate 10; the plurality of second electrodes 101B may be in the second region 10B of the first substrate 10; and the first region 10A and the second region 10B may be arranged along the first direction X1. Optionally, the first insulation hydrophobic layer 102 may also be disposed on the first substrate 10. The first insulation hydrophobic layer 102 may be disposed on the side of the electrode array layer 101 away from the first substrate 10 and may be used to insulate and isolate moisture, as shown in FIG. 42.

At P22, the second substrate 20 may be provided, where the second substrate 20 is a flat substrate, and the second electrode layer 201 may be formed on the side of the second substrate 20. Optionally, the second insulation hydrophobic layer 202 may be formed on the side of the second electrode layer 201 facing the first substrate 10, and may be used to insulate and isolate moisture, as shown in FIG. 43.

At P23, an insulation patch 40 may be provided. The insulation patch 40 may include a first patch 401, a second patch 402, a third patch 403 and a fourth patch 404 that are connected to surround the electrode array layer. In the direction Z perpendicular to the plane of the first substrate 10, the thickness H3 of the first patch 401 may be consistent, the thickness H4 of the second patch 402 may be consistent, and the thickness H3 of the first patch 401 may be greater than the thickness H4 of the second patch 402. Two ends of the third patch 403 may be respectively connected to one end of the first patch 401 and one end of the second patch 402; and two ends of the fourth patch 404 may be respectively connected to the other end of the first patch 401 and the other end of the second patch 402. Along the direction from the first patch 401 to the second patch 402, the thickness of the third patch 403 in the direction Z perpendicular to the plane of the first substrate 10 may gradually decrease, and the thickness of the fourth patch 404 in the direction Z perpendicular to the plane of the first substrate 10 may gradually decrease, as shown in FIGS. 46 and 47.

At P24, the insulation patch 40 may be fixed on the first substrate 10, such that the insulation patch 40 may be arranged around the electrode array layer 101. The first patch 401 may be fixed on the first substrate 10 on the side of the first region 10A away from the second region 10B, and the second patch 402 may be fixed on the first substrate 10 on the side of the second region 10B away from the first region 10A (fixed by double-sided tape or a thin layer of coated liquid glue, not shown in FIGS. 42-43, and 45-49), as shown in FIG. 48.

At P25, the second substrate 20 at least including the second electrode layer 201 and the second insulation hydrophobic layer 202 (fixed by double-sided tape or a thin layer of coated liquid glue, not shown in FIGS. 42-43, and 45-49) may be fixed on the side of the insulation patch 40 away from the first substrate 10. In such way, the first substrate 10 and the second substrate 20 may be fixed to form the box; and in the direction Z perpendicular to the plane of the first substrate 10, the distance between the first substrate 10 and the second substrate 20 in the first region 10A is D1, and the distance between the first substrate 10 and the second substrate 20 in the second region 10B is D2, where D1>D2, as shown in FIG. 49.

In one embodiment, four patches may integrally surround to form one insulation patch 40; and the first substrate 10 and the second substrate 20 may be sealed into the box through the prefabricated insulation patch 40, which may be beneficial for ensuring the overall stability and sealing of the microfluidic apparatus 000. Single-piece insulation patch 40 formed by the first patch 401, the second patch 402, the third patch 403 and the fourth patch 404 may be directed attached on the first substrate 10, which may be beneficial for further simplifying the process of forming the first substrate 10 and the second substrate 20 into the box and effectively reducing formation difficulty.

Optionally, referring to FIGS. 46-47, in one embodiment, the insulation patch 40 may include a first surface 40A facing the side of the first substrate 10 and a second surface 40B facing the side of the second substrate 20; and the angle formed between the plane where the first surface 40A is located and the plane where the second surface 40B is located is β, where 10°≤β≤30°. That is, by setting that the angle β formed between the first surface 40A of the insulation patch 40 facing the side of the first substrate 10 and the second surface 40B facing the side of the second substrate 20 satisfies 10°≤β≤30°, after the first substrate 10 and the second substrate 20 are fixed to form the box, the first substrate 10 and the second substrate 20 which are flat structures may be directly disposed to be opposite to each other to form an angle α of a certain size, which may ensure that the range of the angle α can be 10°≤α≤30°. Therefore, it avoids that excessively large angle α formed by the first substrate 10 and the second substrate 20 may make the distance D1 between the first substrate 10 and the second substrate 20 in the first region 10A to be excessively large which may cause that the space size between the first substrate 10 and the second substrate 20 changes too slowly and the droplet change process is too slow, resulting in that the droplet splitting and merging effect is not obvious, thereby affecting usage effect. In addition, it can also avoid that if the angle α is excessively small, the space size between the first substrate 10 and the second substrate 20 changes too quickly, and the movable range of the droplet in the second region 10B is excessively small, thereby affecting usage effect.

Figure 51:
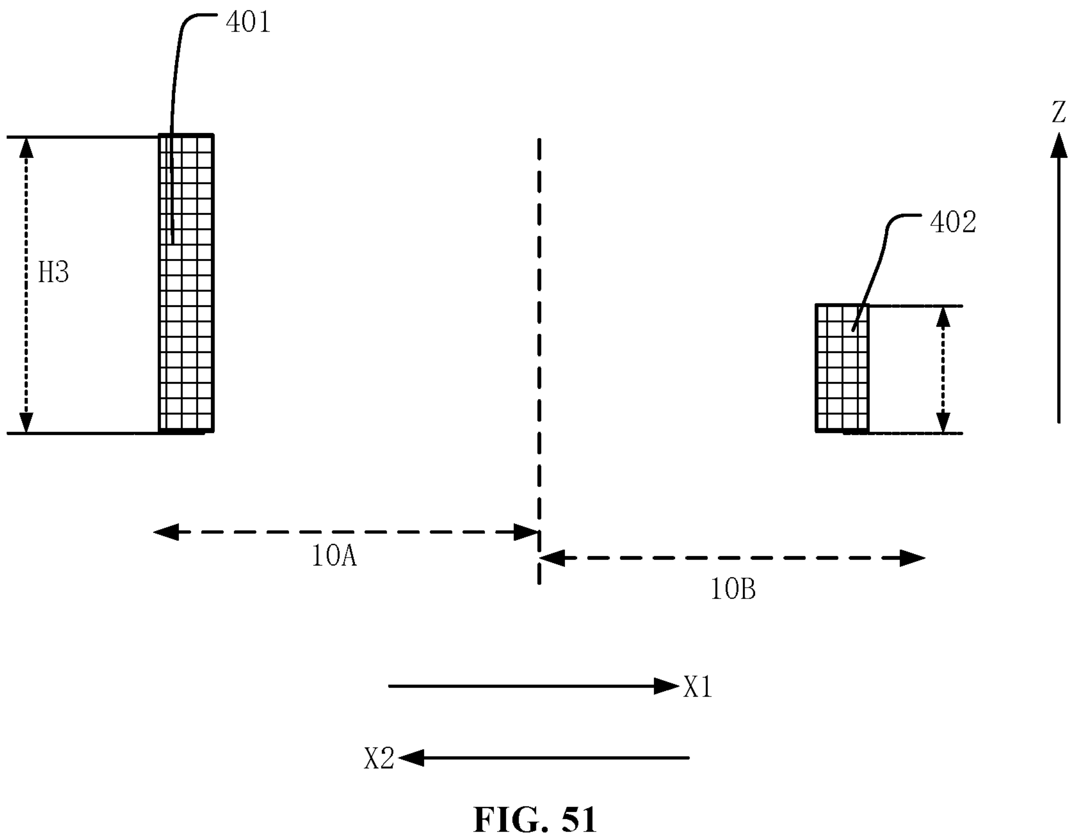
FIG. 51 illustrates a front structural view of a first patch and a second patch provided in FIG. 50.
Figure 52:
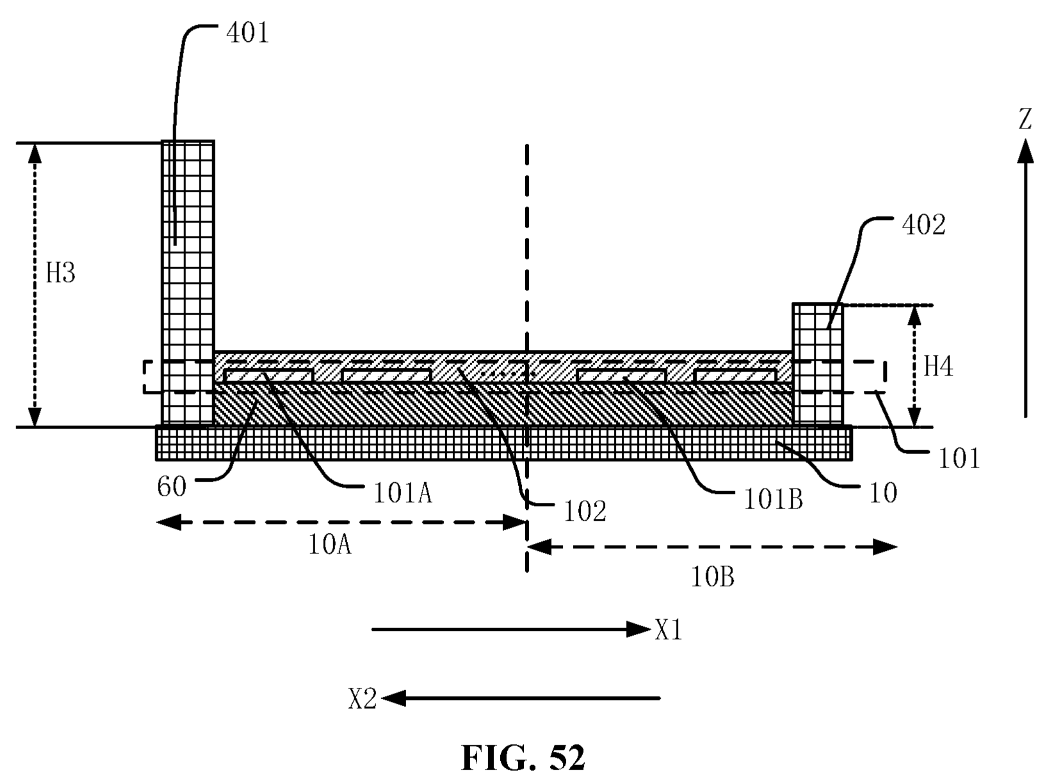
FIG. 52 illustrates a structural schematic after fixing a first patch and a second patch on a first substrate in FIG. 50.
Figure 53:
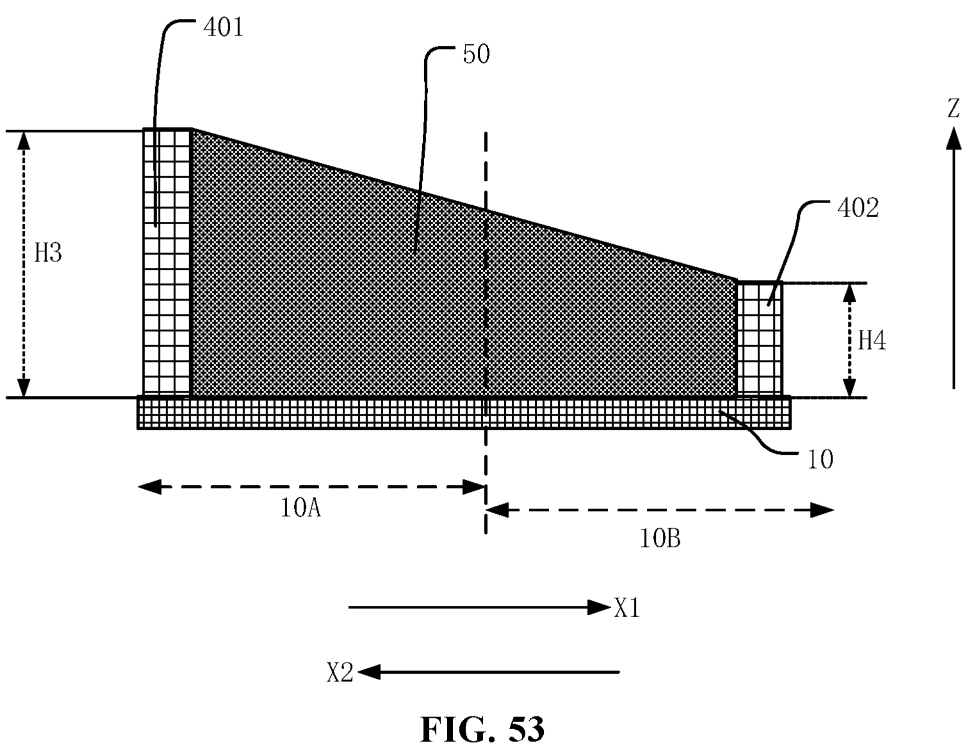
FIG. 53 illustrates a structural schematic after filling an adhesive layer between a first patch and a second patch on a first substrate in FIG. 50.
Figure 54:
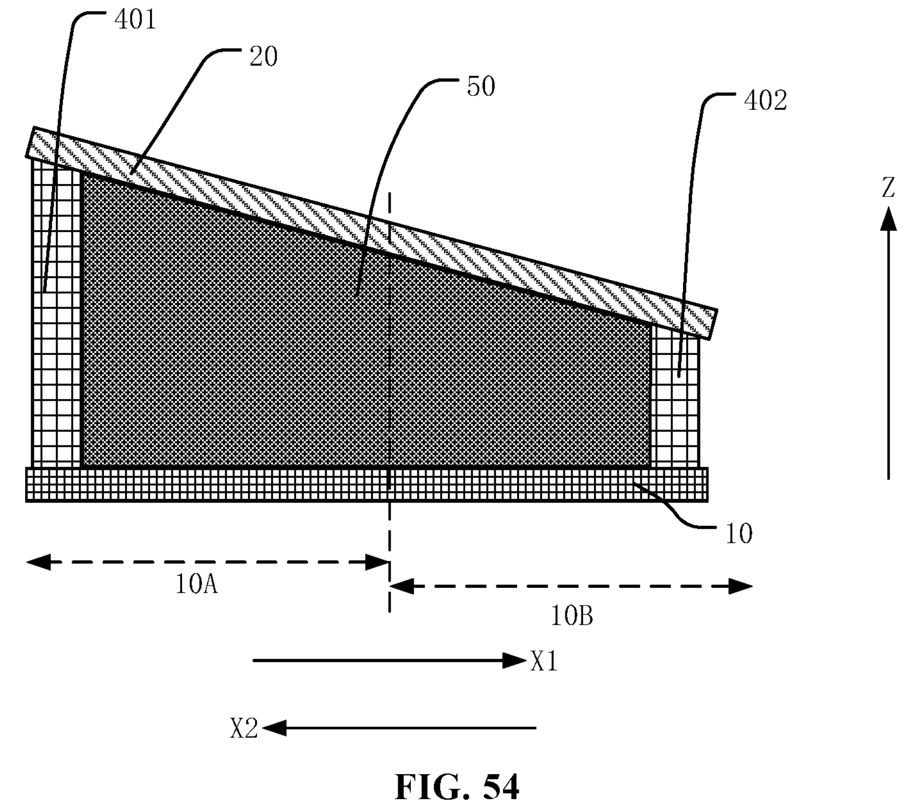
FIG. 54 illustrates a structural schematic after a first substrate and a second substrate are fixed to form a box in FIG. 50.

In some optional embodiments, referring to FIGS. 42-43 and 50-53, FIG. 50 illustrates a flowchart of another formation method of a microfluidic apparatus according to various embodiments of the present disclosure; FIG. 51 illustrates a front structural view of the first patch and the second patch provided in FIG. 50; FIG. 52 illustrates a structural schematic after fixing the first patch and the second patch on the first substrate in FIG. 50; FIG. 53 illustrates a structural schematic after filling an adhesive layer between the first patch and the second patch on the first substrate in FIG. 50; and FIG. 54 illustrates a structural schematic after the first substrate and the second substrate are fixed to form the box in FIG. 50. In one embodiment, the formation method may include following exemplary steps.

At P30, the first substrate 10 may be provided, where the first substrate 10 is a flat substrate.

At P31, the electrode array layer 101 may be formed on the side of the first substrate 10, such that the electrode array layer 101 may include the plurality of first electrodes 101A and the plurality of second electrodes 101B. The plurality of first electrodes 101A may be in the first region 10A of the first substrate 10; the plurality of second electrodes 101B may be in the second region 10B of the first substrate 10; and the first region 10A and the second region 10B may be arranged along the first direction X1. Optionally, the first insulation hydrophobic layer 102 may also be disposed on the first substrate 10. The first insulation hydrophobic layer 102 may be disposed on the side of the electrode array layer 101 away from the first substrate 10 and may be used to insulate and isolate moisture, as shown in FIG. 42.

At P32, the second substrate 20 may be provided, where the second substrate 20 is a flat substrate, and the second electrode layer 201 may be formed on the side of the second substrate 20. Optionally, the second insulation hydrophobic layer 202 may be formed on the side of the second electrode layer 201 facing the first substrate 10, and may be used to insulate and isolate moisture, as shown in FIG. 43.

At P33, the first patch 401 and the second patch 402 may be provided. In the direction Z perpendicular to the plane of the first substrate 10, the thickness H3 of the first patch 401 may be greater than the thickness H4 of the second patch 402, as shown in FIG. 51.

At P34, the first patch 401 may be disposed on the first substrate 10 on the side of the first region 10A away from the second region 10B, and the second patch 402 may be disposed on the first substrate 10 on the side of the second region 10B away from the first region 10A, as shown in FIG. 52.

At P35, the adhesive layer 50 may be filled between the first patch 401 and the second patch 402, so that the adhesive layer 50, the first patch 401, and the second patch 402 may form a structure disposed by surrounding the electrode array layer 101. Optionally, when the adhesive layer 50 is filled, non-uniform glue coating may be performed in a stagewise manner (e.g., one stage after another). A relatively large amount of the adhesive layer 50 may be filled in the position where a large cell thickness is needed, and a relatively small amount of the adhesive layer 50 may be filled in the position where a small cell thickness is needed, as shown in FIG. 53.

At P36, the second substrate 20 may be attached to the sides of the first patch 401 and the second patch 402 away from the first substrate 10, and the adhesive layer 50 may be pressed, as shown in FIG. 54.

At P37, the adhesive layer 50 may be solidified to fix the first substrate 10 and the second substrate 20 in the box, such that in the direction Z perpendicular to the plane of the first substrate 10, the distance between the first substrate 10 and the second substrate 20 in the first region 10A is D1, and the distance between the first substrate 10 and the second substrate 20 in the second region 10B is D2; where D1>D2, as shown in FIG. 54.

In one embodiment, it describes that the box forming process of fixing the first substrate 10 with the second substrate 20 may be achieved through two independent patches including the first patch 401 and the second patch 402. Along the first direction X1, the first patch 401 and the second patch 402 may be on two opposite sides of the electrode array layer 101, respectively. The first patch 401 may be on the side of the first region 10A away from the second region 10B, and the second patch 402 may be on the side of the second region 10B away from the first region 10A. In the direction Z perpendicular to the plane of the first substrate 10, the thickness H3 of the first patch 401 may be consistent, the thickness H4 of the second patch 402 may be consistent, and the thickness H3 of the first patch 401 may be greater than the thickness H4 of the second patch 402. After the electrode array layer 101 and other structures are formed on the first substrate 10, the first patch 401 and the second patch 402 may be respectively disposed on the outer contour of the first substrate 10; the surfaces of the first patch 401 and the second patch 402 facing the first substrate 10 may be fixed to the first substrate 10 by liquid glue or double-sided tape (not shown); a gradient opposite to the second substrate 20 may be pre-formed on the first substrate 10 by the first patch 401 and the second patch 402 with different thicknesses; and the ends of the first patch 401 and the second patch 402 may be connected by filling the adhesive layer 50 at the periphery of the electrode array layer 101. Finally, the first patch 401, the second patch 402, and the adhesive layer 50 may form a frame body structure surrounding the electrode array layer 101. The second substrate 20 with formed second electrode layer 201 and other structures may be directly and oppositely attached to the surfaces of the first patch 401 and the second patch 402 on the side away from the first substrate 10, thereby forming the cavity for accommodating droplets. After the attaching process, the first substrate 10 and the second substrate 20 may directly form the angle α. In such way, it may be beneficial for ensuring the overall stability and sealing of the microfluidic apparatus 000 and simplifying the process of forming box using the first substrate 10 and the second substrate 20 through directly attaching the first patch 401 and the second patch 402 on the first substrate 10, thereby reducing formation difficulty.

It can be understood that, in one embodiment, the side surface of the first patch 401 facing the first substrate 10 and the side surface of the second patch 402 facing the first substrate 10 may be on a same horizontal plane, which may further be beneficial for ensuring the flatness between the first patch 401 and the first substrate 10 and between the second patch 402 and the first substrate 10 after the fixing and attaching process.

From the above-mentioned embodiments, it may be seen that the microfluidic apparatus, its driving method and formation method provided by the present disclosure may achieve at least following beneficial effects.

The microfluidic apparatus provided by the present disclosure may include the first substrate and the second substrate which are oppositely disposed; and in the direction perpendicular to the plane of the first substrate, the distance D1 between the first substrate and the second substrate in the first region may be greater than the distance D2 between the first substrate and the second substrate in the second region. That is, the first substrate and the second substrate which are flat structures may be directly and oppositely disposed at a certain angle to achieve different cell thicknesses in different regions. The distance D1 between the first substrate and the second substrate in the first region may be relatively large, and the distance D2 between the first substrate and the second substrate in the second region may be relatively small, thereby being matched with droplets of different sizes and beneficial for different droplet operations. When the microfluidic apparatus provided by the present disclosure performs the operation of splitting large droplets into small droplets, the distance D2 between the first substrate and the second substrate in the second region may be less than the distance D1 between the first substrate and the second substrate in the first region; furthermore, relatively small distance D2 between the first substrate and the second substrate may easily pinch the large droplet to be split into at least two small droplets. When the microfluidic apparatus provided by the present disclosure performs the operation of merging at least two small droplets into large droplets, the distance D1 between the first substrate and the second substrate in the first region may be greater than the distance D2 between the first substrate and the second substrate in the second region; furthermore, relatively large distance D1 between the first substrate and the second substrate may provide a relatively large space, which may facilitate desirable and sufficient merging of at least two small droplets into the large droplet. In the microfluidic apparatus of the present disclosure, the flat first substrate and the second substrate may be obliquely and directly disposed to be opposite to each other at a certain angle, which may avoid using a flexible substrate to achieve different cell thicknesses resulting in increased process difficulty. In such way, the process may not only be simple, and different cell thicknesses of different regions may also be directly realized through a flat hard substrate, which may be compatible with driving droplets of different sizes, thereby realizing the operation of driving droplets of different sizes and splitting or merging droplets of different sizes and being beneficial for optimizing operational performance. Droplet merging may be realized in the position of the large cell thickness, so that the droplet merging may be more sufficient and efficient; and the droplet splitting may be realized at the position of the small cell thickness, so that the droplet splitting may be more stable and reliable.

Although some embodiments of the present disclosure have been described in detail through examples, those skilled in the art should understand that above-mentioned examples are provided for illustration only and not for the purpose of limiting the scope of the disclosure. Those skilled in the art should understand that modifications may be made to above-mentioned embodiments without departing from the scope and spirit of the present disclosure. The scope of the present disclosure may be defined by appended claims.

What is claimed is:

1. A microfluidic apparatus, comprising:

a first substrate and a second substrate which are oppositely disposed, wherein:

the first substrate and the second substrate are both smooth substrates;

an electrode array layer is on a side of the first substrate facing the second substrate, and a second electrode layer is on a side of the second substrate facing the first substrate;

the electrode array layer includes at least a plurality of first electrodes and a plurality of second electrodes;

in a direction in parallel with a plane of the first substrate, the first substrate includes a first region and a second region along a first direction;

the plurality of first electrodes is in the first region, and the plurality of second electrodes is in the second region;

in a direction perpendicular to the plane of the first substrate, a distance between the first substrate and the second substrate in the first region is D1, and a distance between the first substrate and the second substrate in the second region is D2, wherein D1>D2;

the second electrode layer is an entire-surface structure and connected to a ground signal;

along the first direction, a distance between the first substrate and the second substrate in the direction perpendicular to the plane of the first substrate gradually decreases from the first region to the second region;

an orthographic projection shape of a first electrode on the first substrate is a trapezoid, and an orthographic projection shape of a second electrode on the first substrate is a trapezoid; and the first electrode includes a first short side and a first long side in parallel along a second direction, and along the first direction, the first long side is on a side of the first short side adjacent to the second region, and the second electrode includes a second short side and a second long side in parallel along the second direction, and along the first direction, the second long side is on a side of the second short side away from the first region, so that the first long side of the first electrode is closer to the second region than the first short side of the first electrode, and the second short side of the second electrode is closer to the first region than the second long side of the second electrode.

2. The apparatus according to claim 1, wherein:

the first substrate and the second substrate form an angle $\alpha$, wherein $10 \leq \alpha \leq 30°$.

3. The apparatus according to claim 1, wherein:

along the first direction, the first substrate includes a plurality of sub-regions, and sizes of orthographic projection areas of electrodes of different sub-regions on the first substrate are different; and along the first direction, orthographic projection areas of electrodes of the plurality of sub-regions on the first substrate gradually decrease.

4. The apparatus according to claim 3, wherein:

orthographic projection areas of electrodes of one sub-region on the first substrate are the same.

5. The apparatus according to claim 1, wherein:

an orthographic projection area of the first electrode on the first substrate is greater than an orthographic projection area of the second electrode on the first substrate.

6. The apparatus according to claim 5, wherein:

a length of the first long side of the first electrode is greater than a length of the second long side of the second electrode along the second direction, wherein the first direction intersects the second direction.

7. The apparatus according to claim 6, wherein:

along the second direction, the length of the first long side of the first electrode is L1, the length of the second long side of the second electrode is L2, and $L1 = m \times L2$, wherein m is an integer greater than 1.

8. The apparatus according to claim 5, wherein:

along the first direction, the first substrate further includes a third region, and the third region is on a side of the second region away from the first region; and the electrode array layer in the third region includes a plurality of third electrodes, and an orthographic projection area of a third electrode of the plurality of third electrodes on the first substrate is less than the orthographic projection area of the second electrode on the first substrate.

9. The apparatus according to claim 8, wherein:

the electrode array layer in the second region includes one or more first collection electrodes, and along the second direction, the one or more first collection electrodes are on at least one side of the second electrode; and the electrode array layer in the third region includes one or more second collection electrodes, and along the second direction, the one or more second collection electrodes are on at least one side of the third electrode, wherein the first direction intersects the second direction.

10. The apparatus according to claim 9, wherein:

shapes and sizes of a first collection electrode and the second electrode are same, and shapes and sizes of a second collection electrode and the third electrode are same.

11. The apparatus according to claim 1, wherein:

the plurality of first electrodes includes at least a first sub-electrode and a second sub-electrode, and along the first direction, the first sub-electrode is on a side of the second sub-electrode away from the second region; and an orthographic projection area of the first sub-electrode on the first substrate is less than an orthographic projection area of the second sub-electrode on the first substrate.

12. The apparatus according to claim 11, wherein:

along the second direction, a length of a first short side of a first sub-electrode is L3, and a length of a first short side of a second sub-electrode is L4, wherein L4>L3;

along the second direction, a length of a first long side of the first sub-electrode is L5, and a length of a first long side of the second sub-electrode is L6, wherein L6>L5; and the first direction intersects the second direction.

13. The apparatus according to claim 1, wherein:

a first insulation hydrophobic layer is on a side of the electrode array layer facing the second substrate, and a second insulation hydrophobic layer is on a side of the second electrode layer facing the first substrate.

14. The apparatus according to claim 1, wherein:

a frame adhesive disposed by surrounding the electrode array layer is between the first substrate and the second substrate;

the frame adhesive includes at least a first sub-section and a second sub-section;

along the first direction, the first sub-section is on a side of the first region away from the second region, and the second sub-section is on a side of the second region away from the first region; and along the direction perpendicular to the plane of the first substrate, a thickness of the first sub-section is consistent, a thickness of the second sub-section is consistent, and the thickness of the first sub-section is greater than the thickness of the second sub-section.

15. The apparatus according to claim 14, wherein:

the frame adhesive further includes a third sub-section and a fourth sub-section;

two ends of the third sub-section are respectively connected to one end of the first sub-section and one end of the second sub-section;

two ends of the fourth sub-section are respectively connected to the other end of the first sub-section and the other end of the second sub-section;

in the direction perpendicular to the plane of the first substrate, a thickness of the third sub-section in the first region is greater than a thickness of the third sub-section in the second region; and in the direction perpendicular to the plane of the first substrate, a thickness of the fourth sub-section in the first region is greater than a thickness of the fourth sub-section in the second region.

16. The apparatus according to claim 1, wherein:

a first patch and a second patch are between the first substrate and the second substrate, the first patch and the second patch being parts of an insulation patch surrounding the electrode array layer;

along the first direction, the first patch is on a side of the first region away from the second region, and the second patch is on a side of the second region away from the first region; and in the direction perpendicular to the plane of the first substrate, a thickness of the first patch is consistent, a thickness of the second patch is consistent, and the thickness of the first patch is greater than the thickness of the second patch.

17. The apparatus according to claim 16, wherein:

a first filling adhesive strip and a second filling adhesive strip are further between the first substrate and the second substrate;

one end of the first patch and one end of the second patch are connected by the first filling adhesive strip, and the other end of the first patch and the other end of the second patch are connected by the second filling adhesive strip;

along the direction in parallel with the plane of the first substrate, the first filling adhesive strip and the second filling adhesive strip are respectively on two opposite sides of the electrode array layer;

the first patch, the first filling adhesive strip, the second patch, and the second filling adhesive strip form a structure surrounding the electrode array layer; and along the first direction, a thickness of the first filling adhesive strip in the direction perpendicular to the plane of the first substrate gradually decreases, and a thickness of the second filling adhesive strip in the direction perpendicular to the plane of the first substrate gradually decreases.

18. The apparatus according to claim 16, wherein:

a third patch and a fourth patch are further between the first substrate and the second substrate, the third patch and the fourth patch being also parts of the insulation patch surrounding the electrode array layer;

two ends of the third patch are respectively connected to one end of the first patch and one end of the second patch;

two ends of the fourth patch are respectively connected to the other end of the first patch and the other end of the second patch;

along the direction in parallel with the plane of the first substrate, the third patch and the fourth patch are respectively on two opposite sides of the electrode array layer;

the first patch, the third patch, the second patch, and the fourth patch integrally form a structure surrounding the electrode array layer; and along the first direction, a thickness of the third patch in the direction perpendicular to the plane of the first substrate gradually decreases, and a thickness of the fourth patch in the direction perpendicular to the plane of the first substrate gradually decreases.

* * * * *